United States Patent
Kawai

(10) Patent No.: US 10,633,397 B2
(45) Date of Patent: *Apr. 28, 2020

(54) SUBSTITUTED POLYCYCLIC PYRIDONE DERIVATIVES AND PRODRUGS THEREOF

(71) Applicant: Shionogi & Co., Ltd., Osaka-shi, Osaka (JP)

(72) Inventor: Makoto Kawai, Osaka (JP)

(73) Assignee: SHIONOGI & CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/221,733

(22) Filed: Dec. 17, 2018

(65) Prior Publication Data

US 2019/0112315 A1   Apr. 18, 2019

Related U.S. Application Data

(63) Continuation of application No. 15/569,191, filed as application No. PCT/JP2016/063139 on Apr. 27, 2016.

(30) Foreign Application Priority Data

Apr. 28, 2015 (JP) .................... 2015-090909
Dec. 3, 2015 (JP) .................... 2015-236844

(51) Int. Cl.
| | | |
|---|---|---|
| A61K 31/53 | (2006.01) | |
| C07D 498/14 | (2006.01) | |
| A61K 31/5383 | (2006.01) | |
| A61K 31/542 | (2006.01) | |
| A61K 31/553 | (2006.01) | |
| A61K 31/675 | (2006.01) | |
| C07F 9/6561 | (2006.01) | |
| C07D 471/14 | (2006.01) | |
| C07D 471/20 | (2006.01) | |
| C07D 491/22 | (2006.01) | |
| C07D 513/14 | (2006.01) | |
| A61P 31/16 | (2006.01) | |
| C07D 519/00 | (2006.01) | |
| C07F 7/18 | (2006.01) | |

(52) U.S. Cl.
CPC ............ C07D 498/14 (2013.01); A61K 31/53 (2013.01); A61K 31/5383 (2013.01);
(Continued)

(58) Field of Classification Search
CPC .. C07D 471/14; C07D 471/20; C07D 491/22; C07D 498/14; C07D 513/14;
(Continued)

(56) References Cited

U.S. PATENT DOCUMENTS

| 5,475,109 A | 12/1995 | Selnick et al. |
| 2005/0054645 A1 | 3/2005 | Miyazaki et al. |

(Continued)

FOREIGN PATENT DOCUMENTS

| EP | 1 950 212 | 7/2008 |
| EP | 2 444 400 | 4/2012 |

(Continued)

OTHER PUBLICATIONS

N.E. Sharpless et al., Nature Reviews Drug Discovery 1-14, 2 (2006).*

(Continued)

*Primary Examiner* — Deepak R Rao
(74) *Attorney, Agent, or Firm* — Wenderoth, Lind & Ponack, L.L.P.

(57) ABSTRACT

The present invention provides the following compounds having anti-viral activity.

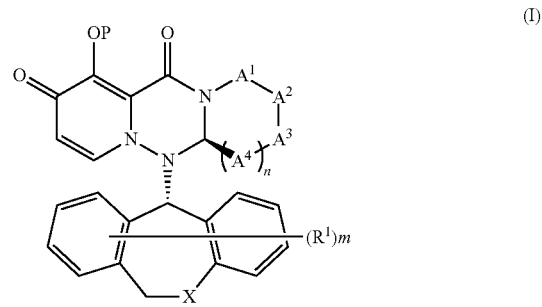

(I)

$A^1$ is $CR^{1A}R^{1B}$, S or O;
$A^2$ is $CR^{2A}R^{2B}$, S or O;
$A^3$ is $CR^{3A}R^{3B}$, S or O;
$A^4$ is $CR^{4A}R^{4B}$, S or O;
the number of hetero atoms among atoms constituting the ring which consists of $A^1, A^2, A^3, A^4$, nitrogen atom adjacent to $A^1$ and carbon atom adjacent to $A^1$, is 1 or 2;
$R^{1A}$ and $R^{1B}$ are each independently hydrogen, halogen, alkyl, or the like;
$R^{2A}$ and $R^{2B}$ are each independently hydrogen, halogen, alkyl, or the like;
$R^{3A}$ and $R^{3B}$ are each independently hydrogen, halogen, alkyl, or the like;
$R^{4A}$ and $R^{4B}$ are each independently hydrogen, halogen, alkyl, or the like;
$R^{3A}$ and $R^{3B}$ may be taken together to form non-aromatic carbocycle or non-aromatic heterocycle;
X is $CH_2$, S or O;
$R^1$ is each independently halogen, hydroxy, or the like;
m is any integer of 0 to 2; and
n is any integer of 1 to 2.

12 Claims, 1 Drawing Sheet

(52) U.S. Cl.
CPC .......... *A61K 31/542* (2013.01); *A61K 31/553* (2013.01); *A61K 31/675* (2013.01); *A61P 31/16* (2018.01); *C07D 471/14* (2013.01); *C07D 471/20* (2013.01); *C07D 491/22* (2013.01); *C07D 513/14* (2013.01); *C07D 519/00* (2013.01); *C07F 7/1804* (2013.01); *C07F 9/6561* (2013.01); C07C 2601/08 (2017.05); C07C 2601/16 (2017.05)

(58) Field of Classification Search
CPC .. C07D 519/00; A61K 31/53; A61K 31/5383; A61K 31/542; A61K 31/553; A61K 31/675
USPC .................................. 544/183, 184; 514/243
See application file for complete search history.

(56) References Cited

U.S. PATENT DOCUMENTS

| | | |
|---|---|---|
| 2006/0052361 A1 | 3/2006 | Miyazaki et al. |
| 2008/0161311 A1 | 7/2008 | Miyazaki et al. |
| 2013/0090300 A1 | 4/2013 | Bauman et al. |
| 2013/0096109 A1 | 4/2013 | Hattori et al. |
| 2013/0197219 A1 | 8/2013 | Takashashi et al. |
| 2015/0111854 A1 | 4/2015 | Takahashi et al. |

FOREIGN PATENT DOCUMENTS

| | | |
|---|---|---|
| GB | 2 280 435 | 2/1995 |
| WO | 2006/066414 | 6/2006 |
| WO | 2013/057251 | 4/2013 |
| WO | 2013/057253 | 4/2013 |
| WO | 2013/174930 | 11/2013 |
| WO | 2013/174931 | 11/2013 |
| WO | 2014/023691 | 2/2014 |
| WO | 2014/043252 | 3/2014 |
| WO | 2014/074926 | 5/2014 |
| WO | 2014/108406 | 7/2014 |
| WO | 2014/108407 | 7/2014 |
| WO | 2014/108408 | 7/2014 |
| WO | 2015/038655 | 3/2015 |
| WO | 2015/038660 | 3/2015 |
| WO | 2016/005330 | 1/2016 |
| WO | 2016/005331 | 1/2016 |
| WO | 2017/104691 | 6/2017 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
P.D. Griffiths, Cytomegalovirus in, Principles and Practice of Clinical Virology 85-122 (A.J. Zuckerman et al,, eds, 5th ed,, 2001).*
Sun et al., Synthesis and evaluation of a new series of substituted acyl(thio)urea and thiadiazolo[2,3-a]pyrimidine derivatives as potent inhibitors of influenza virus neuraminidase, Bioorganic & Medicinal Chemistry 14 (2006), pp. 8574-8581.*
International Search Report dated May 24, 2016 in International Application No. PCT/JP2016/063139.
Otto D. Hensens et al., "Isolation and Structure of Flutimide, a Novel Endonuclease Inhibitor of Influenza Virus", Tetrahedron Letters, vol. 36, No. 12, pp. 2005-2008, 1995.
Sheo B. Singh, "Total Synthesis of Flutimide, A Novel Endonuclease Inhibitor of Influenza Virus", Tetrahedron Letters, vol. 36, No. 12, pp. 2009-2012, 1995.
J. Tomassini et al., "Inhibition of Cap (m$^7$GppppXm)-Dependent Endonuclease of Influenza Virus by 4-Substituted 2,4-Dioxobutanoic Acid Compounds", Antimicrobial Agents and Chemotherapy, Dec. 1994, p. 2827-2837.
J.C. Hastings et al., "Anti-Influenza Virus Activities of 4-Substituted 2,4-Dioxobutanoic Acid Inhibitors", Antimicrobial Agents and Chemotherapy, May 1996, p. 1304-1307.
Kevin E. B. Parkes et al., "Use of a Pharmacophore Model to Discover a New Class of Influenza Endonuclease Inhibitors", J. Med. Chem. 2003, 46, 1153-1164.
Ajit K. Parhi et al., "Phenyl substituted 3-hydroxypyridin-2(1H)-ones: Inhibitors of influenza A endonculease", Bioorganic & Medicinal Chemistry 21 (2013) 6435-6446.
Brandi M. Baughman et al., "Identification of Influenza Endonuclease Inhibitors Using a Novel Fluorescence Polarization Assay", ACS Chemical Biology 2012, 7, 526-534.
Eric Chen et al., "Computation-Guided Discovery of Influenza Endonuclease Inhibitors", ACS Medicinal Chemistry Letters 2014, 5, 61-64.
Zhihui Yan et al., "Design of the influenza virus inhibitors targeting the PA endonuclease using 3D-QSAR modeling, side-chain hopping, and docking", Bioorganic & Medicinal Chemistry Letters 24 (2014) 539-547.
Hye Yeon Sagong et al., "3-Hydroxquinolin-2(1H)-ones as Inhibitors of Influenza A Endonuclease", ACS Medicinal Chemistry Letters, 2013, 4, 547-550.
Yuma Iwai et al., "Anti-influenza activity of phenethylphenylphthalimide analogs derived from thalidomide", Bioorganic & Medicinal Chemistry 18 (2010) 5379-5390.
Joseph D. Bauman et al., "Crystallographic Fragment Screening and Structure-Based Optimization Yields a New Class of Influenza Endonuclease Inhibitors", ACS Chemical Biology 2013, 8, 2501-2508.
Hye Yeon Sagong et al., "Phenyl Substituted 4-Hydroxpyridazin-3(2H)-ones and 5-Hydroxypyrimidin-4(3H)-ones: Inhibitors of Influenza A Endonuclease", Journal of Medicinal Chemistry 2014, 57, 8086-8098.
Nicolino Pala et al., "Virtual Screening and Biological Validation of Novel Influenza Virus PA Endonuclease Inhibitors", ACS Medicinal Chemistry Letters 2015, 6, 866-871.
Yuanchao Xie et al., "Caffeic acid derivatives: A new type of influenza neuraminidase inhibitors", Bioorganic & Medicinal Chemistry Letters 23 (2013) 3356-3560.
Y. Iwai et al., "Green tea catechins inhibit the endonuclease activity of influenza A virus RNA polymerase", PLoS Curr. 2009, RRN1052, pp. 1-15.
Yuma Iwai et al., "Anti-influenza Activity of Marchantins, Macrocyclic Bisbibenzyls Contained in Liverworts", PLoS One, 2011, e19825, pp. 1-11.
Masaki Shoji et al., "Anti-Influenza Activity of $C_{60}$ Fullerene Derivatives", PLoS One, 2013, e66337, pp. 1-10.
Sheo B. Singh et al., "Synthesis of Natural Flutimide and Analogous Full Substituted Pyrazine-2,6-diones, Endonuclease Inhibitors of Influenza Virus", J. Org. Chem. 2001, 66, 5504-5516.
International Preliminary Report on Patentability dated Nov. 9, 2017 in International Application No. PCT/JP2016/063139.
Ju et al., "Inhibitors of Influenza Virus Polymerase Acidic (PA) Endonuclease: Contemporary Developments and Perspectives", Journal of Medicinal Chemistry, vol. 60: pp. 3533-3551 (2017).
STN Registry (8 Compounds), Dec. 15, 2015.
Bundgaard, Design of Prodrugs, p. 1, 1985.
Silverman, Prodrugs and Drug Delivery Systems, The Organic Chemistry of Drug Design and Drug Action, pp. 352-399, 1992.
Banker et al., Prodrugs, Modern Pharmaceutics, Third Edition, Revised and Expanded, pp. 451 and 596 (1996).
Wolf, Some consideration for prodrug design, Burger's Medicinal Chemistry and Drug Discovery, 5$^{th}$ Edition, vol. 1: Principles and Practice, pp. 975-977, 1995.

\* cited by examiner

[Figure 1]
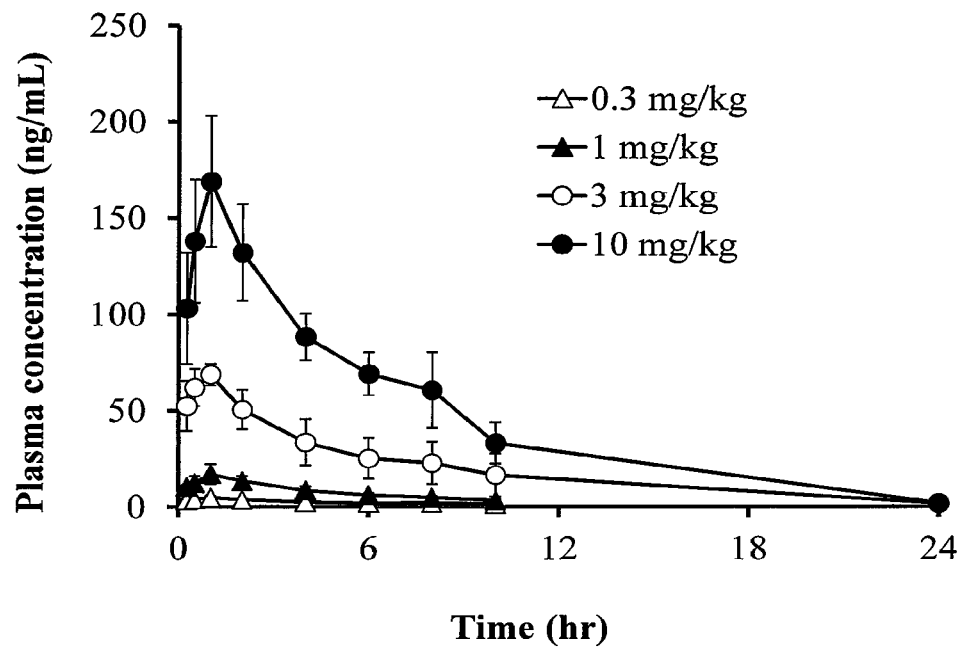
[Figure 2]
| Time | Plasma concentration (ng/mL) | | | |
|---|---|---|---|---|
| (hr) | 0.3 mg/kg | 1 mg/kg | 3 mg/kg | 10 mg/kg |
| 0.25 | BLQ | BLQ | BLQ | BLQ |
| 0.5 | BLQ | BLQ | BLQ | BLQ |
| 1 | BLQ | BLQ | BLQ | BLQ |
| 2 | BLQ | BLQ | BLQ | BLQ |
| 4 | BLQ | BLQ | BLQ | BLQ |
| 6 | BLQ | BLQ | BLQ | BLQ |
| 8 | BLQ | BLQ | BLQ | BLQ |
| 10 | BLQ | BLQ | BLQ | BLQ |
| 24 | BLQ | BLQ | BLQ | BLQ |
BLQ : below the lower limit of quantification (< 0.500 ng/mL)

SUBSTITUTED POLYCYCLIC PYRIDONE DERIVATIVES AND PRODRUGS THEREOF

TECHNICAL FIELD

This invention relates to substituted polycyclic pyridone derivatives having cap-dependent endonuclease inhibitory activity, prodrugs thereof, and pharmaceutical compositions including thereof.

BACKGROUND ART

Influenza is an acute respiratory infectious disease caused by infection with an influenza virus. In Japan, millions of influenza-like patients are reported every winter, and influenza is accompanied with high morbidity and mortality. Influenza is a particularly important disease in a high risk population such as baby and elderly, a complication rate with pneumonia is high in elderly, and death with influenza is occupied with elderly in many cases.

As anti-influenza drugs, Symmetrel (trade name: Amantadine) and Flumadine (trade name: Rimantadine) which inhibit the denucleation process of a virus, and Oseltamivir (trade name: Tamiflu) and Zanamivir (trade name: Relenza) which are neuraminidase inhibitors suppressing virus budding and release from a cell are known. However, since problems of appearances of resistant strains and side effects, and worldwide epidemic of a new-type influenza virus having high pathogenicity and mortality are feared, development of an anti-influenza drug having a novel mechanism has been desired.

Since a cap-dependent endonuclease which is an influenza virus-derived enzyme is essential for virus proliferation, and has the virus-specific enzymatic activity which is not possessed by a host, it is believed that the endonuclease is suitable for a target of an anti-influenza drug. The cap-dependent endonuclease of an influenza virus has a host mRNA precursor as a substrate, and has the endonuclease activity of producing a fragment of 9 to 13 bases including a cap structure (not including the number of bases of the cap structure). This fragment functions as a primer of a virus RNA polymerase, and is used in synthesizing mRNA encoding a virus protein. That is, it is believed that a substance which inhibits the cap-dependent endonuclease inhibits synthesis of a virus protein by inhibiting synthesis of virus mRNA and, as a result, inhibits virus proliferation.

As the substance which inhibits the cap-dependent endonuclease, flutimide (Patent Document 1 and Non-Patent Documents 1 and 2), 4-substituted 2,4-dioxobutanoic acid (Patent Document 2 and Non-Patent Documents 3 and 4), the compounds described in Patent Documents 3 to 12 and the like have been reported, but they have not yet led to clinical use as anti-influenza drugs. Patent Documents 9 and 12 describe compounds having a similar structure to that of this invention, but does not describe the compounds relating to the present invention. Also, Patent Documents 13 to 15 describe compounds having a similar structure to that of this invention as a compound having integrase inhibitory activity, however, the documents do not describe cap-dependent endonuclease. In addition, Patent Document 16 and 17 describes an invention relating to compounds having a similar structure to that of this invention as a compound having cap-dependent endonuclease inhibitory activity, which has been filed by the applicants, but does not describe the compounds relating to the present invention.

PRIOR ART DOCUMENTS

Patent Documents

Patent Document 1: GB2280435
Patent Document 2: U.S. Pat. No. 5,475,109
Patent Document 3: US20130090300
Patent Document 4: WO2013/057251
Patent Document 5: WO2013/174930
Patent Document 6: WO2014/023691
Patent Document 7: WO2014/043252
Patent Document 8: WO2014/074926
Patent Document 9: WO2014/108406
Patent Document 10: WO2014/108407
Patent Document 11: WO2014/108408
Patent Document 12: WO2015/038655
Patent Document 13: WO2005/016927
Patent Document 14: WO2006/066414
Patent Document 15: WO2007/049675
Patent Document 16: WO2010/147068
Patent Document 17: WO2012/039414

Non-Patent Documents

Non-Patent Document 1: Tetrahedron Lett 1995, 36(12), 2005
Non-Patent Document 2: Tetrahedron Lett 1995, 36(12), 2009
Non-Patent Document 3: Antimicrobial Agents And Chemotherapy, December 19 94, p. 2827-2837
Non-Patent Document 4: Antimicrobial Agents And Chemotherapy, May 19 96, p. 1304-1307

SUMMARY OF THE INVENTION

Problems to be Solved by the Invention

An object of the present invention is to provide compounds having antiviral activities, especially inhibiting growth activity of influenza virus. Another object of the present invention is to provide a prodrug prepared from compounds used for in vivo administration (for example, oral administration), being efficiently absorbed into the body after administration and showing high pharmacological effect.

Means for Solving the Problems

The present invention provides inventions shown below.
(1) A compound represented by formula (I):

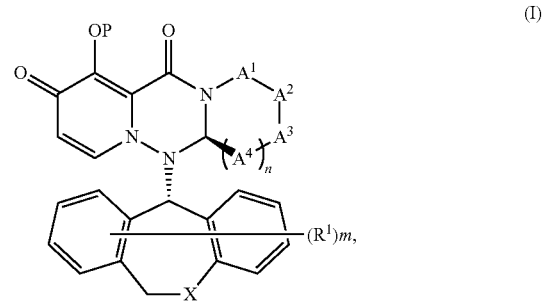

or its pharmaceutically acceptable salt:
wherein
P is hydrogen or a group $P^R$ to form a prodrug;
$A^1$ is $CR^{1A}R^{1B}$, S or O;
$A^2$ is $CR^{2A}R^{2B}$, S or O;
$A^3$ is $CR^{3A}R^{3B}$, S or O;
$A^4$ is each independently $CR^{4A}R^{4B}$, S or O;
the number of hetero atoms among atoms constituting the ring which consists of $A^1$, $A^2$, $A^3$, $A^4$, nitrogen atom adjacent to $A^1$ and carbon atom adjacent to $A^4$, is 1 or 2;
$R^{1A}$ and $R^{1B}$ are each independently hydrogen, halogen, alkyl, haloalkyl, alkyloxy or phenyl;
$R^{2A}$ and $R^{2B}$ are each independently hydrogen, halogen, alkyl, haloalkyl, alkyloxy or phenyl;
$R^{3A}$ and $R^{3B}$ are each independently hydrogen, halogen, alkyl, haloalkyl, alkyloxy or phenyl;
$R^{4A}$ and $R^{4B}$ are each independently hydrogen, halogen, alkyl, haloalkyl, alkyloxy or phenyl;
$R^{3A}$ and $R^{3B}$ may be taken together with an adjacent carbon atom to form non-aromatic carbocycle or non-aromatic heterocycle;
X is $CH_2$, S or O;
$R^1$ is each independently halogen, hydroxy, alkyl, haloalkyl or alkyloxy;
m is any integer of 0 to 2; and
n is any integer of 1 to 2;
provided that the following compounds are excluded:

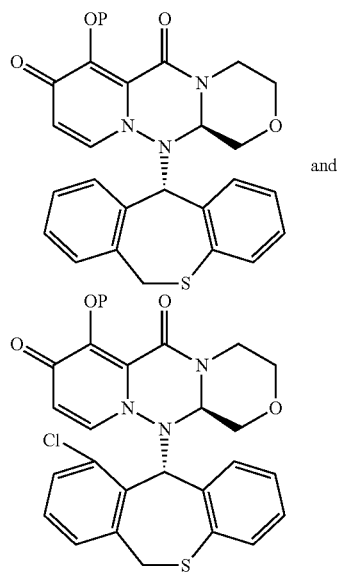

and wherein each definition has the same meaning as described above.
(2) The compound according to (1), wherein the group represented by formula:

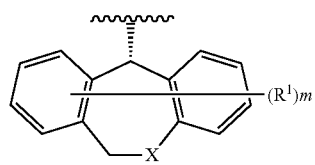

wherein each definition has the same meaning as described (1)

is a group represented by formula:

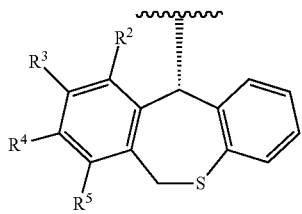

wherein $R^2$, $R^3$, $R^4$ and $R^5$ are each independently hydrogen or fluorine; the number of fluorine atoms of $R^2$, $R^3$, $R^4$ and $R^5$ is 1 or 2, or its pharmaceutically acceptable salt.
(3) The compound according to (1), wherein the group represented by formula:

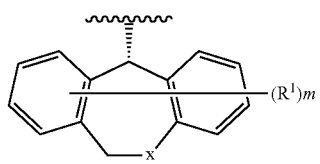

wherein each definition has the same meaning as described (1)

is a group represented by formula:

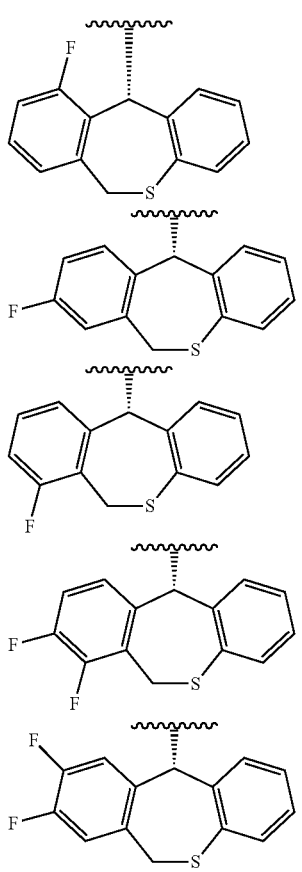

or

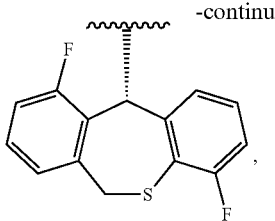

or its pharmaceutically acceptable salt.

(4) The compound according to any one of (1) to (3), wherein the group represented by formula:

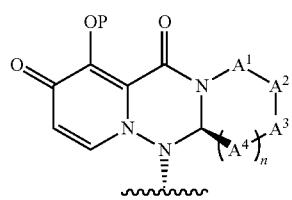

wherein each definition has the same meaning as described (1)
is represented by formula:

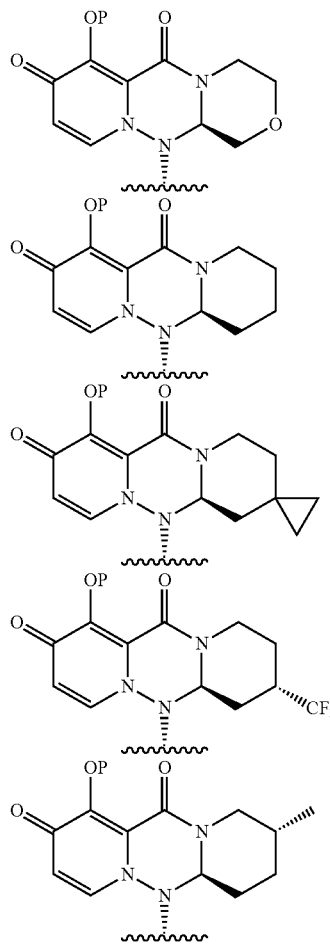

wherein each definition has the same meaning as described (1), or its pharmaceutically acceptable salt.

(5) The compound according to (1) represented by the following formula:

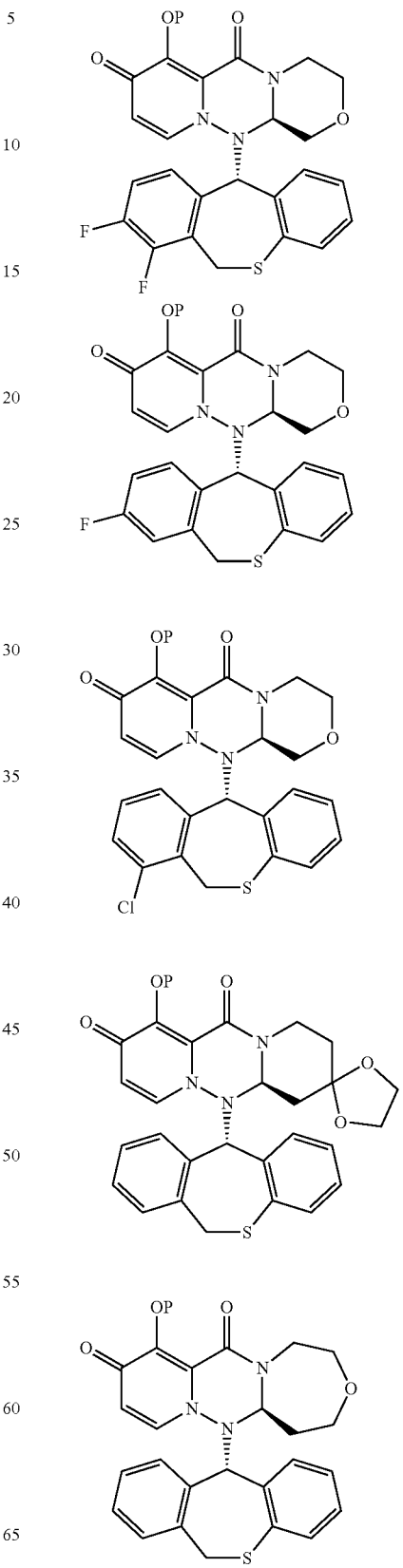

7
-continued
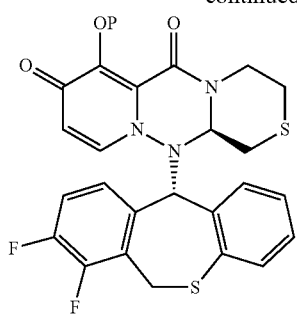
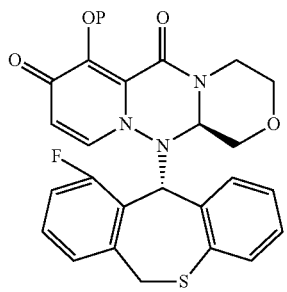
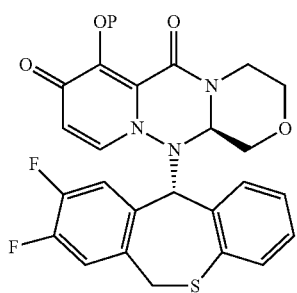
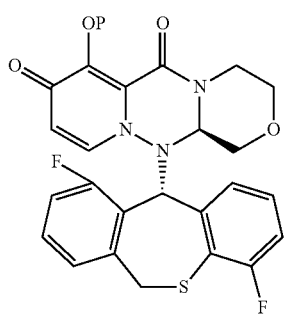
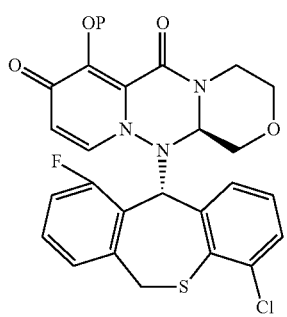
8
-continued
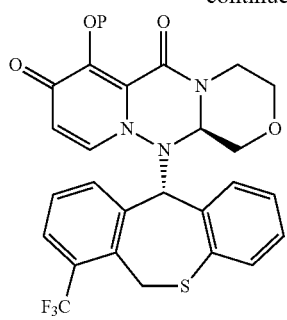
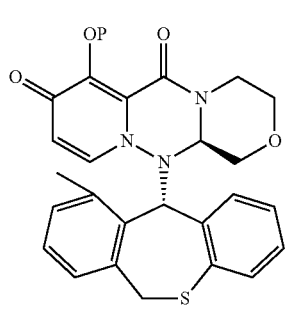
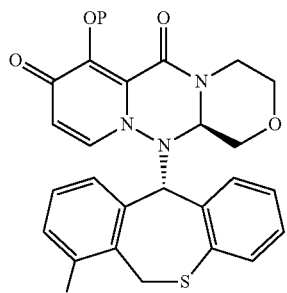
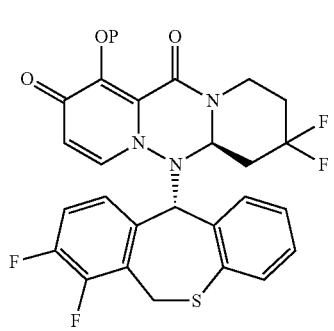
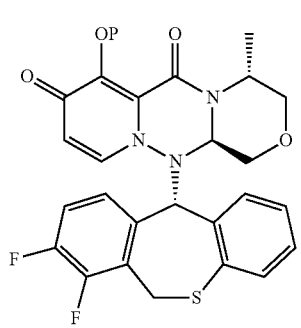

-continued
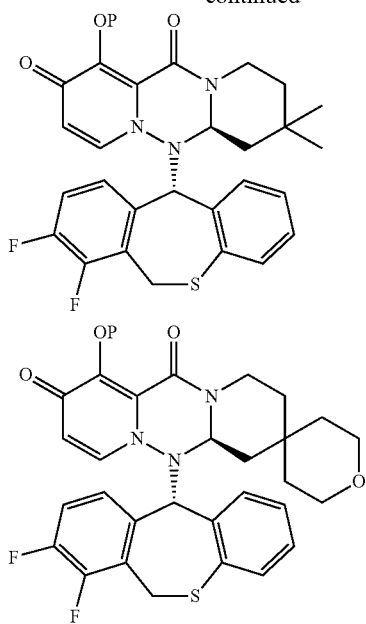
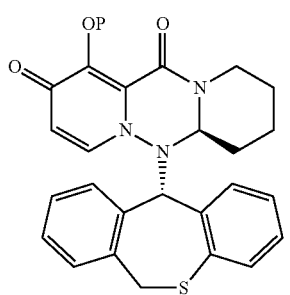
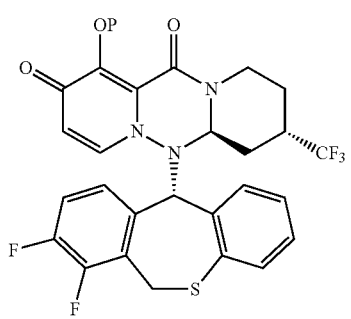
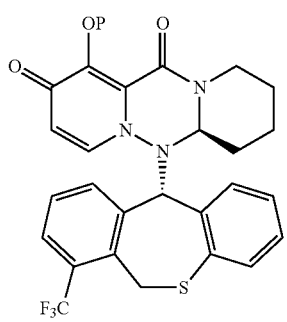
-continued
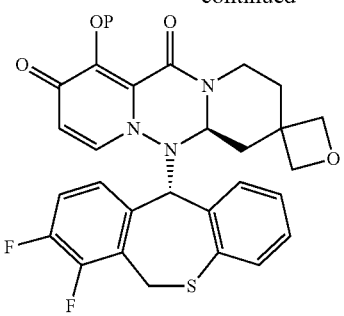
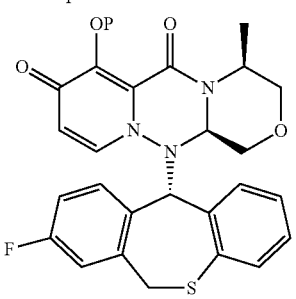
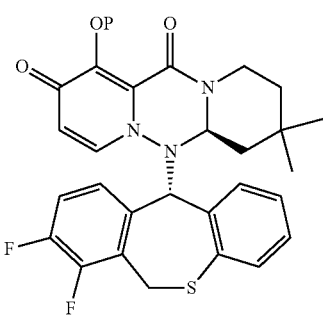
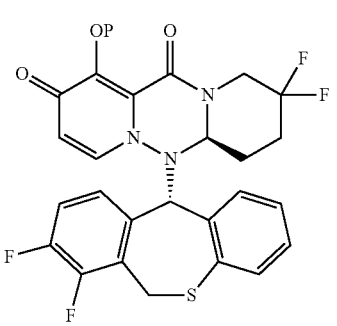
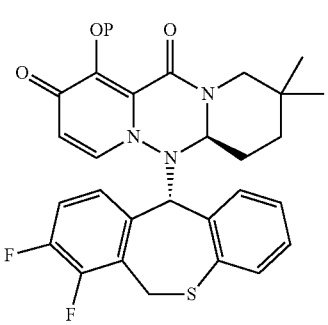

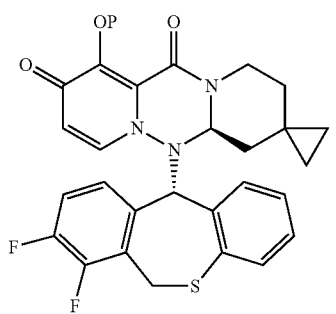
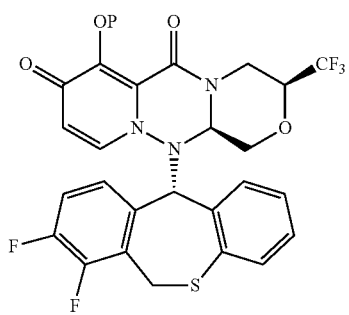
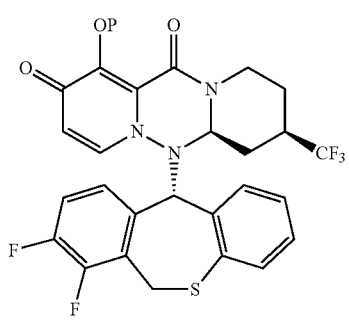
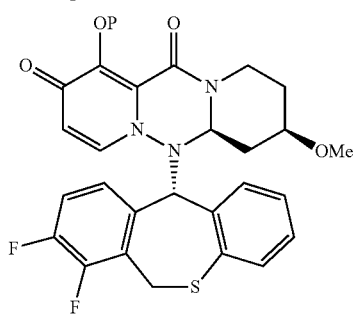
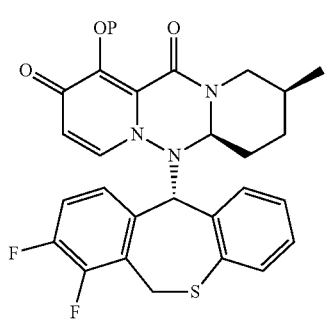
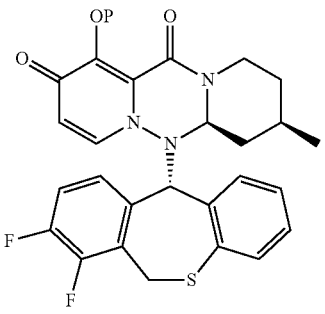
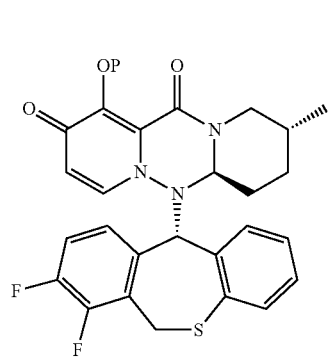
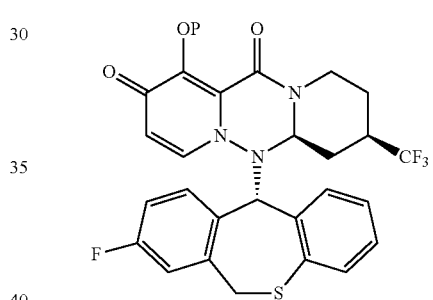
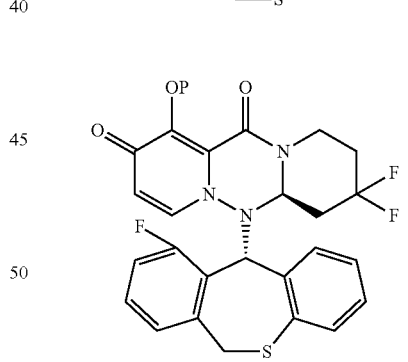
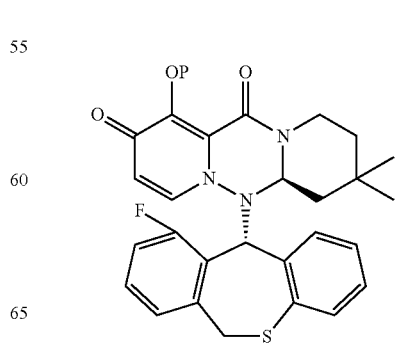

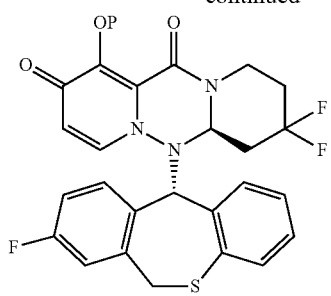

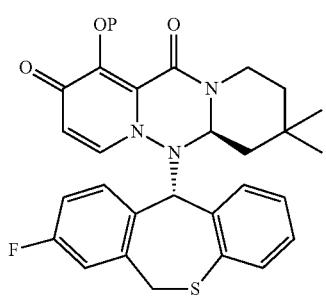

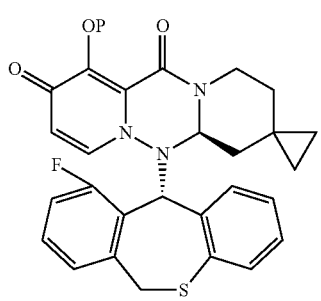

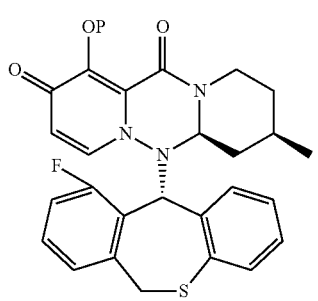

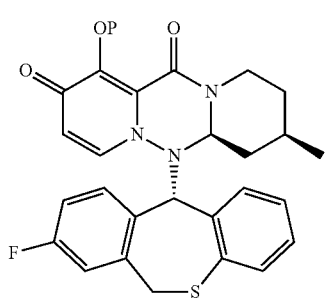

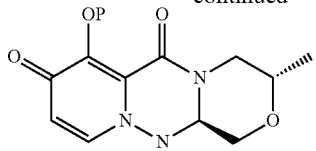

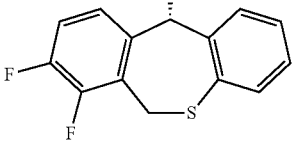

wherein each definition has the same meaning as described (1), or its pharmaceutically acceptable salt.

(6) The compound according to (1) represented by the following formula:

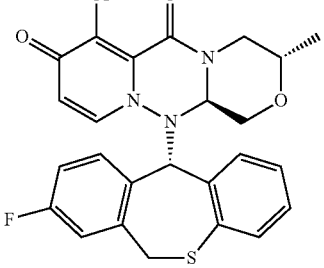

wherein each definition has the same meaning as described (1), or its pharmaceutically acceptable salt.

(7) The compound according to (1), represented by the following formula:

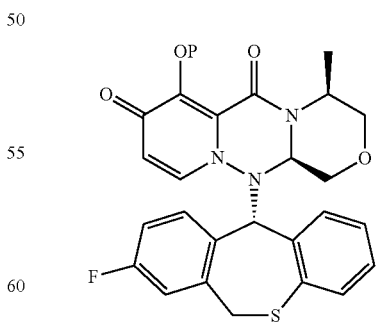

wherein each definition has the same meaning as described (1), or its pharmaceutically acceptable salt.

(8) The compound according to (1), represented by the following formula:

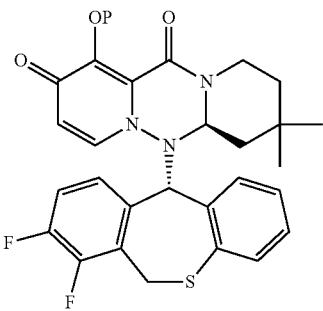

wherein each definition has the same meaning as described (1), or its pharmaceutically acceptable salt.

(9) The compound according to (1), represented by the following formula:

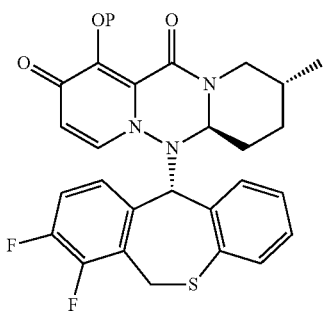

wherein each definition has the same meaning as described (1), or its pharmaceutically acceptable salt.

(10) The compound according to (1), represented by the following formula:

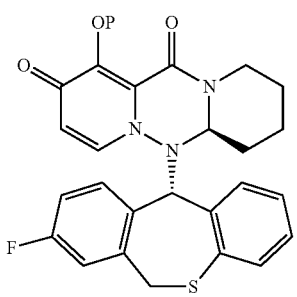

wherein each definition has the same meaning as described in claim 1, or its pharmaceutically acceptable salt.

(11) The compound represented by the following formula:

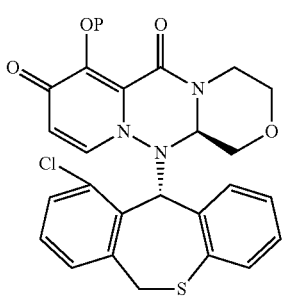

wherein P is hydrogen or a group $P^R$ to form a prodrug, or its pharmaceutically acceptable salt.

(12) The compound according to any one of (1) to (11), or its pharmaceutically acceptable salt,
wherein $P^R$ is a group selected from the following formula a) to ac):
a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N(—K)($P^{R2}$),
i) —C(=O)—O-L-O—$P^{R2}$,
j) —C($P^{R3}$)$_2$—O—$P^{R4}$,
k) —C($P^{R3}$)$_2$—O-L-O—$P^{R4}$,
l) —C($P^{R3}$)$_2$—O—C(=O)—$P^{R4}$,
m) —C($P^{R3}$)$_2$—O—C(=O)—O—$P^{R4}$,
n) —C($P^{R3}$)$_2$—O—C(=O)—N(—K)—$P^{R4}$,
o) —C($P^{R3}$)$_2$—O—C(=O)—O-L-O—$P^{R4}$,
p) —C($P^{R3}$)$_2$O—C(=O)—O-L-N($P^{R4}$)$_2$,
q) —C($P^{R3}$)$_2$—O—C(=O)N(—K)-L-O—$P^{R4}$,
r) —C($P^{R3}$)—O—C(=O)—N(—K)-L-N($P^{R4}$)$_2$,
s) —C($P^{R3}$)$_2$—O—C(=O)—O-L-O-L-O—$P^{R4}$,
t) —C($P^{R3}$)$_2$—O—C(=O)—O-L-N(—K)—C(=O)—$P^{R4}$,
u) —C($P^{R3}$)$_2$—O—P(=O)(—$P^{R5}$)$_2$,
v) —C($P^{R3}$)$_2$—$P^{R6}$,
w) —C(=N$^+$($P^{R7}$)$_2$)(—N($P^{R7}$)$_2$),
x) —C($P^{R3}$)$_2$—C($P^{R3}$)$_2$—C(=O)—O—$P^{R2}$,
y) —C($P^{R3}$)$_2$—N(—K)—C(=O)—O—$P^{R2}$,
z) —P(=O)(—$P^{R8}$)($P^{R9}$),
aa) —S(=O)$_2$—$P^{R10}$,
ab) —$P^{R11}$, and
ac) —C($P^{R3}$)$_2$—C($P^{R3}$)$_2$—O—$P^{R2}$,
wherein L is straight or branched alkylene, or straight or branched alkenylene;
K is hydrogen, or alkyl optionally substituted by substituent group A;
$P^{R0}$ is alkyl optionally substituted by substituent group A, or alkenyl optionally substituted by substituent group A;
$P^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;
$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;
$P^{R3}$ is each independently hydrogen or alkyl;
$P^{R4}$ is each independently alkyl optionally substituted by substituent group A, carbocyclyl group optionally substituted by substituent group A, heterocyclyl group optionally substituted by substituent group A, alkylamino optionally substituted by substituent group A, carbocyclylalkyl optionally substituted by substituent group A, heterocyclylalkyl optionally substituted by substituent group A, or trialkylsilyl;
$P^{R5}$ is each independently hydroxy or OBn;
$P^{R6}$ is carbocyclyl group optionally substituted by substituent group A, or heterocyclyl group optionally substituted by substituent group A;
$P^{R7}$ is each independently alkyl optionally substituted by substituent group A;

P$^{R8}$ is alkyloxy optionally substituted by substituent group A;
P$^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A;
P$^{R8}$ and P$^{R9}$ may be taken together with an adjacent phosphorus atom to form heterocycle optionally substituted by substituent group A;
P$^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A;
P$^{R11}$ is alkyl optionally substituted by substituent group A, alkenyl optionally substituted by substituent group A, carbocyclyl group optionally substituted by substituent group A, or heterocyclyl group optionally substituted by substituent group A;
Substituent group A; oxo, alkyl, hydroxyalkyl, amino, alkylamino, carbocyclyl group, heterocyclyl group, carbocyclylalkyl, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho.
(13) The compound according to (12), or its pharmaceutically acceptable salt, wherein P$^R$ is a group selected from the following formula:
a) —C(═O)—P$^{R0}$,
b) —C(═O)—P$^{R1}$,
g) —C(═O)—O—P$^{R2}$,
h) —C(═O)—N(—K)(P$^{R2}$),
i) —C(═O)—O-L-O—P$^{R2}$,
l) —C(P$^{R3}$)$_2$—O—C(═O)—P$^{R4}$,
m) —C(P$^{R3}$)$_2$—O—C(═O)—O—P$^{R4}$,
o) —C(P$^{R3}$)$_2$—O—C(═O)—O-L-O—P$^{R4}$,
v) —C(P$^{R3}$)$_2$—P$^{R6}$,
x) —C(P$^{R3}$)$_2$—C(P$^{R3}$)$_2$—C(═O)—O—P$^{R2}$,
y) —C(P$^{R3}$)$_2$—N(—K)—C(═O)—O—P$^{R2}$, and
z) —P(═O)(—P$^{R8}$)(—P$^{R9}$),
wherein L is straight or branched alkylene;
K is hydrogen or alkyl optionally substituted by substituent group A;
P$^{R0}$ is alkyl optionally substituted by substituent group A;
P$^{R1}$ is carbocyclyl group optionally substituted by substituent group A, or heterocyclyl group optionally substituted by substituent group A;
P$^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, or heterocyclylalkyl optionally substituted by substituent group A;
P$^{R3}$ is each independently hydrogen or alkyl;
P$^{R4}$ is alkyl optionally substituted by substituent group A, carbocyclyl group optionally substituted by substituent group A, or heterocyclyl group optionally substituted by substituent group A;
P$^{R6}$ is carbocyclyl group optionally substituted by substituent group A, or heterocyclyl group optionally substituted by substituent group A;

P$^{R8}$ is alkyloxy optionally substituted by substituent group A;
P$^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; and
P$^{R8}$ and P$^{R9}$ may be taken together with an adjacent phosphorus atom to form heterocycle optionally substituted by substituent group A,
Substituent group A; oxo, alkyl, alkylamino, carbocyclyl group, heterocyclyl group, alkylcarbonyl, halogen, hydroxy, alkylcarbonylamino, alkylcarbonyloxy, alkyloxycarbonyl, alkyloxycarbonylalkyl, alkylaminocarbonyloxy, alkyloxy, cyano, nitro, azido, alkylsulfonyl and trialkylsilyl.
(14) A compound represented by following formula:

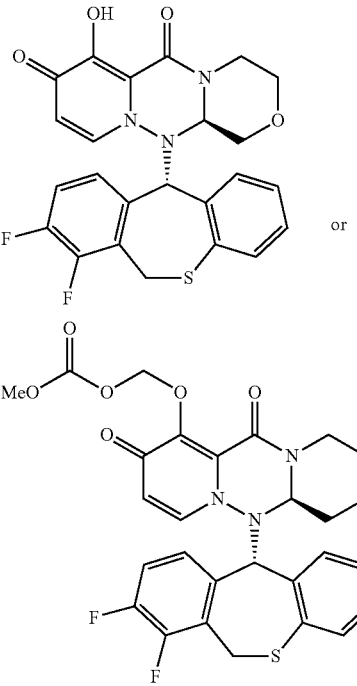

or its pharmaceutically acceptable salt.
(15) A compound represented by the following formula:

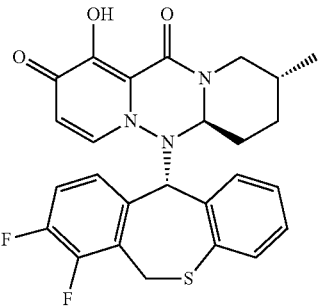

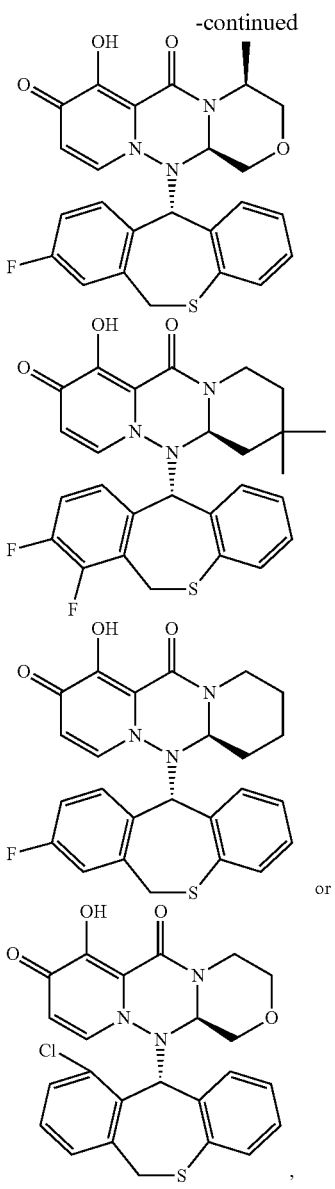

or its pharmaceutically acceptable salt.

(16) A pharmaceutical composition comprising the compound of any one of (1) to (15), or its pharmaceutically acceptable salt.

(17) The pharmaceutical composition according to (16), which exhibits anti influenza activity.

(18) The pharmaceutical composition according to (16), which exhibits cap-dependent endonuclease inhibitory activity.

(19) A method for treating and/or preventing disease caused by a virus having cap-dependent endonuclease characterized in administering the compound of any one of (1) to (15), or its pharmaceutically acceptable salt.

(20) A compound according to any one of (1) to (15) or its pharmaceutically acceptable salt, for treating or preventing disease caused by a virus having cap-dependent endonuclease.

(21) A use of the compound according to any one of (1) to (15) or its pharmaceutically acceptable salt, for the production of a therapeutic or prophylactic agent for disease caused by a virus having cap-dependent endonuclease.

(22) A pharmaceutical composition comprising the compound of any one of (1) to (15), or its pharmaceutically acceptable salt, for oral administration.

(23) The pharmaceutical composition according to (22), which is a tablet, powder, granule, capsule, pill, film, suspension, emulsion, elixir, syrup, lemonade, spirit, aromatic water, extract, decoction or tincture.

(24) The pharmaceutical composition of according to (16), which is a sugar-coated tablet, film-coated tablet, enteric-coated tablet, sustained-release tablet, troche tablet, sublingual tablet, buccal tablet, chewable tablet, orally disintegrated tablet, dry syrup, soft capsule, micro capsule or sustained-release capsule.

(25) A pharmaceutical composition comprising the compound according to any one of (1) to (15), or its pharmaceutically acceptable salt, for parenteral administration.

(26) The pharmaceutical composition according to (25), for dermal, subcutaneous, intravenous, intraarterial, intramuscular, intraperitoneal, transmucosal, inhalation, transnasal, ophthalmic, inner ear or vaginal administration.

(27) The pharmaceutical composition according to (25) or (26), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(28) A pharmaceutical composition comprising the compound according to any one of (1) to (15), or its pharmaceutically acceptable salt, for a pediatric or geriatric patient.

(29) A pharmaceutical composition consisting of a combination of the compound according to any one of (1) to (15) or its pharmaceutically acceptable salt and Neuraminidase inhibitor, RNA-dependent RNA polymerase inhibitor, M2 protein inhibitor, PB2 Cap binding inhibitor, an anti-HA antibody or immunological agent.

(30) A pharmaceutical composition comprising the compound according to any one of (1) to (15), or its pharmaceutically acceptable salt, for a combination therapy with Neuraminidase inhibitor, RNA-dependent RNA polymerase inhibitor, M2 protein inhibitor, PB2 Cap binding inhibitor, an anti-HA antibody or immunological agent.

The present invention further provides a method for treating or preventing influenza infectious disease using the prodrug compound and the compound which exhibits anti influenza activity. The present invention further provides a parent compound of the prodrug compound. The parent compound is effective as an anti-influenza agent or an intermediate of the prodrug compound.

Effect of the Invention

The compound according to the present invention has an inhibitory activity on cap-dependent endonuclease. More preferred compound is a prodrug, and the prodrug becomes a parent compound having an inhibitory activity on cap-dependent endonuclease in vivo after administration, thus is effective as a therapeutic agent and/or preventive agent for influenza infectious disease.

BRIEF DESCRIPTION OF DRAWINGS

FIG. 1 is a result of measuring the plasma concentration of compound III-2, after oral administration of prodrug Compound II-6, the parent compound of which is Compound III-2, to rat under non-fasting conditions.

FIG. 2 is a result of measuring the plasma concentration of compound II-6, after oral administration of prodrug Compound II-6, the parent compound of which is Compound III-2, to rat under non-fasting conditions.

BEST MODE FOR CARRYING OUT THE INVENTION

The meaning of each term used in the present description is explained below. Each term is used in a unified sense, and is used in the same sense when used alone, or when used in combination of other term.

The term of "consisting of" means having only components.

The term of "comprising" means not restricting with components and not excluding undescribed factors.

"Optionally substituted by substituent group A" means that an arbitrary position may be substituted by one, two or more same or different substituents selected from substituent group A.

"Prodrug" in the present description refers to a compound represented by formula (II) in the following reaction formula:

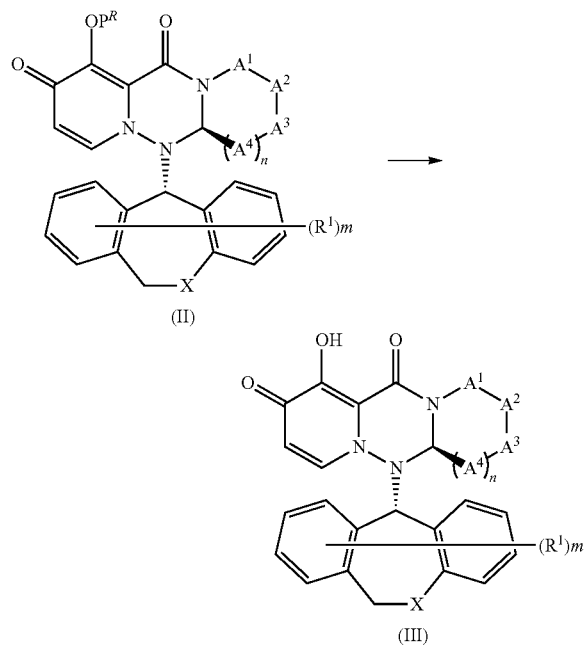

wherein each symbol is same as the above,
or its pharmaceutically acceptable salt, and means a compound showing cap-dependant endonuclease (CEN) inhibitory activity and/or CPE inhibitory effect by being converted into a compound represented by formula (III) by a decomposition reaction caused by drug-metabolizing enzymes, hydrolases, gastric acids, enterobacteria, etc. under physiological conditions in vivo.

The prodrug more preferably means a compound in which bioavailability and/or AUC (area under the blood concentration curve) in in vivo administration is improved more than those of the compound represented by formula (III).

Therefore, the prodrug is efficiently absorbed into the body in the stomach and/or intestines after in vivo administration (for example, oral administration), then converted into the compound represented by formula (III). Thus, the prodrug preferably shows an effect of treating and/or preventing influenza higher than the compound represented by formula (III).

One embodiment of the "group represented by

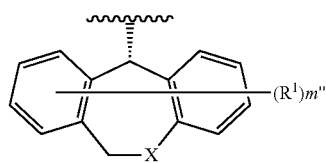

wherein each definition has the same meaning as described (1), is a group represented by formula:

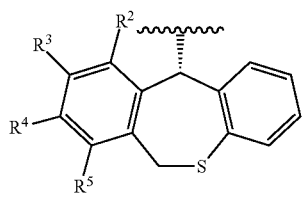

wherein $R^2$, $R^3$, $R^4$ and $R^6$ are each independently hydrogen or fluorine; the number of fluorine atoms of $R^2$, $R^3$, $R^4$ and $R^5$ is 1 or 2.

Another embodiment is a group represented by formula:

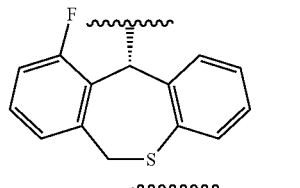

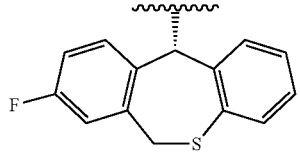

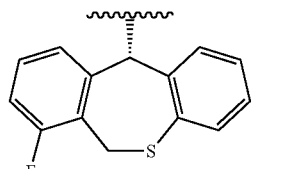

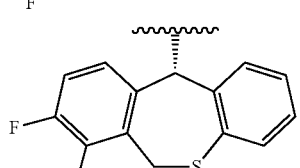

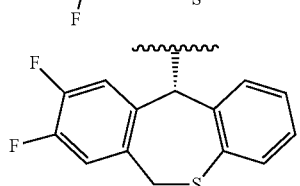

or

-continued

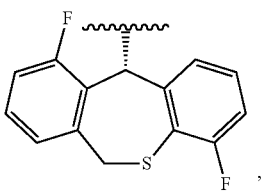

and a group represented by formula:

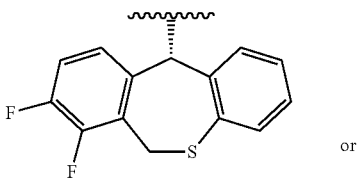

or

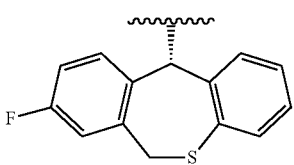

is preferable, and a group represented by formula:

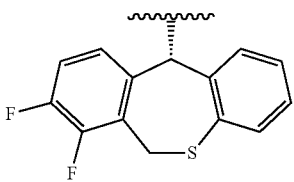 [SMILES: *[C@@H]1c2ccccc2SCc2c1ccc(F)c2F]

is especially preferable.

"Group P$^R$ to form a prodrug" in the present description refers to a "P$^R$" group in the formula (II), in the following reaction formula:

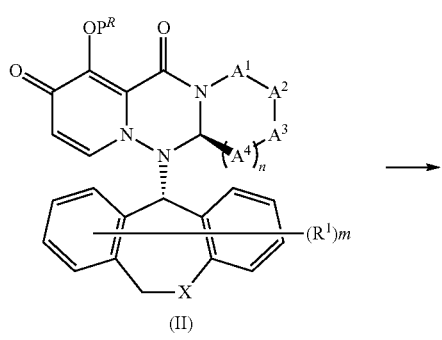

→

-continued wherein each symbol is same as the above,
and —OP$^R$ group is converted into —OH group in the formula (III) by a decomposition reaction caused by drug-metabolizing enzymes, hydrolases, gastric acids, enterobacteria, etc. under physiological conditions in vivo.

The "group P$^R$ to form a prodrug" more preferably means a group that improves bioavailability and/or AUC (area under the blood concentration curve) of the compound represented by formula (III) by being added to the compound represented by formula (III).

Examples of the group P$^R$ to form a prodrug include the groups described in Prog. Med. 5: 2157-2161 (1985) and Supplied by The British Library—"The world's Knowledge".

The "P$^R$" group in —OP$^R$ group in the formula (I) or (II) may be a group converted into —OH group in vivo, and examples preferably include a group selected from the following formulae a) to ac).

a) —C(=O)—P$^{R0}$,
b) —C(=O)—P$^{R1}$,
c) —C(=O)-L-P$^{R1}$,
d) —C(=O)-L-O—P$^{R1}$,
e) —C(=O)-L-O-L-O—P$^{R1}$,
f) —C(=O)-L-O—C(=O)—P$^{R1}$
g) —C(=O)—O—P$^{R2}$,
h) —C(=O)—N(—K)(P$^{R2}$),
i) —C(=O)—O-L-O—P$^{R2}$,
j) —C(P$^{R3}$)$_2$—O—P$^{R4}$
k) —C(P$^{R3}$)$_2$—O-L-O—P$^{R4}$,
l) —C(P$^{R3}$)$_2$—O—C(=O)—P$^{R4}$,
m) —C(P$^{R3}$)$_2$—O—C(=O)—O—P$^{R4}$,
n) —C(P$^{R3}$)$_2$—O—C(=O)—N(—K)—P$^{R4}$,
o) —C(P$^{R3}$)$_2$—O—C(=O)—O-L-O—P$^{R4}$,
p) —C(P$^{R3}$)$_2$—O—C(=O)—O-L-N(P$^{R4}$)$_2$,
q) —C(P$^{R3}$)$_2$—O—C(=O)—N(—K)-L-O—P$^{R4}$,
r) —C(P$^{R3}$)$_2$—O—C(=O)—N(—K)-L-N(P$^{R4}$)$_2$,
s) —C(P$^{R3}$)$_2$—O—C(=O)—O-L-O-L-O—P$^{R4}$,
t) —C(P$^{R3}$)$_2$—O—C(=O)—O-L-N(—K)—C(=O)—P$^{R4}$,
u) —C(P$^{R3}$)$_2$—O—P(=O)(—P$^{R5}$)$_2$,
v) —C(P$^{R3}$)$_2$—P$^{R6}$ (except for a benzyl group),
w) —C(=N$^+$(P$^{R7}$)$_2$)(—N(P$^{R7}$)$_2$),
x) —C(P$^{R3}$)$_2$—C(P$^{R3}$)$_2$—C(=O)—O—P$^{R2}$,
y) —C(P$^{R3}$)$_2$—N(—K)—C(=O)—O—P$^{R2}$,
z) —P(=O)(—P$^{R8}$)(—P$^{R9}$),
aa) —S(=O)$_2$—P$^{R10}$,
ab) —P$^{R11}$, and
ac) —C(P$^{R3}$)$_2$—C(P$^{R3}$)$_2$—O—P$^{R2}$,
wherein L is straight or branched alkylene, or straight or branched alkenylene;
K is hydrogen, or alkyl optionally substituted by substituent group A;

$P^{R0}$ is alkyl optionally substituted by substituent group A, or alkenyl optionally substituted by substituent group A;

$P^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;

$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;

$P^{R3}$ is each independently hydrogen or alkyl;

$P^{R4}$ is each independently alkyl optionally substituted by substituent group A, carbocyclyl group optionally substituted by substituent group A, heterocyclyl group optionally substituted by substituent group A, alkylamino optionally substituted by substituent group A, carbocyclylalkyl optionally substituted by substituent group A, heterocyclylalkyl optionally substituted by substituent group A, or trialkylsilyl;

$P^{R5}$ is each independently hydroxy or OBn;

$P^{R6}$ is carbocyclyl group optionally substituted by substituent group A, or heterocyclyl group optionally substituted by substituent group A;

$P^{R7}$ is each independently alkyl optionally substituted by substituent group A;

$P^{R8}$ is alkyloxy optionally substituted by substituent group A;

$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A;

$P^{R8}$ and $P^{R9}$ may be taken together with an adjacent phosphorus atom to form heterocycle optionally substituted by substituent group A;

$P^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A;

$P^{R11}$ is alkyl optionally substituted by substituent group A, alkenyl optionally substituted by substituent group A, carbocyclyl group optionally substituted by substituent group A, or heterocyclyl group optionally substituted by substituent group A.

Substituent group A; oxo, alkyl, hydroxyalkyl, amino, alkylamino, carbocyclyl, heterocyclyl, carbocyclylalkyl, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho.

The group $P^R$ to form a prodrug is preferably a group selected from the followings.

a) —C(=O)—$P^{R0}$,
b) —C(=O)—$P^{R1}$,
g) —C(=O)—O—$P^{R2}$,
h) —C(=O)—N(—K)($P^{R2}$),
i) —C(=O)—O-L-O—$P^{R2}$
l) —C($P^{R3}$)$_2$—O—C(=O)$P^{R4}$,
m) —C($P^{R3}$)$_2$—O—C(=O)—O—$P^{R4}$,
o) —C($P^{R3}$)$_2$—O—C(=O)—O-L-O—$P^{R4}$,
v) —C($P^{R3}$)$_2$—$P^{R6}$ (except for a benzyl group),
x) —C($P^{R3}$)$_2$—C($P^{R3}$)$_2$—C(=O)—O—$P^{R2}$,
y) —C($P^{R3}$)$_2$—N(—K)—C(=O)—O—$P^{R2}$, and
z) —P(=O)(—$P^{R8}$)(—$P^{R9}$), wherein L is straight or branched alkylene;

K is hydrogen, or alkyl optionally substituted by substituent group A;

$P^{R0}$ is alkyl optionally substituted by substituent group A;

$P^{R1}$ is carbocyclyl group optionally substituted by substituent group A, or heterocyclyl group optionally substituted by substituent group A;

$P^{R2}$ is each independently alkyl optionally substituted by substituent group A, carbocyclyl group optionally substituted by substituent group A, heterocyclyl group optionally substituted by substituent group A, carbocyclylalkyl optionally substituted by substituent group A, or heterocyclylalkyl optionally substituted by substituent group A;

$P^{R3}$ is each independently hydrogen or alkyl;

$P^{R4}$ is each independently alkyl optionally substituted by substituent group A, carbocyclyl group optionally substituted by substituent group A, or heterocyclyl group optionally substituted by substituent group A;

$P^{R6}$ is carbocyclyl group optionally substituted by substituent group A, or heterocyclyl group optionally substituted by substituent group A;

$P^{R8}$ is alkyloxy optionally substituted by substituent group A;

$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; and $P^{R8}$ and $P^{R9}$ may be taken together with an adjacent phosphorus atom to form heterocycle optionally substituted by substituent group A.

Substituent group A; oxo, alkyl, alkylamino, carbocyclyl, heterocyclyl, alkylcarbonyl, halogen, hydroxy, alkylcarbonylamino, alkylcarbonyloxy, alkyloxycarbonyl, alkyloxycarbonylalkyl, alkylaminocarbonyloxy, alkyloxy, nitro, azido, alkylsulfonyl and trialkylsilyl.

"Converted into a prodrug" in the present description means that, as shown in the following reaction formula:

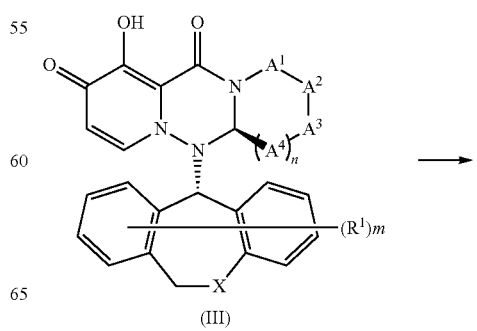

(III)

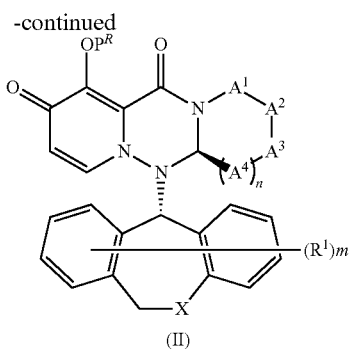

(II)

wherein each symbol is same as the above, a hydroxy group in the formula (III) or its pharmaceutically acceptable salt is converted into —OP$^R$ group.

"Parent compound" in the present description means a compound to be a source before synthesizing the "prodrug" and/or a compound released from the "prodrug" by the reaction by enzymes, a gastric acid, and the like under physiological conditions in vivo, and specifically means a compound shown by the formula (III), or pharmaceutically acceptable salt thereof or a solvate thereof.

The term "halogen" includes a fluorine atom, a chlorine atom, a bromine atom and an iodine atom. A fluorine atom and a chlorine atom are especially preferable.

The term "alkyl" includes a C1 to C15, preferably C1 to C10, more preferably C1 to C6 and further preferably C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

The term "alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

The term "alkylene" includes a C1 to C15, preferably a C1 to C10, more preferably a C1 to C6 and further preferably a C1 to C4 liner or branched bivalent hydrocarbon group. Examples include methylene, ethylene, trimethylene, propylene, tetramethylene, pentamethylene, hexamethylene and the like.

The term "alkenylene" includes a C2 to C15, preferably a C2 to C10, more preferably a C2 to C6 and further preferably a C2 to C4 liner or branched bivalent hydrocarbon having one or more double bond(s) at any position(s). Examples include vinylene, prenylene, butenylene, pentenylene and the like.

The term "hydroxyalkyl" means a group wherein one or more hydroxyl group(s) is replaced with hydrogen atom(s) attached to a carbon atom(s) of the above "alkyl". Examples include hydroxymethyl, 1-hydroxyethyl, 2-hydroxyethyl, 1-hydroxypropyl, 2-hydroxypropyl, 1,2-hydroxyethyl and the like.

A preferred embodiment of "hydroxyalkyl" is hydroxymethyl.

The term "alkyloxy" means a group wherein the above "alkyl" is bonded to an oxygen atom. Examples include methyloxy, ethyloxy, n-propyloxy, isopropyloxy, n-butyloxy, tert-butyloxy, isobutyloxy, sec-butyloxy, pentyloxy, isopentyloxy, hexyloxy and the like.

A preferred embodiment of "alkyloxy" is methyloxy, ethyloxy, n-propyloxy, isopropyloxy or tert-butyloxy.

The term "haloalkyl" means a group wherein one or more "halogen" described above is bonded to the above "alkyl". Examples include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl and the like.

A preferred embodiment of "haloalkyl" is trifluoromethyl or trichloromethyl.

The term "alkylcarbonyl" means a group wherein the above "alkyl" is bonded to a carbonyl group. Examples include methylcarbonyl, ethylcarbonyl, propylcarbonyl, isopropylcarbonyl, tert-butylcarbonyl, isobutylcarbonyl, sec-butylcarbonyl, penthylcarbonyl, isopenthylcarbonyl, hexylcarbonyl and the like.

A preferred embodiment of "alkylcarbonyl" is methylcarbonyl, ethylcarbonyl or n-propylcarbonyl.

The term "alkylamino" means a group wherein one or two hydrogen atom(s) attached to a nitrogen atom of an amino group is replaced with the above "alkyl". Two alkyl groups may be the same or different. Examples include methylamino, ethylamino, isopropylamino, dimethylamino, diethylamino, N,N-diisopropylamino, N-methyl-N-ethylamino, N-isopropyl-N-ethylamino and the like.

A preferred embodiment of "alkylamino" is methylamino, ethylamino, dimethylamino or diethylamino.

The term "alkylaminoalkyl" means a group wherein the above "alkylamino" is bonded to the above "alkyl".

The term "alkylaminocarbonyl" means a group wherein the above "alkylamino" is bonded to a carbonyl group.

The term "alkylaminocarbonyloxy" means a group wherein the above "alkylaminocarbonyl" is bonded to an oxygen atom.

The term "alkylcarbonylamino" means a group wherein the above "alkylcarbonyl" is replaced with a hydrogen atom bonded to a nitrogen atom of an amino group. Examples include methylcarbonylamino, ethylcarbonylamino, propylcarbonylamino, isopropylcarbonylamino, tert-butylcarbonylamino, isobutylcarbonylamino, sec-butylcarbonylamino and the like.

A preferred embodiment of "alkylcarbonylamino" is methylcarbonylamino or ethylcarbonylamino.

The term "alkylcarbonyloxy" means a group wherein the above "alkylcarbonyl" is bonded to an oxygen atom. Examples include methylcarbonyloxy, ethylcarbonyloxy, propylcarbonyloxy, isopropylcarbonyloxy, tert-butylcarbonyloxy, isobutylcarbonyloxy, sec-butylcarbonyloxy and the like.

A preferred embodiment of "alkylcarbonyloxy" is methylcarbonyloxy or ethylcarbonyloxy.

The term "alkylcarbonylaminoalkyl" means a group wherein the above "alkylcarbonylamino" is bonded to the above "alkyl".

The term "alkyloxycarbonyl" means a group wherein the above "alkyloxy" is bonded to a carbonyl group. Examples include methyloxycarbonyl, ethyloxycarbonyl, propyloxycarbonyl, isopropyloxycarbonyl, tert-butyloxycarbonyl, isobutyloxycarbonyl, sec-butyloxycarbonyl, penthyloxycarbonyl, isopenthyloxycarbonyl, hexyloxycarbonyl and the like.

A preferred embodiment of "alkyloxycarbonyl" is methyloxycarbonyl, ethyloxycarbonyl or propyloxycarbonyl.

The term "alkyloxycarbonylalkyl" means a group wherein the above "alkyloxycarbonyl" is bonded to the above "alkyl".

The term "alkyloxycarbonyloxy" means a group wherein the above "alkyloxycarbonyl" is bonded to an oxygen atom.

The term "alkylsulfanyl" means a group wherein the above "alkyl" is replaced with a hydrogen atom bonded to a sulfur atom of a sulfanyl group. Examples include methylsulfanyl, ethylsulfanyl, n-propylsulfanyl, isopropylsulfanyl and the like.

The term "alkylsulfonyl" means a group wherein the above "alkyl" is bonded to a sulfonyl group. Examples include methylsulfonyl, ethylsulfonyl, propylsulfonyl, isopropylsulfonyl, tert-butylsulfonyl, isobutylsulfonyl, sec-butylsulfonyl and the like.

A preferred embodiment of "alkylsulfonyl" is methylsulfonyl or ethylsulfonyl.

The term "trialkylsilyl" means a group wherein three of the above "alkyl" are bonded to a silicon atom. Three alkyl groups may be the same or different. Examples include trimethylsilyl, triethylsilyl, tert-butyldimethylsilyl and the like.

The term "carbocyclyl group" means C3 to C20 preferably C3 to C16, more preferably C4 to C12 cyclic hydrocarbon group and includes aromatic carbocyclyl and non-aromatic carbocyclyl.

The term "aromatic carbocyclyl" means a cyclic aromatic hydrocarbon group which is monocyclic or polycyclic having two or more rings. Examples include phenyl, naphthyl, anthryl, phenanthryl and the like.

A preferred embodiment of "aromatic carbocyclyl" is phenyl, 1-naphthyl or 2-naphthyl. Another embodiment of "aromatic carbocyclyl" is phenyl, The term "non-aromatic carbocyclyl" means a cyclic saturated hydrocarbon group or a cyclic unsaturated non-aromatic hydrocarbon group, which is monocyclic or polycyclic having two or more rings. Examples of the "non-aromatic carbocyclyl", which is polycyclic having two or more rings, include a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

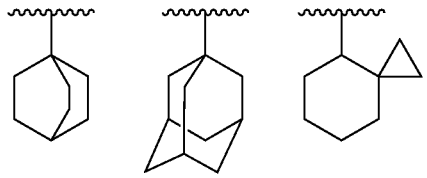 [SMILES: *C12CCC(CC1)CC2 ; *C12CC3CC(CC(C3)C1)C2 ; *C1CCCCC12CC2]

The non-aromatic carbocyclyl which is monocyclic is preferably C3 to C16, more preferably C3 to C12 and further preferably C3 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

Examples of non-aromatic carbocyclyl, which is polycyclic having two or more rings, include indanyl, indenyl, acenaphthyl, tetrahydronaphthyl, fluorenyl and the like.

The term "carbocycle" means C3 to C20 preferably C3 to C16, more preferably C4 to C12 cyclic hydrocarbon and includes aromatic carbocycle and non-aromatic carbocycle.

The term "aromatic carbocycle" means a cyclic aromatic hydrocarbon which is monocyclic or polycyclic having two or more rings. Examples include benzene ring, naphthalene ring, anthracene ring, phenanthrene ring and the like.

A preferred embodiment of "aromatic carbocycle" is benzene ring and naphthalene ring are exemplified. Another embodiment of "aromatic carbocycle" is benzene ring.

The term of "non-aromatic carbocycle" means a saturated carbocycle or an unsaturated non-aromatic carbocycle which is monocyclic or polycyclic having two or more rings. Examples of the "non-aromatic carbocycle" which is polycyclic having two or more rings, include a fused ring wherein a non-aromatic carbocycle, which is monocyclic or polycyclic having two or more rings, is fused with a ring of the above "aromatic carbocycle".

In addition, examples of the "non-aromatic carbocycle" also include a cycle having a bridge or a cycle to form a spiro ring as follows:

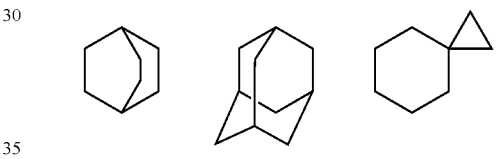

The non-aromatic carbocycle which is monocyclic is preferably C3 to C16, more preferably C3 to C12 and further preferably C3 to C8 carbocycle. Examples include cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene and the like.

Examples of non-aromatic carbocycle, which is polycyclic having two or more rings, include indane, indene, acenaphthalene, tetrahydronaphthalene, fluorine and the like are exemplified.

The term "heterocyclyl group" includes an aromatic cyclyl and a non-aromatic heterocyclyl, which is containing one or more of heteroatom(s) selected independently from O, S and N.

The term "aromatic heterocyclyl" means an aromatic cyclyl, which is monocyclic or polycyclic having two or more rings, containing one or more of heteroatom(s) selected independently from O, S and N. Examples of "aromatic heterocyclyl", which is polycyclic having two or more rings, include a fused ring group wherein an aromatic heterocyclyl, which is monocyclic or polycyclic having two or more rings, is fused with a ring of the above "aromatic carbocyclyl".

The aromatic heterocyclyl, which is monocyclic, is preferably a 5- to 8-membered and more preferably 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

Examples of aromatic heterocyclyl, which is polycyclic having three or more rings, include carbazolyl, acridinyl, xanthenyl, phenothiazinyl, phenoxathiinyl, phenoxazinyl, dibenzofuryl and the like.

The term "non-aromatic heterocyclyl" means a non-aromatic cyclyl, which is monocyclic or polycyclic having two or more rings, containing one or more heteroatom(s) selected independently from O, S and N. Examples of "non-aromatic heterocyclyl", which is polycyclic having two or more rings, include a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl".

In addition, examples of the "non-aromatic heterocyclyl" also include a group having a bridge or a group to form a spiro ring as follows:

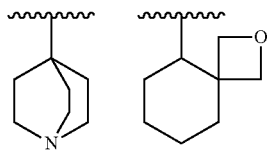

The non-aromatic heterocyclyl, which is monocyclic, is preferably a 3- to 8-membered and more preferably 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridinyl, tetrahydropyridinyl, tetrahydrofuryl, tetrahydropyranyl, dihydrothiazolinyl, tetrahydrothiazolinyl, tetrahydroisothiazolinyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like.

Examples of non-aromatic heterocyclyl, which is polycyclic having two or more rings, include indolinyl, isoindolinyl, chromanyl, isochromanyl and the like.

The term "heterocycle" includes an aromatic cycle and a non-aromatic heterocycle, which is containing one or more of heteroatom(s) selected independently from O, S and N.

The term of "aromatic heterocycle" means an aromatic cycle which is monocyclic or polycyclic having two or more rings, containing one or more of heteroatom(s) selected independently from O, S and N. Examples of "aromatic heterocycle", which is polycyclic having two or more rings, include a fused ring wherein an aromatic heterocycle, which is monocyclic or polycyclic having two or more rings, is fused with a ring of the above "aromatic carbocycle".

The aromatic heterocycle, which is monocyclic, is preferably a 5- to 8-membered and more preferably 5- to 6-membered ring. Examples include pyrrole, imidazole, pyrazole, pyridine, pyridazine, pyrimidine, pyrazine, triazole, triazine, tetrazole, furan, thiophene, isoxazole, oxazole, oxadiazole, isothiazole, thiazole, thiadiazole and the like.

Examples of aromatic heterocycle, which is bicyclic, include indoline, isoindoline, indazorin, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, thiazolopyridine and the like.

Examples of aromatic heterocycle, which is polycyclic having three or more rings, include carbazole, acridine, xanthene, phenothiazine, phenoxathiin, phenoxazine, dibenzofuran and the like.

The term "non-aromatic heterocycle" means a non-aromatic cycle, which is monocyclic or polycyclic having two or more rings, containing one or more of heteroatom(s) selected independently from O, S and N. Examples of "non-aromatic heterocycle", which is polycyclic having two or more rings, include a fused ling wherein a non-aromatic heterocycle, which is monocyclic or polycyclic having two or more ring(s), is fused with a ring of the above "aromatic carbocycle", "non-aromatic carbocycle" and/or "aromatic heterocycle".

In addition, examples of "non-aromatic heterocycle" also include a cycle having a bridge or a cycle to form a spiro ring as follows:

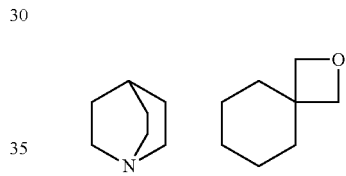

The non-aromatic heterocycle, which is monocyclic, is preferably a 3- to 8-membered and more preferably 5- to 6-membered ring. Examples include dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazoline, tetrahydrothiazoline, tetrahydroisothiazoline, dihydrooxazine, hexahydroazepine, tetrahydrodiazepine, tetrahydropyridazine, hexahydropyrimidine, dioxolane, dioxazine, aziridine, dioxoline, oxepane, thiolane, thiazine and the like.

Examples of non-aromatic heterocycle, which is polycyclic having two or more rings, include indoline, isoindoline, chroman, isochroman and the like.

The "carbocycle" part of "carbocyclylalkyl", "carbocyclyloxy" or "carbocyclylamino" is same as the above "carbocycle".

The "heterocycle" part of "heterocyclylalkyl", "heterocyclyloxy" or "heterocyclylamino" is same as the above "heterocycle".

The present invention is characterized in that the compound isolated by optical resolution of tricyclic compounds substituted by the other tricyclic group improves cap-dependent endonuclease inhibitory activity.

The present invention is also characterized in that the present compound is efficiently absorbed into the body after administration (for example, oral administration), and showing high high efficacy by introducing a group $P^R$ to form a prodrug.

One or more hydrogen, carbon and/or other atoms in the compounds of the present invention may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds of the present invention include compounds replaced with these isotopes. The compounds replaced with the above isotopes are useful as medicines and include all of radiolabeled compounds of the compound of the present invention. A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the present invention can be prepared using well-known methods in this field of the invention. For example, a tritium-labeled compound of the present invention can be prepared by introducing a tritium to a certain compound of the present invention, through a catalytic dehalogenation reaction using a tritium. This method comprises reacting with an appropriately-halogenated precursor of the compound of the present invention with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds of the present invention include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds of the present invention or its pharmaceutically acceptable salts may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds of the present invention. When the compounds of the present invention or its pharmaceutically acceptable salts are allowed to stand in the atmosphere, the compounds may absorb water, resulting in attachment of adsorbed water or formation of hydrates. Recrystallization of the compounds of the present invention or its pharmaceutically acceptable salts may produce crystal polymorphs.

$P^R$ group is preferably a group converted into OH group by action of drug-metabolizing enzymes, hydrolases, gastric acids, and/or enterobacteria, after in vivo administration (for example, oral administration).

Examples of more preferred embodiment of $P^R$ include a group selected from the following formulae a) to ac).

a) —C(=O)—$P^{R0}$,
b) —C(=O)—$P^{R1}$,
c) —C(=O)-L-$P^{R1}$,
d) —C(=O)-L-O—$P^{R1}$,
e) —C(=O)-L-O-L-O—$P^{R1}$,
f) —C(=O)-L-O—C(=O)—$P^{R1}$,
g) —C(=O)—O—$P^{R2}$,
h) —C(=O)—N(—K)($P^{R2}$),
i) —C(=O)—O-L-O—$P^{R2}$,
j) —C($P^{R3}$)$_2$—O—$P^{R4}$,
k) —C($P^{R3}$)$_2$—O-L-O—$P^{R4}$,
l) —C($P^{R3}$)$_2$—O—C(=O)—$P^{R4}$,
m) —C($P^{R3}$)$_2$—O—C(=O)—O—$P^{R4}$,
n) —C($P^{R3}$)$_2$—O—C(=O)—N(—K)—$P^{R4}$,
o) —C($P^{R3}$)$_2$—O—C(=O)—O-L-O—$P^{R4}$,
p) —C($P^{R3}$)$_2$—O—C(=O)—O-L-N($P^{R4}$)$_2$,
q) —C($P^{R3}$)$_2$—O—C(=O)—N(—K)-L-O—$P^{R4}$,
r) —C($P^{R3}$)$_2$—O—C(=O)—N(—K)-L-N($P^{R4}$)$_2$,
s) —C($P^{R3}$)$_2$—O—C(=O)—O-L-O-L-O—$P^{R4}$,
t) —C($P^{R3}$)$_2$—O—C(=O)—O-L-N(—K)—C(=O)—$P^{R4}$,
u) —C($P^{R3}$)$_2$—O—P(=O)(—$P^{R5}$)$_2$,
v) —C($P^{R3}$)$_2$—$P^{R6}$ (except for a benzyl group),
w) —C(=N$^+$($P^{R7}$)$_2$)(—N($P^{R7}$)$_2$),
x) —C($P^{R3}$)$_2$—C($P^{R3}$)$_2$—C(=O)—O—$P^{R2}$,
y) —C($P^{R3}$)$_2$—N(—K)—C(=O)—O—$P^{R2}$,
z) —P(=O)(—$P^{R8}$)(—$P^{R9}$),
aa) —S(=O)$_2$—$P^{R10}$,
ab) —$P^{R11}$, and
ac) —C($P^{R3}$)$_2$—C($P^{R3}$)$_2$—O—$P^{R2}$, wherein L is straight or branched alkylene, or straight or branched alkenylene;

K is hydrogen, or alkyl optionally substituted by substituent group A;

$P^{R0}$ is alkyl optionally substituted by substituent group A, or alkenyl optionally substituted by substituent group A;

$P^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;

$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl optionally substituted by substituent group A;

$P^{R3}$ is each independently hydrogen or alkyl;

$P^{R4}$ is each independently alkyl optionally substituted by substituent group A, carbocyclyl group optionally substituted by substituent group A, heterocyclyl group optionally substituted by substituent group A, alkyl amino optionally substituted by substituent group A, carbocyclylalkyl optionally substituted by substituent group A, heterocyclylalkyl optionally substituted by substituent group A, or trialkylsilyl;

$P^{R5}$ is each independently hydroxy or OBn;

$P^{R6}$ is carbocyclyl group optionally substituted by substituent group A, or heterocyclyl group optionally substituted by substituent group A;

$P^{R7}$ is each independently alkyl optionally substituted by substituent group A;

$P^{R8}$ is alkyloxy optionally substituted by substituent group A;

$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A;

$P^{R8}$ and $P^{R9}$ may be taken together with an adjacent phosphorus atom to form heterocycle optionally substituted by substituent group A;

$P^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A;

$P^{R11}$ is alkyl optionally substituted by substituent group A, alkenyl optionally substituted by substituent group A, carbocyclyl group optionally substituted by substituent group A, or heterocyclyl group optionally substituted by substituent group A.

Substituent group A; oxo, alkyl, hydroxyalkyl, amino, alkylamino, carbocyclyl, heterocyclyl, carbocyclylalkyl, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho.

Examples of further preferred embodiment of $P^R$ include following groups.

a) —C(=O)—$P^{R0}$,
b) —C(=O)—$P^{R1}$,
g) —C(=O)—O—$P^{R2}$,
h) —C(=O)—N(—K)($P^{R2}$),
i) —C(=O)—O-L-O—$P^{R2}$,
l) —C($P^{R3}$)$_2$—O—C(=O)—$P^{R4}$,
m) —C($P^{R3}$)$_2$O—C(=O)—O$P^{R4}$,
o) —C($P^{R3}$)$_2$—O—C(=O)—O-L-O—$P^{R4}$,
v) —C($P^{R3}$)$_2$—$P^{R6}$ (except for a benzyl group),
x) —C($P^{R3}$)$_2$—C($P^{R3}$)$_2$—C(=O)—O—$P^{R2}$,
y) —C($P^{R3}$)$_2$—N(—K)—C(=O)—O—$P^{R2}$, and
z) —P(=O)(—$P^{R8}$)(—$P^{R9}$), wherein L is straight or branched alkylene;
K is hydrogen, or alkyl optionally substituted by substituent group A;
$P^{R0}$ is alkyl optionally substituted by substituent group A;
$P^{R1}$ is carbocyclyl group optionally substituted by substituent group A, or heterocyclyl group optionally substituted by substituent group A;
$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, or heterocyclylalkyl optionally substituted by substituent group A;
$P^{R3}$ is each independently hydrogen or alkyl;
$P^{R4}$ is alkyl optionally substituted by substituent group A, carbocyclyl group optionally substituted by substituent group A, or heterocyclyl group optionally substituted by substituent group A;
$P^{R6}$ is carbocyclyl group optionally substituted by substituent group A, or heterocyclyl group optionally substituted by substituent group A;
$P^{R8}$ is alkyloxy optionally substituted by substituent group A;

$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or beterocyclylamino optionally substituted by substituent group A; and $P^{R8}$ and $P^{R9}$ may be taken together with an adjacent phosphorus atom to form heterocycle optionally substituted by substituent group A.

Substituent group A; oxo, alkyl, alkylamino, carbocyclyl, heterocyclyl, alkylcarbonyl, halogen, hydroxy, alkylcarbonylamino, alkylcarbonyloxy, alkyloxycarbonyl, alkyloxycarbonylalkyl, alkylaminocarbonyloxy, alkyloxy, nitro, azido, alkylsulfonyl and trialkylsilyl.

Examples of another embodiment of a preferable substituent of $P^R$ include following groups.

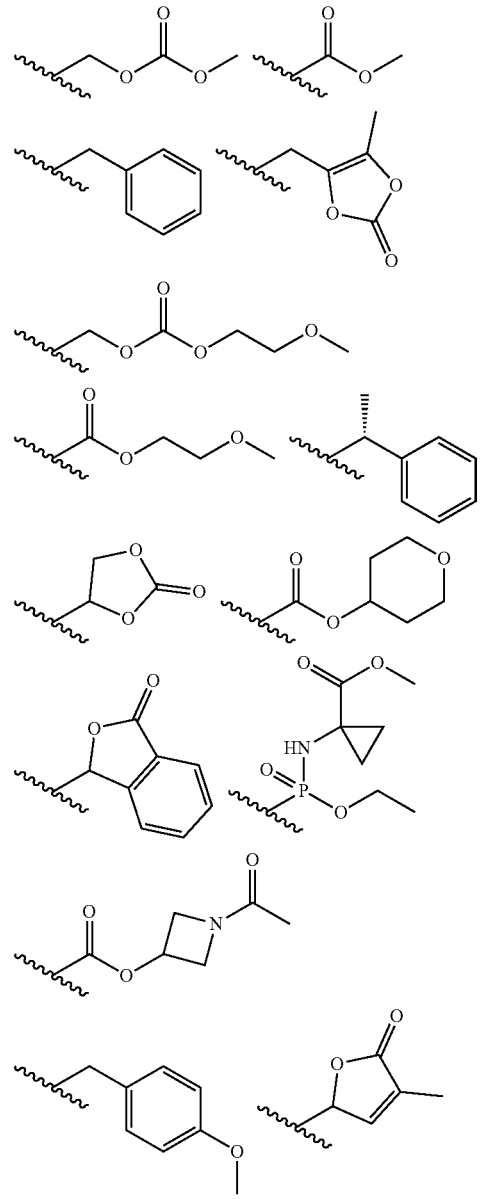

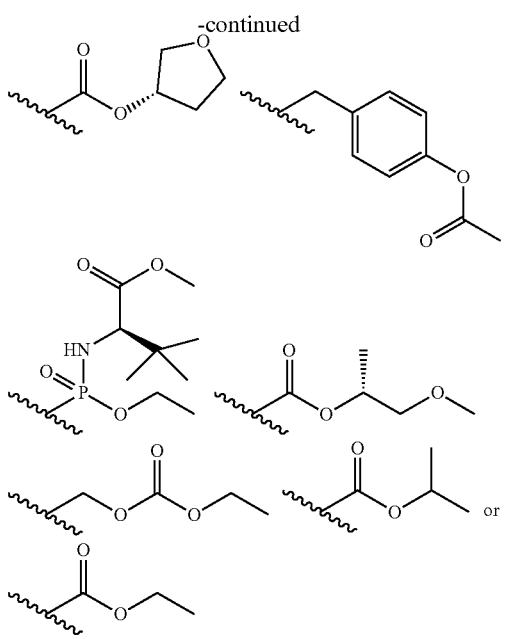

(Method for Producing Compound of the Present Invention)

A general method for producing the compound of the present invention will be exemplified below. As to the extraction and purification, treatment which is performed in a normal experiment of organic chemistry may be conducted.

Synthesis of the compound of the present invention can be carried out referring to the procedures known in the art.

As a raw material compound, commercially available compounds, compounds described in the present description, compounds described in the references cited in the present description, and other known compounds can be utilized.

When one wants to obtain a salt of the compound of the present invention, in the case where the compound of the present invention is obtained in a form of a salt, it may be purified as it is and, in the case where the compound of the present invention is obtained in a free form, a salt may be formed by a normal method by dissolving or suspending the compound in a suitable organic solvent, and adding an acid or a base.

In addition, the compound of the present invention and a pharmaceutically acceptable salt thereof are present in a form of adducts with water or various solvents (hydrate or solvate) in some cases, and these adducts are included in the present invention.

In a general synthesis method as well as Reference examples, Examples, and Intermediate Synthesis Examples, the meaning of each abbreviation is as follows.

Boc: tert-butoxycarbonyl
DBU: diazabicycloundecene
DMA: N,N-dimethylacet amide
DMF: N,N-dimethylformamide
HATU: O-(7-azabenzotriazol-1-yl)-N,N,N',N'-tetramethyluronium hexafluorophosphate
NMP: N-methylpyrrolidone
OBn: benzyloxy
THF: tetrahydrofuran
T3P: propyl phoshonic anhydride
WSC.HCl: N-ethyl-N'-(3-dimethylaminopropyl)carbodiimide hydrochloride The up and down of the "wedge" and "broken line wedge" indicates the absolute configuration.

(Preparation 1)

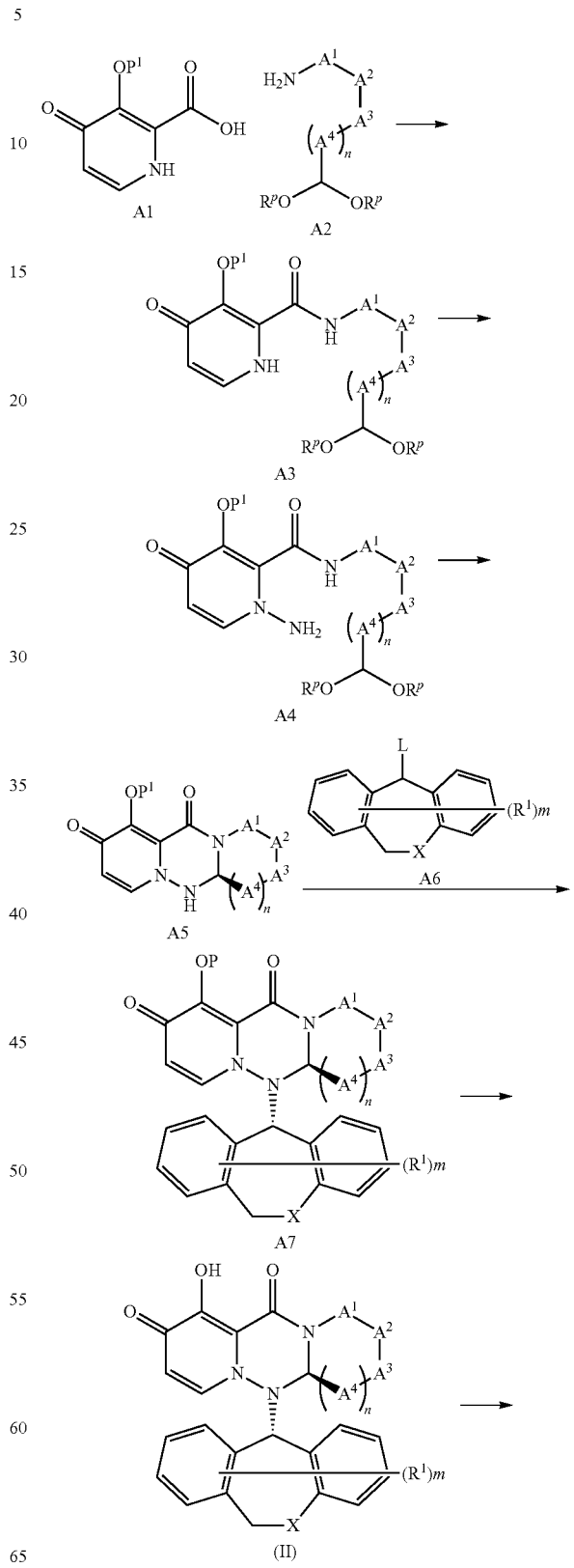

-continued

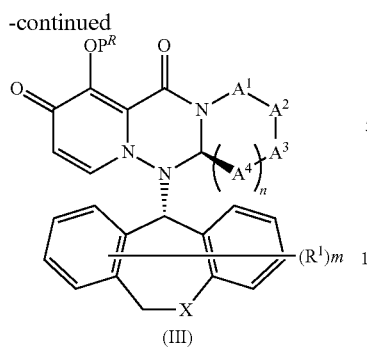

(III)

wherein $P^1$ is hydroxyl protective group; $R^P$ is acetal protective group; L is leaving group; Other each symbol is same as above.

First Step

Compound A3 can be obtained by adding Compound A2 to Compound A1 in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU, etc. in a solvent such as DMF, THF, dichloromethane, acetonitrile etc. or in a mixed solvent thereof, and performing a reaction at −20° C. to 60° C., preferably −10° C. to 40° C. for 0.1 hours to 24 hours, preferably 1 hour to 12 hours.

Alternatively, Compound A3 can be obtained by adding an acylating reagent such as diphenylchlorophosphate, thionyl chloride, oxalyl chloride etc. to Compound A1 in the presence or absence of a base such as pyridine, triethylamine, diisopropylethylamine, 1-methylimidazole, etc. in the presence of a solvent such as THF, dioxane, dichloromethane, DMF etc., thereby, generating acid chloride, and adding Compound A2 having a substituent corresponding to an objective compound, and performing a reaction at −20° C. to 60° C., preferably −10° C. to 40° C. for 0.1 hours to 24 hours, preferably 0.5 hours to 12 hours.

Second Step

Compound A4 can be obtained by adding potassium carbonate, sodium carbonate, and O-(2,4-dinitrophenyl)hydroxylamine to Compound A3 in the presence of a solvent such as DMF, DMA, NMP, THF, etc., and performing a reaction at 10° C. to 60° C., preferably 20° C. to 40° C. for 0.1 hours to 48 hours, preferably 1 hour to 24 hours.

Third Step

A deprotecting reaction of an acetal protective group of Compound A4 can be performed by the general method described in Protective Groups in Organic Synthesis, Theodora W Green (John Wiley & Sons) etc. Thereafter, a generated aldehyde group is subjected to an intramolecular reaction, thereby, Compound A5 can be obtained.

For example, racemate of Compound A5 can be obtained by adding acetic acid and/or paratoluenesulfonic acid, metanesulfonic acid etc., to Compound A4 in the presence of a solvent such as DMF, toluene, THF, etc., and performing a reaction at 10° C. to 80° C., preferably 30° C. to 60° C. for 0.5 hours to 12 hours, preferably 1 hour to 6 hours. Compound A5 can be obtained by optical resolution of the racemate of Compound A5 by SFC or HPLC (chiral column).

Fourth Step

Compound A7 can be obtained by adding Compound A6, and a base such as sodium carbonate, potassium carbonate, cesium carbonate, etc. to Compound A5 in the presence of a solvent such as DMF, DMA, NMP, THF, etc. or in a mixed solvent thereof, and performing a reaction at 0° C. to 60° C., preferably 10° C. to 40° C. for 0.1 hours to 48 hours, preferably 1 hour to 24 hours.

Alternatively, Compound A7 can be obtained by adding Compound A6, and T3P, methane sulfonic acid or paratoluene sulfonic acid to Compound A5 in the presence of a solvent such as DMF, ethyl acetate, butyl acetate, 1,4-dioxane etc. or in a mixed solvent thereof, and performing a reaction at 40° C. to 150° C., preferably 60° C. to 120° C. for 0.1 hours to 48 hours, preferably 1 hour to 24 hours.

Fifth Step

A deprotecting reaction of hydroxyl protective group of Compound A7 can be performed by the general method described in Protective Groups in Organic Synthesis, Theodora W Green (John Wiley & Sons) etc.

Sixth Step

Compound (III) can be obtained by the general method including converting a hydroxyl group of Compound (II) into an ester group or ether group.

For example, the method described in Protective Groups in Organic Synthesis, Theodora W Green (John Wiley & Sons), Prog. Med. 5: 2157-2161 (1985), and Supplied by The British Library—"The world's Knowledge", etc. can be utilized.

(Preparation 2)

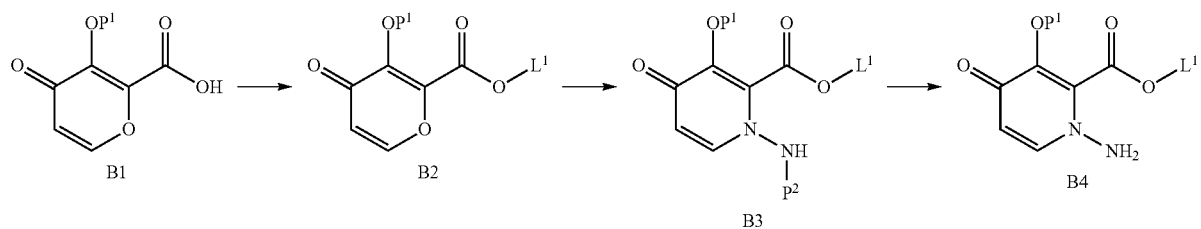

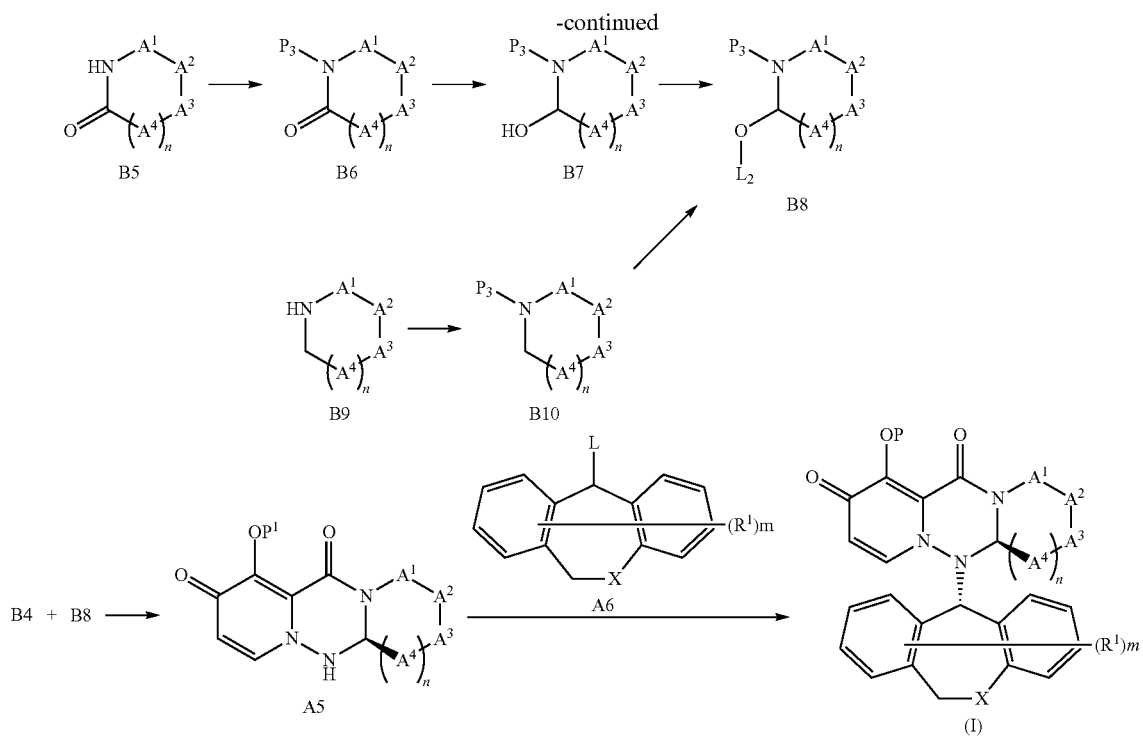

wherein $P^2$ is NH protective group; $L^1$ and $L^2$ is leaving group; Other each symbol is same as above.

First Step

Compound B2 can be obtained by adding Compound A2 and halogenated alkyl such as methyl iodide to Compound B1 in the presence of a base such as diazabicycloundecene in a solvent such as DMF, THF, dichloromethane, acetonitrile, etc. or in a mixed solvent thereof, and performing a reaction at −20° C. to 60° C., preferably −10° C. to 40° C. for 0.1 hours to 24 hours, preferably 1 hour to 24 hours.

Alternatively, Compound B2 can be obtained by adding acylating reagent such as diphenylchlorophosphate, thionyl chloride, oxalyl chloride, etc. to Compound B1 in a solvent such as THF, dioxane, dichloromethane, DMF, etc. or in a mixed solvent thereof, and adding alcohol in the presence of a base such as pyridine, triethylamine, diisopropylethylamine, 1-methylimidazole, etc., and performing a reaction at −20° C. to 60° C., preferably −10° C. to 40° C. for 0.1 hours to 24 hours, preferably 0.5 hours to 12 hours.

Second Step

Compound B3 can be obtained by adding para-toluene sulfonic acid pyridinium and hydrazine protected by Boc etc. to Compound B2 in a solvent such as THF, dioxane, dichloromethane, DMF etc., or in a mixed solvent thereof, and performing a reaction at 10° C. to 150° C., preferably 40° C. to 100° C. for 1 hour to 48 hours, preferably 1 hour to 24 hours.

Third Step

A deprotecting reaction of amino protective group Compound B3 can be performed by the general method described in Protective Groups in Organic Synthesis, Theodora W Green (John Wiley & Sons) etc.

Fourth Step

Compound B6 can be obtained by adding a base such as n-butyl lithium, etc. to Compound B5 in a solvent such as THF, dioxane, dichloromethane, DMF etc. or in a mixed solvent thereof, and then adding haloformic acid alkyl and performing a reaction for 0.1 hours to 48 hours, preferably 1 hour to 24 hours.

Fifth Step

Compound B7 can be obtained by adding reducing agent such as Lithium diisobutylaluminum hydride, etc. to Compound B6 in a solvent such as THF, dioxane, dichloromethane, DMF etc., or in a mixed solvent thereof, and performing a reaction for 0.1 hours to 48 hours, preferably 1 hour to 24 hours.

Sixth Step

Compound B8 can be obtained by adding para-toluene sulfonic acid or methane sulfonic acid to Compound B7 in alcohol, and performing a reaction at 0° C. to 100° C. for 0.1 hours to 48 hours, preferably 1 hour to 24 hours.

Seventh Step

Compound B10 can be obtained by adding haloformic acid alkyl to Compound B9 in the presence or absence of a base such as pyridine, triethylamine, diisopropylethylamine, 1-methylimidazole, etc., in a solvent such as THF, dioxane, dichloromethane, DMF etc., or in a mixed solvent thereof, and performing a reaction at −40° C. to 40° C. for 0.1 hours to 48 hours, preferably 1 hour to 24 hours.

Eighth Step

Compound B8 can be obtained by immersing carbon electrode (anode) and platinum electrode (cathode) to Compound B10 in a solvent such as alcohol in the presence of a base such as potassium carbonate and tetraethylaminium perchlorate, and flushing with a constant current of 0.1~1.0 A with stirring for 0.1 hours to 48 hours, preferably 1 hour to 24 hours.

Ninth to Tenth Step

Compound (I) can be obtained from Compound B4 and B8 in the same manner as in the third to sixth steps in preparation 1.

The compound of the present invention has cap-dependent endonuclease inhibitory activity and is useful as a therapeutic or preventive agent for influenza.

The compound of the present invention not only has cap-dependent endonuclease inhibitory activity but also is useful as a medicine and has any or all of the following excellent characteristics:
a) The compound is a weak inhibitor of CYP enzymes (e.g., CYP1A2, CYP2C9, CYP2C19, CYP2D6, CYP3A4 and the like).
b) The compound demonstrates good pharmacokinetics, such as a high bioavailability, moderate clearance and the like.
c) The compound has a high metabolic stability.
d) The compound has no irreversible inhibitory action against CYP enzymes (e.g., CYP3A4) when the concentration is within the range described in the present description as the measurement conditions.
e) The compound has no mutagenicity.
f) The compound is associated with a low cardiovascular risk.
g) The compound has a high solubility.
h) The compound has no phototoxicity.

For the purpose of treating the above-mentioned diseases in humans, the compounds of the present invention may be administered orally as a powder, a granule, tablets, capsules, pills, a liquid and the like or parenterally as an injection, suppositories, a percutaneous drug, an inhalant and the like. The effective doses of the present compounds may be mixed with excipients suitable for the dosage form, such as fillers, binders, humectants, disintegrators, and lubricants, as appropriate, to form pharmaceutical preparations. For preparing an injection, sterilization is performed with a suitable carrier.

The pharmaceutical compositions according to the present invention can be administered either orally or parenterally. For oral administration, commonly used dosage forms, such as tablets, granule, powder, and capsules, may be prepared according to conventional methods. For parenteral administration, any commonly used dosage form, such as an injection, may be suitably used. The compounds according to the present invention can be suitably used as oral preparations because of their high oral absorbability.

The effective doses of the compounds of the present invention can be mixed with various pharmaceutical excipients suitable for the dosage form, such as fillers, binders, disintegrators, and lubricants, as appropriate, to form pharmaceutical compositions.

The dose depends on the condition of the disease, administration route, or age or weight of the patient. The usual oral dose for adults is 0.1 to 100 mg/kg per day, preferably 1 to 20 mg/kg per day.

The dose of the pharmaceutical composition of the present invention is preferably determined on the basis of the age and weight of the patient, type and severity of the disease, administration route and the like. The usual oral dose for adults is in the range of 0.05 to 100 mg/kg per day, preferably 0.1 to 10 mg/kg per day. The parenteral dose for adults significantly varies depending on the administration route but is usually in the range of 0.005 to 10 mg/kg per day, preferably 0.01 to 1 mg/kg per day. The dose may be administered once daily or may be divided into multiple daily doses.

The compound of the present invention can be used in combination with other drugs or the like (hereinafter referred to as combination drugs) to increase the activity of the compound, reduce the dose of the compound, or the like. In the case of treating influenza, the compound can be used combined with or in a coupled formulation with neuraminidase inhibitor (e.g., Oseltamivir, Zanamivir, Peramivir, Inabiru and the like); RNA-dependent RNA polymerase inhibitor (e.g., Favipiravir); M2 protein inhibitor (e.g., Amantadine); PB2 Cap binding inhibitor (e.g., VX-787); anti-HA antibody (e.g., MHAA4549A); Immune agonists (e.g., Nitazoxanide) are also possible. In this case, the timing of administration for a compound of the present invention and the combination drug is not limited. They can be administered to the subjects to be treated, at a time or at different times. Furthermore, a compound of the present invention and the combination drug can be administered as two or more formulations independently comprising each active ingredient or a single formulation comprising each active ingredient.

The dose for combination drugs may be appropriately selected in reference to the clinical dose. The compounding ratio of the compounds of the present invention and co-administered drugs may be appropriately selected depending on the subject to be treated, administration route, disease to be treated, symptoms, combination of the drugs and the like. For administration in humans, for example, 1 part by weight of the compounds of the present invention may be used in combination with 0.01 to 100 parts by weight of co-administered drugs.

The present invention will be explained in more detail below by way of Examples, Reference examples, Intermediate Synthesis Examples, as well as Test Examples of the present invention, but the present invention is not limited by them.

The NMR analysis obtained in each reference example and example was carried out in 300 MHz, and was measured using DMSO-$d_6$, CDCl$_3$.

The term RT represents a retention time at LC/MS: liquid chromatography/mass spectrometry, and was measured under the following conditions.
(Measurement Conditions)
(1) Column: ACQUITY UPLC (Registered trademark) BEH C18 (1.7 μm i.d.2.1×50 mm) (Waters)
Flow rate: 0.8 mL/min
UV detection wavelength: 254 nm
Mobile phase: [A]: a 0.1% formic acid-containing aqueous solution, [B]: a 0.1% formic acid-containing acetonitrile solution
Gradient: a linear gradient of 5% to 100% solvent [B] was carried out in 3.5 minutes, and 100% solvent [B] was kept for 0.5 minutes.
(2) Column: Shim-pack XR-ODS (2.2 μm, i.d.50×3.0 mm) (Shimadzu)
Flow rate: 1.6 mL/min
UV detection wavelength: 254 nm
Mobile phase: [A]: a 0.1% formic acid-containing aqueous solution, [B]: a 0.1% formic acid-containing acetonitrile solution
Gradient: a linear gradient of 10% to 100% solvent [B] was carried out in 3 minutes, and 100% solvent [B] was kept for 0.5 minutes.

Reference Example 1

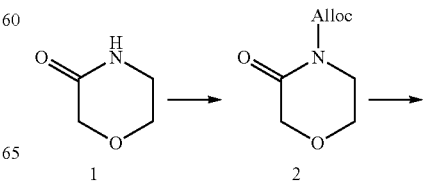

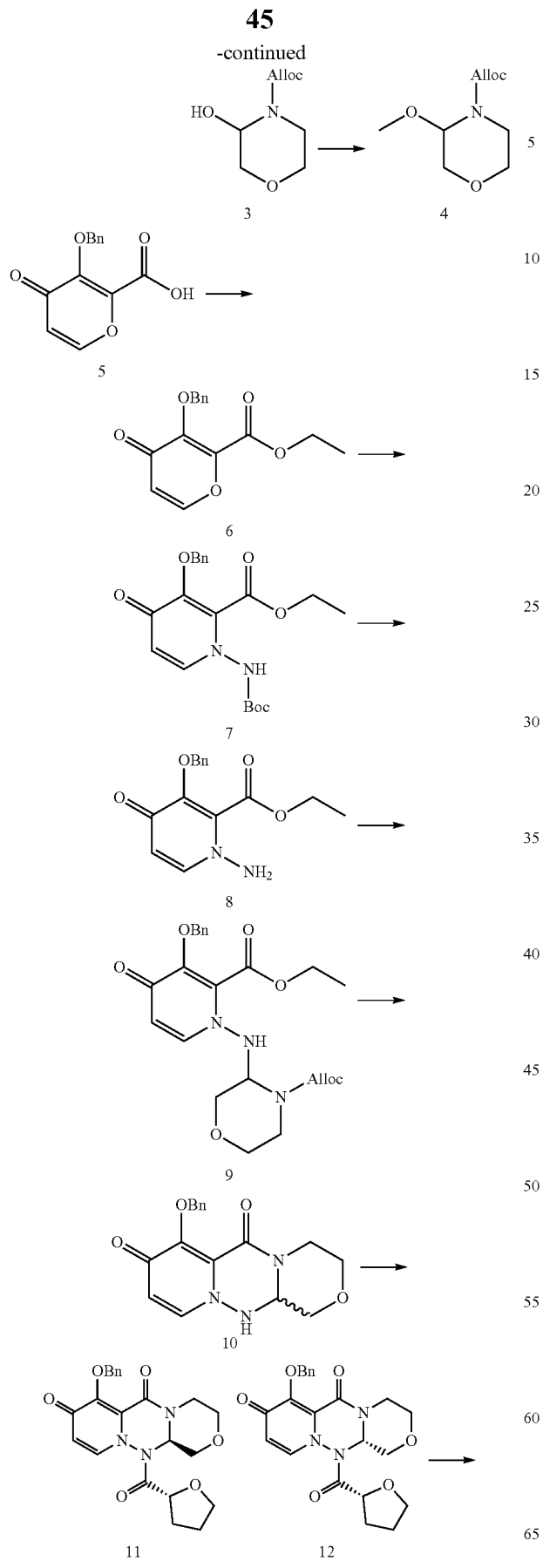
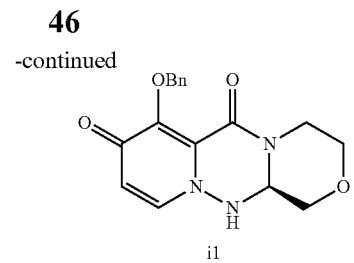

First Step

To a solution of Compound 1 (5.0 g, 49.5 mmol) in THF (100 mL) was added dropwise 1.62 mol/L n-butyllithium in hexane (30.5 mL, 49.5 mmol) at −78° C. under a nitrogen atmosphere, and the mixture was stirred at −78° C. for 2 hours. A solution of chloroformate allyl (5.96 g, 49.5 mmol) in THF (20 mL) was added dropwise thereto, and the mixture was stirred at −78° C. for 2 hours. The mixture was quenched with a saturated aqueous solution of ammonium chloride, warmed up to room temperature, and extracted with ethyl acetate. The obtained organic layer was washed with brine, dried over anhydrous magnesium sulfate, and concentrated under reduced pressure to obtain Compound 2 (5.66 g, 62%).

1H-NMR (CDCl3) δ: 3.83 (t, J=8.0 Hz, 2H), 3.92 (t, J=8.0 Hz, 2H), 4.26 (s, 2H), 4.78 (d, J=8.0 Hz, 2H), 5.30 (d, J=12.0 Hz, 1H), 5.44 (d, J=16.0 Hz, 1H), 5.93-6.03 (m, 1H),

Second Step

To a solution of Compound 2 (6.6 g, 35.6 mmol) in THF (66 mL) was added dropwise 1.03 mol/T, DIBAL-H in hexane (45.0 mL, 46.3 mmol), and the mixture was stirred at −78° C. for 1 hour. The mixture was quenched with acetone, an aqueous solution of Rochelle salt was added thereto. The mixture was stirred, and extracted with ethyl acetate. The obtained organic layer was washed with brine, dried over anhydrous magnesium sulfate, and concentrated under reduced pressure to obtain Compound 3 (6.21 g, 93%).

1H-NMR (CDCl3) δ: 3.44 (br, 1H), 3.50-3.64 (m, 2H), 3.71 (br, 1H), 3.95 (d, J=8.0 Hz, 2H), 4.64 (d, J=8.0 Hz, 2H), 5.24 (d, J=12.0 Hz, 1H), 5.40 (d, J=16.0 Hz, 1H), 5.47 (d, J=4 Hz, 1H), 5.87-6.00 (m, 1H)

Third Step

To a solution of Compound 3 (6.2 g, 33.1 mmol) in methanol (65 mL) was added p-Toluenesulfonic acid monohydrate (0.63 g, 3.31 mmol), and the mixture was stirred at room temperature over night. The mixture was quenched with an aqueous solution of sodium hydrogen carbonate, concentrated, and extracted with ethyl acetate. The obtained organic layer was washed with brine, dried over anhydrous magnesium sulfate, and concentrated under reduced pressure to obtain Compound 4 (5.77 g, 87%).

1H-NMR (CDCl3) δ: 3.34 (s, 3H), 3.55 (br, 2H), 3.73-3.99 (m, 3H), 4.64 (d, J=8.0 Hz, 2H), 5.10-5.20 (m, 1H), 5.25 (d, J=8.0 Hz, 1H), 5.33 (d, J=16 Hz, 1H), 5.8 8-6.05 (m, 1H)

Fourth Step

To a solution of Compound 5 (20.0 g, 81 mmol) in DMF (100 mL) were added ethyl iodide (22.8 g, 146 mmol) and diazabicycloundecene (18.4 mL, 122 mmol), and the mixture was stirred at room temperature over night. The mixture was poured into 10% aqueous solution of ammonium chloride, and extracted with ethyl acetate. The obtained organic layer was washed with brine, dried over anhydrous magnesium sulfate, and concentrated under reduced pressure to obtain Compound 6 (22.3 g, 100%).

1H-NMR (CDCl3) δ: 1.23 (t, J=8.0 Hz, 3H), 4.28 (q, J=8.0 Hz, 2H), 5.16 (s, 2H), 6.57 (d, J=4.0 Hz, 1H), 7.28-7.48 (m, 5H), 8.21 (d, J=4.0 Hz, 1H).

Fifth Step

To a solution of Compound 6 (500 mg, 1.82 mmol) in DMA (5.0 mL) were added pyridinium p-toluenesulfonate (1.37 g, 5.47 mmol) and Boc-hydrazine (361 mg, 2.74 mmol), and the mixture was stirred at 60° C. for 14 hours. To the mixture was added water and the mixture was extracted with ethyl acetate. The obtained organic layer was washed with a saturated aqueous solution of ammonium chloride and brine, dried over anhydrous magnesium sulfate, and concentrated under reduced pressure. The obtained residue was purified by silica gel column chromatography (chloroform-methanol) to obtain Compound 7 (519 mg, 73%).

1H-NMR (CDCl3) δ: 1.24 (t, J=8.0 Hz, 3H), 1.46 (s, 9H), 4.26 (q, J=8.0 Hz, 2H), 5.28 (s, 2H), 6.40 (d, J=8.0 Hz, 1H), 7.27-7.38 (m, 4H), 7.40-7.45 (m, 2H).

Sixth Step

Compound 7 (500 mg, 1.29 mmol) was dissolved in 4 mol/L hydrogen chloride in ethyl acetate (5 mL), and the mixture was stirred at room temperature for 1 hour. The mixture was concentrated under reduced pressure. To the obtained residue was added a saturated aqueous solution of sodium hydrogen carbonate, and the mixture was extracted with dichloromethane. The obtained organic layer was washed with brine, dried over anhydrous magnesium sulfate, and concentrated under reduced pressure to obtain Compound 8 (369 mg, 99%).

1H-NMR (CDCl3) δ: 1.26 (t, J=8.0 Hz, 3H), 4.31 (q, J=8.0 Hz, 2H), 5.24 (s, 2H), 6.47 (d, J=8.0, 1H), 7.28-7.44 (m, 5H), 7.64 (d, J=8.0, 1H).

Seventh Step

To a solution of Compound 8 (365 mg, 1.27 mmol) and Compound 4 (306 mg, 1.52 mmol) in acetonitrile (8 mL) was added dropwise tin chloride (0.223 mL, 1.90 mmol) at −25° C. under a nitrogen atmosphere, and the mixture was stirred at −25° C. for 45 minutes. The mixture was quenched with a saturated aqueous solution of sodium hydrogen carbonate, and dichloromethane was added thereto. The mixture was stirred at room temperature and filtered through Celite, and filtrate was extracted with dichloromethane. The obtained organic layer was washed with brine, dried over anhydrous magnesium sulfate, and concentrated under reduced pressure to obtain crude Compound 9. The obtained Compound 9 was dissolved in THF (8 mL), morpholine (1.10 mL, 12.7 mmol) and tetrakis(triphenylphosphine)palladium (146 mg, 0.127 mmol) were added thereto, and the mixture was stirred at room temperature for 2 hours. To the mixture was added diethyl ether (16 mL), and the precipitated solid was filtered and dried to obtain Compound 10 (418 mg, 100%).

1H-NMR (CDCl3) δ: 2.90-2.99 (m, 1H), 3.13 (t, J=12.0 Hz, 1H), 3.40-3.46 (m, 1H), 4.00-4.08 (m, 1H), 4.14 (d, J=12.0 Hz, 1H), 5.07 (s, 2H), 6.22 (d, J=8.0 Hz, 1H), 7.29-7.40 (m, 3H), 7.56 (d, J=8.0 Hz, 2H), 7.71 (d, J=8.0 Hz, 1H)

Eighth Step

To a suspension of (R)-2-Tetrahydrofurioic Acid (855 mg, 7.36 mmol) and Compound 10 (2.00 g, 6.11 mmol) in ethyl acetate (9 ml) were added pyridine (4.00 ml, 49.6 mmol) and T3P (50% in ethyl acetate, 11.0 ml, 18.5 mmol) at room temperature, and the mixture was stirred over night. The precipitated solid was filtered and washed with ethyl acetate (4 ml) and ethanol (4 ml). The obtained solid was suspended in ethanol (6 ml) and the suspension was stirred at room temperature for 6.5 hours. The suspension was filtered and the obtained solid was washed with ethanol (2 ml) twice to obtain Compound 11 (1.18 g, 45.4%).

¹H-NMR (DMSO) δ: 1.80-1.94 (m, 2H), 1.95-2.14 (m, 2H), 3.21-3.35-(m, 2H), 3.50-3.60 (m, 1H), 3.70-3.82 (m, 1H), 4.00-4.05 (m, 1H), 4.32-4.38 (m, 1H), 5.14 (dd, J=10.8 Hz 21.6 Hz, 2H), 5.76-5.81 (m, 1H), 6.29 (d; J=4.8 Hz, 1H), 7.28-7.39 (m, 3H), 7.48-7.54 (m, 2H), 7.64-7.75 (m, 1H)

Ninth Step

To a suspension of Compound 11 (500 mg, 1.18 mmol) in ethanol (3.5 ml) was added DBU (0.0035 ml, 0.023 mmol) at room temperature, and the mixture was stirred for 30 minutes. To the obtained suspension was added diisopropylether (6.5 ml), and the mixture was stirred at room temperature for 30 minutes. The precipitated solid was filtered and washed with ethyl acetate (1.5 ml) twice to obtain Compound i1 (346 mg, 89.9%).

¹H-NMR (DMSO) δ: 2.80-3.00 (m, 1H), 3.10-3.18 (m, 1H), 3.38-3.50 (m, 1H), 3.98-4.08 (m, 2H), 4.10-4.20 (m, 1H), 4.76-4.84 (m, 1H), 5.04-5.14 (m, 2H), 6.22 (m, J=7.6 Hz, 1H), 7.27-7.40 (m, 4H), 7.56-7.60 (m, 2H), 7.70 (d, J=7.6 Hz, 1H)

Reference Example 2

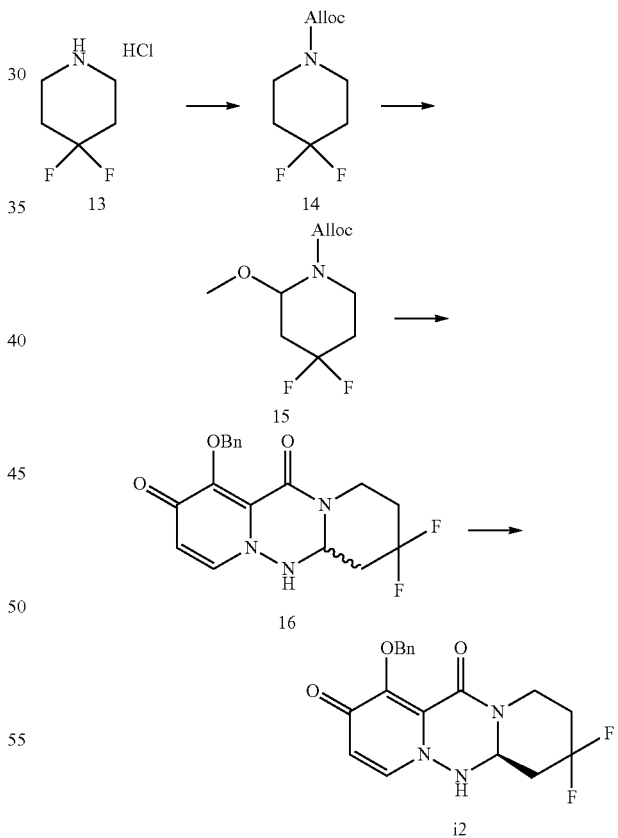

First Step

To a suspension of Compound 13 (8.0 g, 50.8 mmol) in dichloromethane (120 mL) was added triethylamine (17.6 mL, 127 mmol) under ice-water bath, and allyl chloroformate (6.44 mL, 60.9 mmol) was added dropwise thereto, and the mixture was stirred at 0° C. for 1 hour. To the mixture was added water, and the mixture was extracted with dichloromethane. The obtained organic layer was washed with 5% aqueous solution of citric acid and a saturated aqueous solution of sodium hydrogen carbonate, dried over anhydrous magnesium sulfate, and concentrated under reduced pressure to obtain Compound 14 (10.1 g, 97%).

1H-NMR (CDCl3) δ: 1.96 (br, 4H), 3.62 (s, 4H), 4.60 (s, 2H), 5.22 (d, J=12.0 Hz, 1H), 5.30 (d, J=16.0 Hz, 1H), 5.86-5.99 (m, 1H)

Second Step

To a solution of Compound 14 (0.9 g, 4.39 mmol), potassium carbonate (60 mg, 0.44 mmol) and tetraethylaminium-perchlorate (50 mg, 0.22 mmol) in methanol (30 mL) were immersed carbon electrode (anode) and platinum electrode (cathode), and the mixture was flushed with a constant current of 0.1 A with stirring at room temperature for 6 hours. To the mixture were added ethyl acetate and water, and the mixture was extracted with ethyl acetate. The obtained organic layer was dried over anhydrous magnesium sulfate, and concentrated under reduced pressure to obtain Compound 15 (992 mg, 96%).

1H-NMR (CDCl3) δ: 1.81-2.15 (m, 3H), 2.39 (t, J=12.0 Hz, 1H), 3.27 (s, 3H), 3.61 (s, 1H), 4.11 (br, 1H), 4.61 (br, 2H), 5.20-5.36 (m, 2H), 5.57 (br, 1H), 5.88-5.99 (m, 1H)

Third Step

Compound 16 was obtained in the same manner as in the seventh and eighth steps in reference example 1.

Fourth Step

The optical resolution of Compound 16 (870 mg, 2.41 mmol) by Waters SF C30 System (Daicel CHIRALPAK IB, liquefied carbon dioxide-methanol) gave Compound i2 (270 mg, 31%).

Analysis Condition

<Waters SFC30 System (SPRC4.5N406)>

Column: CHIRALPAK IB/SFC (5 μm, i.d.250×4.6 mm) (DAICEL)

Flow rate: 8.0 mL/min; UV detection wavelength: 254 nm

Back pressure: 100 bar

Mobile phase: [A]: liquefied carbon dioxide, [B]: methanol

Gradient: 5% solvent [B] was kept for 1 minute, a linear gradient of 5% to 40% solvent [B] was carried out in 6 minutes, 40% solvent [B] was kept for 2 minutes, and 5% solvent [B] was kept for 1 minute.

Elution time: 7.3 minutes

Reference Example 3

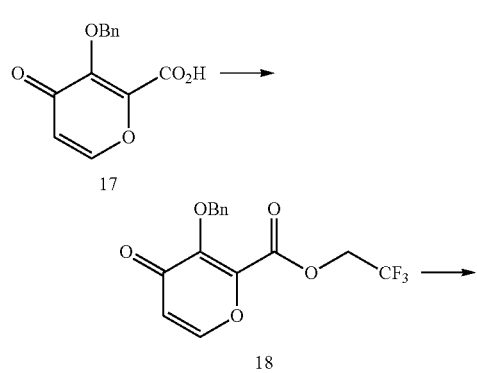

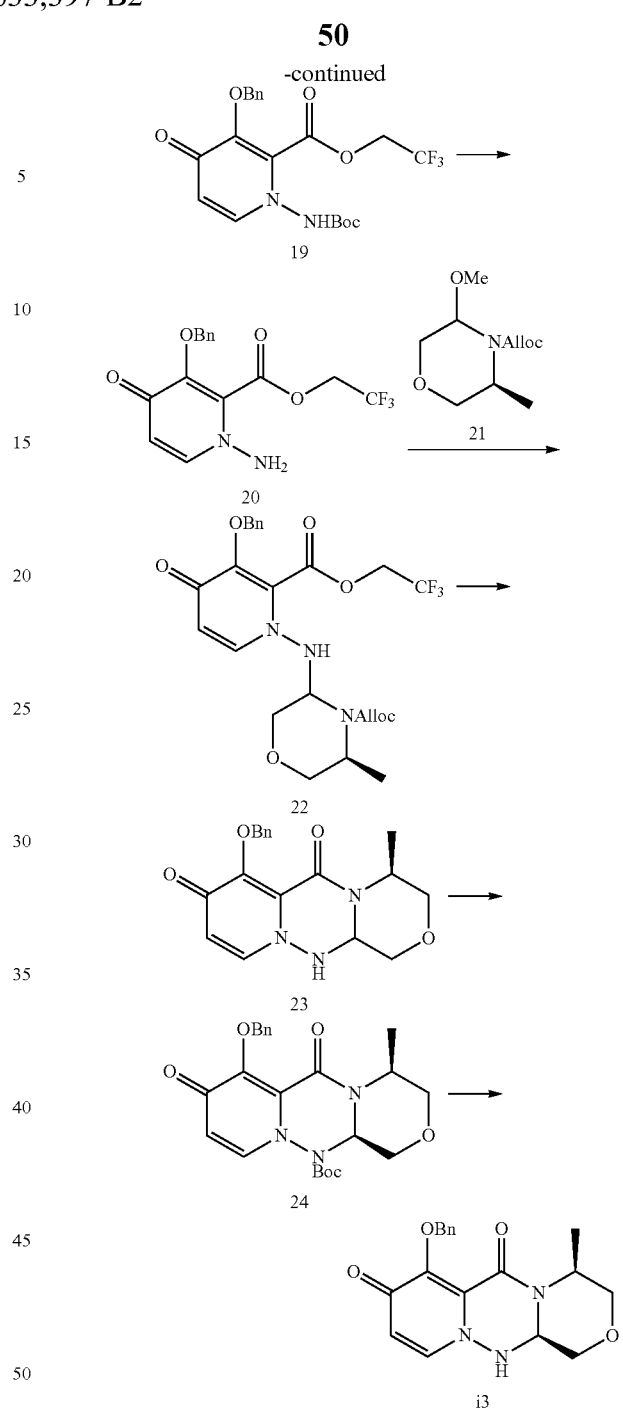

First Step

To a solution of Compound 17 (4.00 g, 16.3 mmol) in dichloromethane (40 mL) were added oxalyl dichloride (1.56 mL, 17.9 mmol) and DMF (0.013 mL, 0.162 mmol) under iced-bath, and the mixture was warmed up to room temperature and stirred for 5 hours. The mixture was concentrated under reduced pressure, and the obtained residue was dissolved in dichloromethane (40 mL), 2,2,2-trifluoroethanol (2.44 g, 24.4 mmol), triethylamine (4.50 mL, 32.5 mmol) and 4-(dimethylamino)pyridine (99.0 mg, 0.812 mmol) were added thereto under iced-bath, and the mixture was warmed up to room temperature and stirred for 1 hour. The mixture was concentrated under reduced pressure and to the obtained residue was added 1 mol/L aqueous solution of hydrochloric acid, and the mixture was extracted with ethyl acetate. The obtained organic layer was washed with 1 mol/L aqueous solution of hydrochloric acid and brine, dried over anhydrous magnesium sulfate to obtain Compound 18 (5.33 g, 100%).

1H-NMR (CDCl3) δ: 4.64 (q, J=8.2 Hz, 2H), 5.38 (s, 2H), 6.49 (d, J=5.6 Hz, 1H), 7.30-7.38 (m, 3H), 7.43-7.49 (m, 2H), 7.75 (d, J=5.6 Hz, 1H).

Second and Third Steps

Compound 20 was obtained in the same manner as in the fifth and sixth steps in reference example 1.

1H-NMR (CDCl3) δ: 4.55 (q, J=8.3 Hz, 2H), 5.18 (s, 2H), 5.29 (s, 2H), 6.37 (d, J=7.8 Hz, 1H), 7.30-7.42 (m, 6H).

Fourth and Fifth Steps

Compound 23 was obtained in the same manner as in the seventh step in reference example 1.

LC/MS (ESI): m/z=342.1 [M+H]+, RT=1.00, 1.09 min, method (1)

Sixth Step

To a solution of Compound 23 (820 mg, 2.40 mmol) in dichloromethane (16.5 mL) were added Boc2O (0.837 mL, 3.60 mmol), triethylamine (0.499 mL, 3.60 mmol) and 4-(dimethylamino)pyridine (44.0 mg, 0.360 mmol), and the mixture was stirred at room temperature for 3.5 hours. To the mixture was added 1 mol/L aqueous solution of hydrochloric acid and the mixture was extracted with ethyl acetate. The obtained organic layer was washed with 1 mol/L aqueous solution of hydrochloric acid and brine, dried over anhydrous sodium sulfate, and concentrated under reduced pressure. The obtained residue was purified by silica gel column chromatography (chloroform-methanol) to obtain Compound 24 (593 mg, 56%) and Compound i3 (170 mg, 16%).
Compound 24: LC/MS (ESI): m/z=441.9 [M+H]+, RT=1.67 min, method (1)

Seventh Step

Compound 24 (547 mg, 1.24 mmol) was dissolved in acetic acid (5.5 mL) and the mixture was stirred at 80° C. for 5 hours. The mixture was concentrated under reduced pressure and the obtained residue was purified by silica gel column chromatography (chloroform-methanol) to obtain Compound i3 (454 mg, 100%).

1H-NMR (CDCl3) δ: 1.46 (d, J=6.4 Hz, 3H), 3.45 (dd, J=10.5, 10.5 Hz, 1H), 3.55 (dd, J=11.7, 4.3 Hz, 1H), 3.92 (dd, J=11.7, 3.6 Hz, 1H), 3.95-4.01 (m, 2H) 4.76 (dq, J=13.9, 4.3 Hz, 1H), 5.19 (d, J=10.2 Hz, 1H), 5.22 (d, J=10.2 Hz, 1H), 5.36 (d, J=12.9 Hz, 1H), 6.28 (d, J=7.8 Hz, 1H), 7.25 (d, J=7.8 Hz, 1H), 7.28-7.36 (m, 3H), 7.56-7.61 (m, 2H).

Example 1

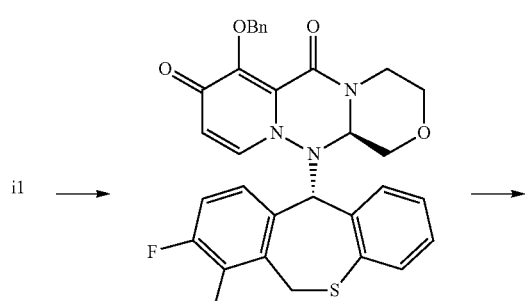

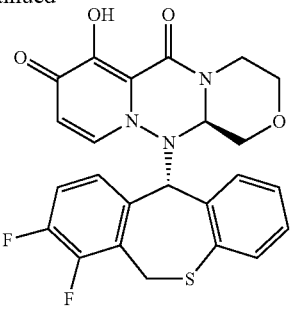

First Step

Compound i1 (1100 g, 3360 mmol) and 7,8-difluoro-6,11-dihydrodibenzothiepine-11-ol (977 g, 3697 mmol) were suspended in 50 wt % T3P in ethyl acetate (3208 g, 5041 mmol) and ethyl acetate (1.1 L). To the mixture was added methanesulfonic acid (436 ml, 6721 mmol) at room temperature and the mixture was stirred at 70° C. for 5.5 hours. To the mixture was added water under ice-water bath and the mixture was stirred at room temperature for 1 hour. THF was added thereto and the mixture was extracted with ethyl acetate. The obtained organic layer was washed with water and 8% aqueous solution of sodium hydrogen carbonate, dried over anhydrous sodium sulfate, and concentrated under reduced pressure. The obtained residue was dissolved in THF (5.5 L) and potassium carbonate (790 g, 5713 mmol) was added thereto. The mixture was warmed up to 50° C., benzyl bromide (240 ml, 2016 mmol) was added dropwise thereto, and the mixture was stirred at 60° C. for 8.5 hours. To the mixture was added dropwise 2 mol/L aqueous solution of hydrochloric acid under ice-water bath, and the mixture was stirred at room temperature for 10 minutes and extracted with ethyl acetate. The obtained organic layer was washed with water and 8% aqueous solution of sodium hydrogen carbonate and dried over anhydrous magnesium sulfate. An activated carbon (Norit SX-2, 240 g) was added thereto, the mixture was filtered through Celite, and the filtrate was concentrated under reduced pressure To the obtained residue was added ethyl acetate and hexane and the precipitated solid was filtered to obtain Compound 25 (1019 g, 1776 mmol, 53%).

$^1$H-NMR (CDCl$_3$) δ: 2.88 (1H, t, J=11.2 Hz), 3.28-3.39 (2H, m), 3.72 (1H, d, J=12.6 Hz), 3.86 (1H, d, J=9.6 Hz), 4.03 (1H, d, J=13.9 Hz), 4.45 (1H, d, J=8.6 Hz), 4.67 (1H, d, J=13.1 Hz), 5.19-5.26 (2H, m), 5.45 (1H, d, J=10.9 Hz), 5.63 (1H, d, J=10.9 Hz), 5.77 (1H, d, J=7.6 Hz), 6.40 (1H, d, J=7.8 Hz), 6.68 (1H, t, J=6.9 Hz), 6.94-7.01 (2H, m), 7.03-7.12 (3H, m), 7.29-7.38 (3H, m), 7.61 (2H, d, J=7.1 Hz).

Second Step

To a solution of Compound 25 (1200 g, 2092 mmol) in DMA (3.6 L) was added lithium chloride (443 g, 10.5 mol) at room temperature, and the mixture was stirred at 80° C. for 3 hours. To the mixture were added acetone (1.2 L), 0.5 mol/L aqueous solution of hydrochloric acid (6.0 L) and water (2.4 L) under ice-water bath, and the mixture was stirred for 1 hour. The precipitated solid was filtered. The obtained solid was dissolved in chloroform, isopropyl ether was added thereto, and the precipitated solid was filtered to obtain Compound III-2 (950 g, 1965 mmol, 94%).

$^1$H-NMR (CDCl3) δ: 2.99 (1H, dt, J=17.5, 6.8 Hz), 3.47 (1H, td, J=11.9, 2.5 Hz), 3.60 (1H, t, J=10.6 Hz), 3.81 (1H, dd, J=11.9, 3.3 Hz), 3.96 (1H, dd, J=11.0, 2.9 Hz), 4.07 (1H, d, J=13.8 Hz), 4.58 (1H, dd, J=10.0, 2.9 Hz), 4.67 (1H, dd, J=13.5, 1.9 Hz), 5.26-5.30 (2H, m), 5.75 (1H, d, J=7.8 Hz), 6.69 (1H, d, J=7.7 Hz), 6.83-6.87 (1H, m), 6.99-7.04 (2H, m), 7.07-7.15 (3H, m).

Example 2

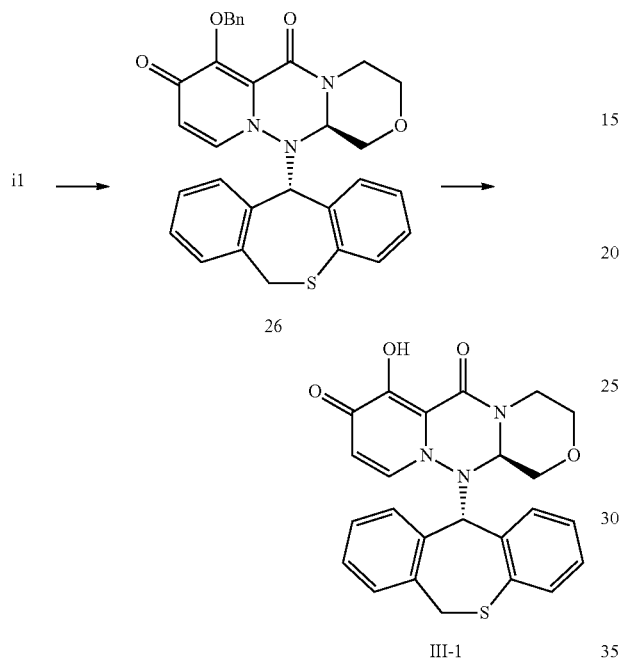

Example 3

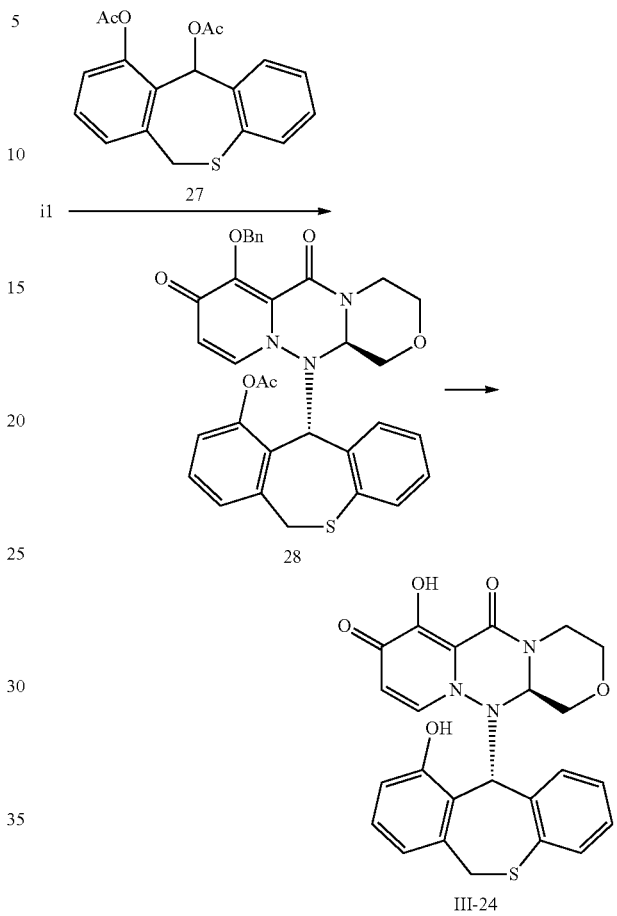

First Step

Compound i1 (400 mg, 1.22 mmol) and 6,11-dihydrodibenzothiepine-11-ol (418 mg, 1.83 mmol) were dissolved in 50% T3P in ethyl acetate (7.27 mL, 12.2 mmol) and the mixture was stirred in a sealed tube at 110° C. for 1.5 hours. To the mixture was added water and the mixture was extracted with ethyl acetate. The obtained organic layer was washed with brine, dried over anhydrous sodium sulfate, and concentrated under reduced pressure. The obtained residue was purified by silica gel column chromatography (chloroform-methanol and ethyl acetate-methanol) to obtain Compound 26 (316 mg, 47%).

1H-NMR (CDCl3) δ: 2.86 (dd, J=11.4, 11.4 Hz, 1H), 3.26-3.40 (m, 2H), 3.55 (d, J=13.4 Hz, 1H), 3.70 (d, J=10.4 Hz, 1H), 3.86 (d, J=10.4 Hz, 1H), 4.48 (d, J=9.5 Hz, 1H), 4.66 (d, J=13.4 Hz, 1H), 5.20 (s, 1H), 5.43-5.50 (m, 2H), 5.63 (d, J=10.9 Hz, 1H), 5.79 (d, J=7.8 Hz, 1H), 6.40 (d, J=7.7 Hz, 1H), 6.62-6.69 (m, 1H), 7.02-7.07 (m, 3H), 7.18 (d, J=7.4 Hz, 1H), 7.27-7.44 (m, 6H), 7.60-7.66 (m, 2H).

Second Step

Compound III-1 was obtained in the same manner as in the second step in example 1.

1H-NMR (CDCl3) δ: 2.98 (dd, J=13.0, 12.3 Hz, 1H), 3.46 (dd, J=13.1, 10.0 Hz, 1H), 3.55-3.63 (m, 2H), 3.79 (d, J=11.4 Hz, 1H), 3.96 (d, J=11.0 Hz, 1H), 4.62-4.66 (m, 2H), 5.26 (s, 1H), 5.52 (d, J=13.4 Hz, 1H), 5.75 (d, J=7.7 Hz, 1H), 6.70 (d, J=7.7 Hz, 1H), 6.79-6.85 (m, 1H), 7.05-7.12 (m, 3H), 7.23 (d, J=7.4 Hz, 1H), 7.30 (t, J=7.3 Hz, 1H), 7.36 (d, J=7.4 Hz, 1H), 7.44 (t, J=7.4 Hz, 1H).

First Step

Compound 27 (290 mg, 0.880 mmol) and Compound i1 (240 mg, 0.733 mmol) were dissolved in 50% T3P in ethyl acetate (2.4 mL) and the mixture was stirred in a sealed tube at 100° C. for 1.5 hours. To the mixture was added water and the mixture was extracted with ethyl acetate. The obtained organic layer was washed with brine, dried over anhydrous magnesium sulfate, and concentrated under reduced pressure. The obtained residue was purified by silica gel column chromatography (chloroform-ethyl acetate-methanol) to obtain Compound 28 (106 mg, 24%).

1H-NMR (CDCl3) δ: 2.37 (s, 3H), 2.94-3.03 (m, 1H), 3.15-3.23 (m, 1H), 3.28 (t, J=10.4 Hz, 1H), 3.58 (d, J=13.2 Hz, 1H), 3.66 (dd, J=3.2 Hz, 11.6 Hz, 1H), 3.84 (d d, J=2.8 Hz, 10.8 Hz, 1H), 4.40-4.52 (m, 2H), 5.49 (t, J=13.6 Hz, 2H), 5.60 (d, J=10.4 Hz, 2H), 5.78 (d, J=7.6 Hz, 1H), 6.41 (d, J=7.2 Hz, 1H), 6.66-6.71 (m, 1H), 6.98-7.12 (m, 4H), 7.21 (d, J=7.6 Hz, 1H), 7.30-7.42 (m, 4H), 7.56-7.61 (m 2H).

Second Step

To a solution of Compound 28 (100 mg, 0.168 mmol) in methanol (1 mL) was added 2 mol/L aqueous solution of sodium hydroxide (252 µL, 0.504 mmol) and the mixture was stirred at room temperature for 1 hour. To the mixture was added 2 mol/L aqueous solution of hydrochloric acid (0.3 mL) and the mixture was extracted with chloroform. The obtained organic layer was concentrated under reduced pressure. The obtained residue was dissolved in DMA (1.0 mL), lithium chloride (35.6 mg, 0.839 mmol) was added thereto, and the mixture was stirred at 100° C. for 15 hours. The mixture was purified by reversed phase silica gel column chromatography (acetonitrile-water) to obtain Compound III-24 (20 mg, 26%).

1H-NMR (CDCl3) δ: 3.09 (t, J=11.2 Hz, 1H), 3.40-3.58 (m, 3H), 3.76 (d, J=10.8H z, 1H), 3.91 (d, J=10.8 Hz, 1H), 4.66 (d, J=13.2 Hz, 1H), 4.73 (d, J=9.6 Hz, 1H), 5.50 (d, J=13.6 Hz, 1H), 5.79 (d, J=6.8 Hz, 1H), 6.25 (s, 1H), 6.61-6.70 (m, 2H), 6.79 (d, J=6.8 Hz, 1H), 6.93-7.08 (m, 3H), 7.10-7.19 (m, 2H).

The following example compounds were synthesized from commercially available compounds or intermediates described in reference example according to the above examples.

TABLE 1

| No. | Structure | H-NMR or LC/MS |
|---|---|---|
| III-3 | 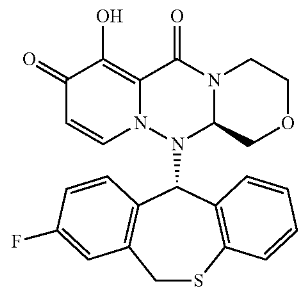 [SMILES: O=C1c2c(O)c(=O)ccn2N([C@H]2c3ccc(F)cc3CSc3ccccc32)[C@@H]2COCCN12] | 1H-NMR (CDCl3) δ: 2.99 (t, J = 12.4 Hz, 1H), 3.43-3.61 (m, 3H), 3.81 (d, J = 12.0 Hz, 1H), 3.96 (d, J = 11.0 Hz, 1H), 4.59 (d, J = 9.8 Hz, 1H), 4.66 (d, J = 13.2 Hz, 1H), 5.26 (s, 1H), 5.54 (d, J = 13.4 Hz, 1H), 5.75 (d, J = 8.2 Hz, 1H), 6.69 (d, J = 7.7 Hz, 1H), 6.84 (t, J = 7.0 Hz, 1H), 6.98-7.05 (m, 2H), 7.07-7.12 (m, 3H), 7.22 (t, J = 7.0 Hz, 1H). |
| III-4 | 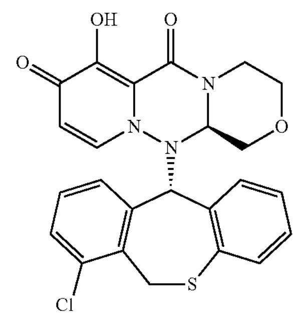 [SMILES: O=C1c2c(O)c(=O)ccn2N([C@@H]2c3ccccc3SCc3c(Cl)cccc32)[C@@H]2COCCN12] | 1H-NMR (CDCl3) δ: 3.09 (t, J = 12.7 Hz, 1H), 3.48 (t, J = 11.9 Hz, 1H), 3.59 (t, J = 11.2 Hz, 2H), 3.82 (d, J = 11.7 Hz, 1H), 3.94 (d, J = 10.9 Hz, 1H), 4.53 (d, J = 10.2 Hz, 1H), 4.71 (d, J = 13.6 Hz, 1H), 5.68 (d, J = 13.2 Hz, 1H), 5.77 (d, J = 7.5 Hz, 1H), 6.26 (s, 1H), 6.81-6.88 (m, 2H), 7.07-7.16 (m, 3H), 7.26-7.28 (m, 1H), 7.35 (t, J = 7.7 Hz, 1H), 7.40 (d, J = 8.2 Hz, 1H). |
| III-5 | 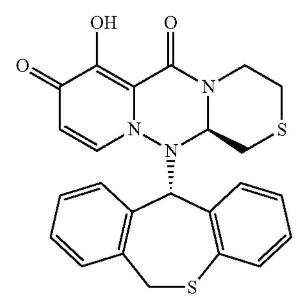 [SMILES: O=C1c2c(O)c(=O)ccn2N([C@H]2c3ccccc3CSc3ccccc32)[C@@H]2CSCCN12] | 1H-NMR(CDCl3)δ: 2.34 (d, J = 13.2 Hz, 1H), 2.57 (d, J = 12.4 Hz, 1H), 2.79-2.87 (m, 1H), 2.90-3.01 (m, 2H), 3.58 (d, J = 13.6 Hz, 1H), 4.67 (dd, J = 2.4, 10.8 Hz, 1H), 5.03-5.08 (m, 1H), 5.12 (s, 1H), 5.53 (d, J = 13.6 Hz, 1H), 5.79 (d, J = 7.6 Hz, 1H), 6.68 (d, J = 7.6 Hz, 1H), 6.78-6.84 (m, 1H), 7.05-7.10 (m, 3H), 7.20 (d, J = 7.2 Hz, 1H), 7.31 (t, J = 8.0 Hz, 1H), 7.37 (d, J = 6.4 Hz, 1H), 7.45 (t, J = 7.6 Hz, 1H) |
| III-7 | 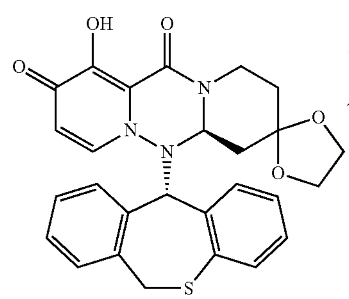 | 1H-NMR(CDCl3)δ: 1.64-1.69 (m, 2H), 1.88-1.96 (m, 2H), 2.60-2.70 (m, 1H), 3.58 (d, J = 13.2 Hz, 1H), 3.80-3.96 (m, 4H), 4.52-4.67 (m, 2H), 5.21 (s, 1H), 5.53 (d, J = 13.2 Hz, 1H), 5.78 (d, J = 7.6 Hz, 1H), 6.69 (d, J = 7.6 Hz, 1H), 6.78-6.85 (m, 1H), 7.00-7.09 (m, 3H), 7.20 (d, J = 7.6 Hz, 1H), 7.29 (t, J = 7.2 Hz, 1H), 7.35 (d, J = 7.2 Hz, 1H), 7.42 (t, J = 7.2 Hz, 1H). |

TABLE 1-continued

| No. | Structure | H-NMR or LC/MS |
|---|---|---|
| III-8 | 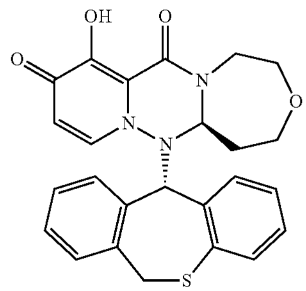 [SMILES: O=C1c2c(O)c(=O)ccn2N([C@H]2c3ccccc3CSc3ccccc32)[C@@H]2CCOCCN12] | 1H-NMR(CDCl3)δ: 1.90-1.99 (m, 1H), 2.26-2.32 (m, 1H), 2.60-2.68 (m, 1H), 3.38-3.43 (m, 1H), 3.55-3.64 (m, 2H), 3.90 (dd, J = 3.6 Hz, 12.8 Hz, 1H), 4.00-4.06 (m, 1H), 4.63 (dd, J = 2.4 Hz, 14.2 Hz, 1H), 4.70-4.75 (m, 1H), 5.06 (s, 1H), 5.52 (d, J = 13.2 Hz, 1H), 5.84 (d, J = 7.6 Hz, 1H), 6.69 (d, J = 7.6 Hz, 1H), 6.80-6.85 (m, 1H), 7.03 (d, J = 7.6 Hz, 1H), 7.10 (d, J = 4.0 Hz, 2H), 7.17 (d, J = 7.6 Hz, 1H), 7.30 (t, J = 7.2 Hz, 1H), 7.36 (d, J = 6.4 Hz, 1H), 7.44 (t, J = 7.6 Hz, 1H) |
| III-9 | 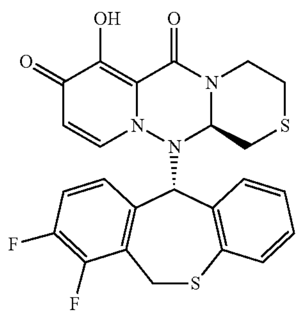 [SMILES: O=C1c2c(O)c(=O)ccn2N([C@@H]2c3ccccc3SCc3c2ccc(F)c3F)[C@@H]2CSCCN12] | 1H-NMR(CDCl3)δ: 2.37 (d, J = 13.2 Hz, 1H), 2.57 (d, J = 12.4 Hz, 1H), 2.79-2.87 (m, 1H), 2.90-3.03 (m, 2H), 4.08 (d, J = 13.6 Hz, 1H), 4.64 (d, J = 10.8 Hz, 1H), 5.05 (d, J = 12.0 Hz, 1H), 5.19 (s, 1H), 5.25-5.32 (m, 1H), 5.78 (d, J = 7.6 Hz, 1H), 6.66 (d, J = 7.6 Hz, 1H), 6.84 (t, J = 7.6 Hz, 1H), 6.90-7.20 (m, 5H). |

TABLE 2

| No. | Structure | H-NMR or LC/MS |
|---|---|---|
| III-10 | 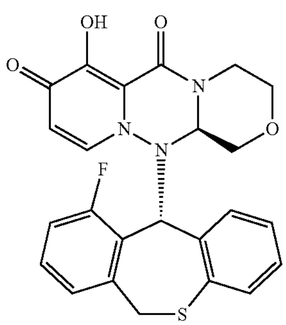 [SMILES: O=C1c2c(O)c(=O)ccn2N([C@@H]2c3ccccc3SCc3cccc(F)c32)[C@@H]2COCCN12] | 1H-NMR(CDCl3)δ: 3.06 (t, J = 11.6 Hz, 1H), 3.47 (t, J = 11.2 Hz, 1H), 3.50-3.63 (m, 2H), 3.80 (d, J = 11.6 Hz, 1H), 3.94 (d, J = 11.2 Hz, 1H), 4.58 (d, J = 9.6 Hz, 1H), 4.69 (d, J = 13.6 Hz, 1H), 5.57 (d, J = 13.6 Hz, 1H), 5.75 (d, J = 7.6 Hz, 1H), 5.90 (s, 1H), 6.78 (d, J = 7.6 Hz, 1H), 6.85 (t, J = 7.6 Hz, 1H), 7.04-7.17 (m, 5H), 7.35-7.42 (m, 1H). |
| III-11 | 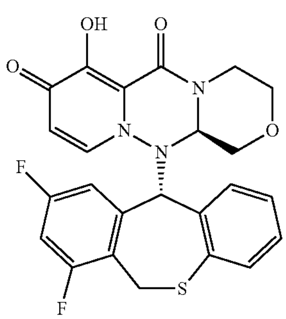 [SMILES: O=C1c2c(O)c(=O)ccn2N([C@@H]2c3ccccc3SCc3c(F)cc(F)cc32)[C@@H]2COCCN12] | 1H-NMR(CDCl3)δ: 3.04 (t, J = 12.0 Hz, 1H), 3.47 (t, J = 11.6 Hz, 1H), 3.59 (t, J = 11.2 Hz, 1H), 3.82 (d, J = 12.0 Hz, 1H), 3.97 (d, J = 10.8 Hz, 1H), 4.03 (d, J = 14.0 Hz, 1H), 4.56 (d, J = 11.6 Hz, 1H), 4.68 (d, J = 13.6 Hz, 1H), 5.17 (d, J = 14.0 Hz, 1H), 5.24 (s, 1H), 5.75 (d, J = 8.0 Hz, 1H), 6.69 (d, J = 7.6 Hz, 1H), 6.80-6.88 (m, 2H), 6.98 (t, J = 8.8 Hz, 1H), 7.04-7.16 (m, 3H). |

TABLE 2-continued

| No. | Structure | H-NMR or LC/MS |
|---|---|---|
| III-12 | 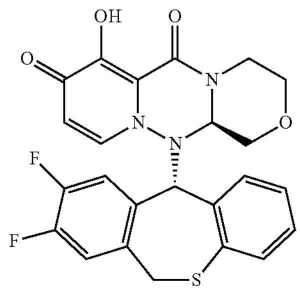 [SMILES: O=C1c2c(O)c(=O)ccn2N([C@H]2c3cc(F)c(F)cc3CSc3ccccc32)[C@@H]2COCCN12] | 1H-NMR(CDCl3)δ: 3.04 (t, J = 12.8 Hz, 1H), 3.40-3.62 (m, 3H), 3.82 (d, J = 12.0 Hz, 1H), 3.96 (d, J = 11.2 Hz, 1H), 4.58 (d, J = 9.6 Hz, 1H), 4.68 (d, J = 13.6 Hz, 1H), 5.19 (s, 1H), 5.49 (d, J = 13.6 Hz, 1H), 5.74 (d, J = 7.6 Hz, 1H), 6.68 (d, J = 7.2 Hz, 1H), 6.85 (t, J = 7.6 Hz, 1H), 7.03 (d, J = 7.6 Hz, 1H), 7.06-7.16 (m, 3H), 7.21 (t, J = 8.8 Hz, 1H). |
| III-13 | 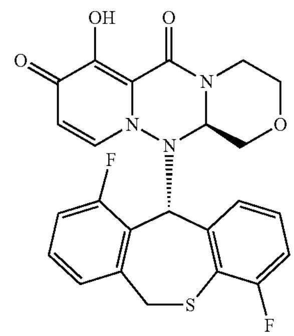 [SMILES: O=C1c2c(O)c(=O)ccn2N([C@@H]2c3cccc(F)c3SCc3cccc(F)c32)[C@@H]2COCCN12] | 1H-NMR(CDCl3)δ: 3.04 (t, J = 12.0 Hz, 1H), 3.47 (t, J = 12.0 Hz, 1H), 3.58 (t, J = 10.8 Hz, 1H), 3.69 (d, J = 13.6 Hz, 1H), 3.81 (d, J = 12.0 Hz, 1H), 3.94 (d, J = 11.2 Hz, 1H), 4.57 (d, J = 13.6 Hz, 1H), 4.69 (d, J = 14.0 Hz, 1H), 5.59 (d, J = 13.6 Hz, 1H), 5.79 (d, J = 7.6 Hz, 1H), 5.96 (s, 1H), 6.63 (d, J = 7.6 Hz, 1H), 6.81-6.88 (m, 1H), 6.96 (t, J = 9.6 Hz, 1H), 7.04-7.13 (m, 2H), 7.17 (d, J = 7.6 Hz, 1H), 7.38-7.45 (m, 1H). |
| III-14 | 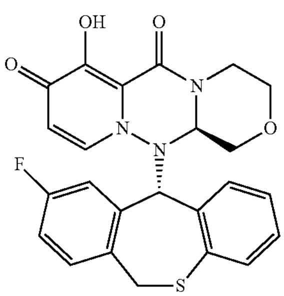 [SMILES: O=C1c2c(O)c(=O)ccn2N([C@H]2c3cc(F)ccc3CSc3ccccc32)[C@@H]2COCCN12] | 1H-NMR (CDCl3) δ: 3.00-3.07 (m, 1H), 3.47 (td, J = 12.0, 2.6 Hz, 1H), 3.57-3.62 (m, 2H), 3.82 (dd, J = 11.9, 3.3 Hz, 1H), 3.97 (dd, J = 11.1, 2.9 Hz, 1H), 4.60 (dd, J = 10.0, 3.0 Hz, 1H), 4.68 (dd, J = 13.6, 2.0 Hz, 1H), 5.20 (s, 1H), 5.47 (d, J = 13.4 Hz, 1H), 5.76 (d, J = 7.8 Hz, 1H), 6.70 (d, J = 7.8 Hz, 1H), 6.82-6.86 (m, 1H), 6.98 (dd, J = 8.7, 2.5 Hz, 1H), 7.07-7.16 (m, 4H), 7.35 (dd, J = 8.3, 5.5 Hz, 1H). |
| III-15 | 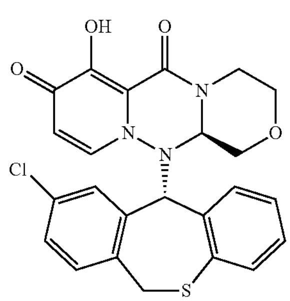 [SMILES: O=C1c2c(O)c(=O)ccn2N([C@H]2c3cc(Cl)ccc3CSc3ccccc32)[C@@H]2COCCN12] | 1H-NMR (CDCl3) δ: 3.02-3.09 (m, 1H), 3.47 (td, J = 11.9, 2.6 Hz, 1H), 3.56-3.62 (m, 2H), 3.82 (dd, J = 11.9, 3.3 Hz, 1H), 3.96 (dd, J = 11.2, 3.0 Hz, 1H), 4.59 (dd, J = 10.0, 3.1 Hz, 2H), 4.69 (dd, J = 13.6, 2.3 Hz, 2H), 5.20 (s, 1H), 5.47 (d, J = 13.4 Hz, 1H), 5.75 (d, J = 7.8 Hz, 1H), 6.71 (d, J = 7.8 Hz, 1H), 6.82-6.87 (m, 1H), 7.05-7.14 (m, 3H), 7.25 (d, J = 2.1 Hz, 1H), 7.31 (d, J = 8.2 Hz, 1H), 7.41 (dd, J = 8.2, 2.1 Hz, 1H). |

TABLE 3

| No. | Structure | H-NMR or LC/MS |
|---|---|---|
| III-16 | 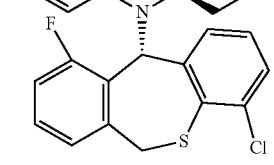 | 1H-NMR (CDCl3) δ: 3.01-3.09 (m, 1H), 3.47 (td, J = 11.9, 2.6 Hz, 1H), 3.59 (t, J = 10.5 Hz, 1H), 3.72 (dd, J = 13.6, 0.9 Hz, 1H), 3.82 (dd, J = 12.0, 3.2 Hz, 1H), 3.95 (dd, J = 11.0, 3.0 Hz, 1H), 4.58 (dd, J = 10.0, 3.1 Hz, 1H), 4.70 (dd, J = 13.6, 2.3 Hz, 1H), 5.63 (d, J = 13.6 Hz, 1H), 5.80 (d, J = 7.8 Hz, 1H), 5.95 (s, 1H), 6.76 (dd, J = 7.8, 1.4 Hz, 1H), 6.82 (t, J = 7.8 Hz, 1H), 7.06 (d, J = 7.8 Hz, 1H), 7.10 (t, J = 9.1 Hz, 1H), 7.17 (d, J = 7.5 Hz, 1H), 7.29 (dd, J = 7.9, 1.5 Hz, 1H), 7.42 (td, J = 8.0, 5.6 Hz, 1H). |
| III-17 | 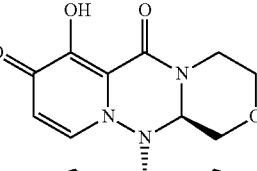 | 1H-NMR (CDCl3) δ: 2.97-3.04 (m, 1H), 3.47 (td, J = 11.9, 2.7 Hz, 1H), 3.60 (t, J = 10.7 Hz, 1H), 3.82 (dd, J = 12.0, 3.1 Hz, 1H), 3.94-4.00 (m, 2H), 4.58 (dd, J = 10.0, 3.0 Hz, 1H), 4.68 (dd, J = 13.7, 2.1 Hz, 1H), 5.39 (s, 1H), 5.73 (d, J = 14.6 Hz, 1H), 5.77 (d, J = 7.8 Hz, 1H), 6.70 (d, J = 7.4 Hz, 1H), 6.82-6.86 (m, 1H), 7.01 (d, J = 7.7 Hz, 1H), 7.08-7.15 (m, 2H), 7.40-7.45 (m, 2H), 7.80-7.83 (m, 1H). |
| III-18 | 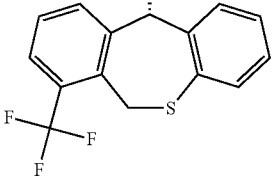 | 1H-NMR(CDCl3)δ: 2.39 (s, 3H), 3.00 (t, J = 11.6 Hz, 1H), 3.47 (t, J = 13.2 Hz, 1H), 3.50-3.61 (m, 2H), 3.80 (d, J = 12.0 Hz, 1H), 3.95 (d, J = 11.2 Hz, 1H), 4.60 (d, J = 10.0 Hz, 1H), 4.68 (d, J = 13.6 Hz, 1H), 5.62 (d, J = 13.2 Hz, 1H), 5.73 (s, 1H), 5.77 (d, J = 7.6 Hz, 1H), 6.73 (d, J = 8.0 Hz, 1H), 6.82 (t, J = 6.0 Hz, 1H), 7.07-7.20 (m, 6H). |
| III-19 | 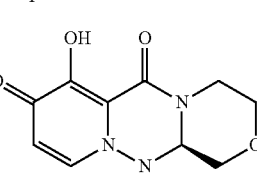 | 1H-NMR (CDCl3) δ: 2.95-3.03 (m, 1H), 3.43-3.49 (m, 2H), 3.59 (t, J = 10.6 Hz, 1H), 3.81 (dd, J = 12.0, 3.2 Hz, 1H), 3.97 (dd, J = 11.2, 3.0 Hz, 1H), 4.08 (d, J = 13.7 Hz, 1H), 4.60 (dd, J = 10.0, 3.0 Hz, 1H), 4.67 (dd, J = 13.6, 2.3 Hz, 1H), 5.23 (dd, J = 13.7, 2.1 Hz, 1H), 5.31 (s, 1H), 5.76 (d, J = 7.7 Hz, 1H), 6.70 (d, J = 7.5 Hz, 1H), 6.81-6.86 (m, 1H), 7.02-7.14 (m, 4H), 7.20-7.30 (m, 1H). |
| III-20 | 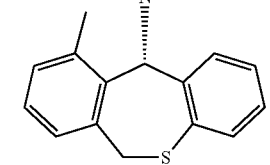 | 1H-NMR(CDCl3)δ: 3.09 (t, J = 12.8 Hz, 1H), 3.48 (t, J = 11.6 Hz, 1H), 3.55-3.62 (m, 2H), 3.81 (d, J = 11.6 Hz, 1H), 3.93 (d, J = 10.8 Hz, 1H), 4.53 (d, J = 9.6 Hz, 1H), 4.69 (d, J = 13.2 Hz, 1H), 5.68 (d, J = 12.8 Hz, 1H), 5.76 (d, J = 6.8 Hz, 1H), 6.26 (s, 1H), 6.80-6.88 (m, 2H), 7.05-7.15 (m, 3H), 7.24-7.28 (m, 1H), 7.34 (t, J = 7.6 Hz, 1H), 7.39 (d, J = 8.0 Hz, 1H). |

TABLE 3-continued

| No. | Structure | H-NMR or LC/MS |
|---|---|---|
| III-21 | 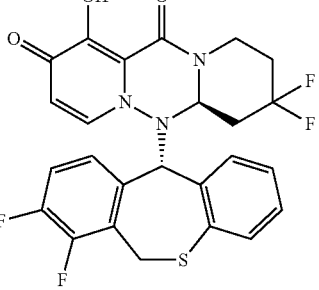 | 1H-NMR(CDCl3)δ: 1.85-1.98 (m, 1H), 2.10-2.23 (m, 2H), 2.31-2.43 (m, 1H), 2.69 (t, J = 10.8 Hz, 1H), 4.09 (d, J = 13.2 Hz, 1H), 4.51 (d, J = 12.4 Hz, 1H), 4.77 (d, J = 13.6 Hz, 1H), 5.20-5.30 (m, 1H), 5.78 (d, J = 7.2 Hz, 1H), 5.77 (d, J = 7.6 Hz, 1H), 6.68 (d, J = 7.2 Hz, 1H), 6.81-6.88 (m, 1H), 6.96-7.02 (m, 1H), 7.05-7.17 (m, 4H). |

TABLE 4

| No. | Structure | H-NMR or LC/MS |
|---|---|---|
| III-22 | 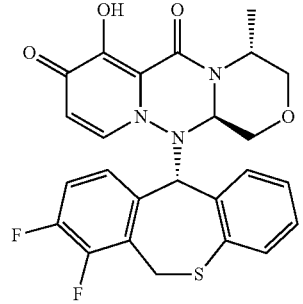 [SMILES: C[C@@H]1COC[C@@H]2N1C(=O)c1c(O)c(=O)ccn1N2[C@@H]1c2ccccc2SCc2c1ccc(F)c2F] | 1H-NMR (CDCl3) δ: 1.22 (d, J = 7.2 Hz, 3H), 3.49-3.58 (m, 4H), 3.95 (dd, J = 10.8, 2.8 Hz, 1H), 4.08 (d, J = 13.8 Hz, 1H), 4.74 (dd, J = 10.0, 2.8 Hz, 1H), 4.99-5.05 (m, 1H), 5.22 (s, 1H), 5.30 (dd, J = 13.8, 2.3 Hz, 1H), 5.75 (d, J = 7.8 Hz, 1H), 6.69 (d, J = 7.7 Hz, 1H), 6.84 (t, J = 7.0 Hz, 1H), 6.97-7.02 (m, 2H), 7.08-7.14 (m, 3H). |
| III-23 | 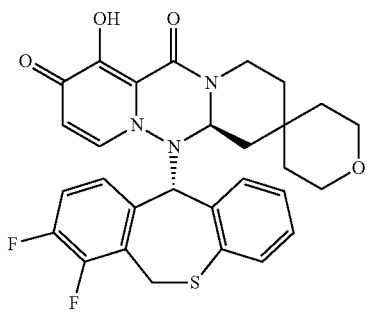 [SMILES: O=C1c2c(O)c(=O)ccn2N([C@@H]2c3ccccc3SCc3c2ccc(F)c3F)[C@@H]2CC3(CCOCC3)CCN12] | 1H-NMR (CDCl3) δ: 1.29-1.87 (m, 8H), 2.67 (td, J = 13.5, 2.6 Hz, 1H), 3.54-3.66 (m, 5H), 4.08 (d, J = 13.7 Hz, 1H), 4.47 (dd, J = 12.0, 2.3 Hz, 1H), 4.61 (dd, J = 13.8, 3.1 Hz, 1H), 5.24-5.33 (m, 2H), 5.79 (d, J = 7.8 Hz, 1H), 6.68 (d, J = 7.5 Hz, 1H), 6.83-6.87 (m, 1H), 6.98-7.15 (m, 5H). |
| III-25 | 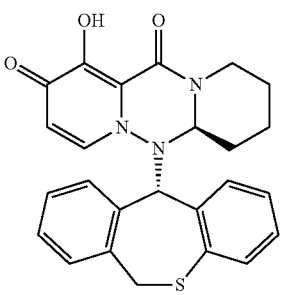 [SMILES: O=C1c2c(O)c(=O)ccn2N([C@H]2c3ccccc3CSc3ccccc32)[C@@H]2CCCCN12] | 1H-NMR (CDCl3) δ: 1.47-1.75 (4H, m), 1.80-2.02 (2H, m), 2.53 (1H, t, J = 12.1 Hz), 3.57 (1H, d, J = 13.1 Hz), 4.30 (1H, d, J = 11.1 Hz), 4.70 (1H, d, J = 13.1 Hz), 5.21 (1H, s), 5.59 (1H, d, J = 13.4 Hz), 5.80 (1H, d, J = 7.3 Hz), 6.69 (1H, d, J = 7.6 Hz), 6.81 (1H, s), 7.08-7.11 (3H, m), 7.20-7.44 (4H, m) |

TABLE 4-continued

| No. | Structure | H-NMR or LC/MS |
|---|---|---|
| III-26 | 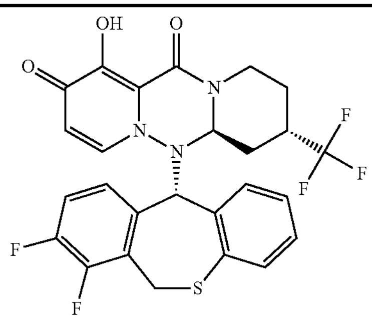 | 1H-NMR (CDCl3) δ: 1.82-2.17 (5H, m), 2.59-2.76 (1H, m), 2.84 (1H, t, J = 11.5 Hz) 4.09 (1H, d, J = 13.8 Hz), 4.63-4.69 (2H, m), 5.22 (1H, s), 5.27 (1H, dd, J = 13.9, 2.4 Hz), 5.79 (1H, d, J = 7.7 Hz), 6.68 (1H, d, J = 7.7 Hz), 6.83-6.87 (1H, m), 7.15-6.96 (5H, m). |
| III-27 | 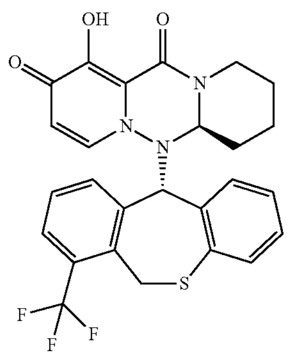 [SMILES: O=C1c2c(O)c(=O)ccn2N([C@@H]2c3ccccc3SCc3c2cccc3C(F)(F)F)[C@@H]2CCCCN12] | 1H-NMR (CDCl3) δ: 1.49-1.79 (m, 4H), 1.89 (d, J = 10.4 Hz, 1H), 1.99 (d, J = 11.8 Hz, 1H), 2.54 (td, J = 12.7, 2.4 Hz, 1H), 3.93 (d, J = 14.4 Hz, 1H), 4.27 (dd, J = 11.4, 2.6 Hz, 1H), 4.73 (d, J = 14.7 Hz, 1H), 5.35 (s, 1H), 5.78-5.82 (m, 2H), 6.69 (d, J = 7.8 Hz, 1H), 6.81-6.85 (m, 1H), 7.03 (d, J = 7.7 Hz, 1H), 7.07-7.14 (m, 2H), 7.38-7.44 (m, 2H), 7.78-7.81 (m, 1H). |
| III-28 | 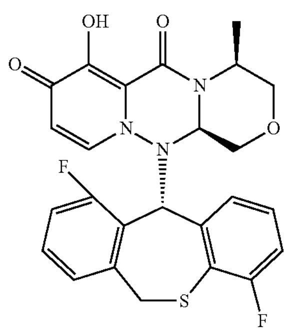 [SMILES: C[C@H]1COC[C@@H]2N1C(=O)c1c(O)c(=O)ccn1N2[C@@H]1c2cccc(F)c2SCc2cccc(F)c21] | 1H-NMR (CDCl3) δ: 1.79 (d, J = 7.2 Hz, 3H), 3.33-3.40 (m, 1H), 3.46-3.75 (m, 5H), 3.94 (dd, J = 11.0, 2.9 Hz, 1H), 4.43 (dd, J = 9.7, 2.7 Hz, 1H), 5.58 (d, J = 13.6 Hz, 1H), 5.81 (d, J = 7.7 Hz, 1H), 6.00 (s, 1H), 6.65 (d, J = 7.7 Hz, 1H), 6.82-6.88 (m, 1H), 6.94-7.01 (m, 2H), 7.11 (t, J = 9.2 Hz, 1H), 7.17 (d, J = 7.5 Hz, 1H), 7.39-7.44 (m, 1H). |

TABLE 5

| No. | Structure | H-NMR or LC/MS |
|---|---|---|
| III-29 | 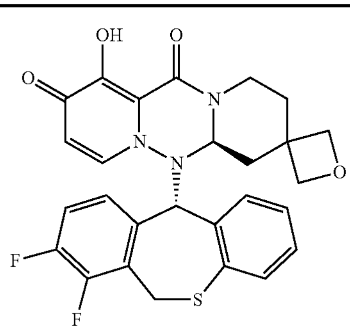 | 1H-NMR (CDCl3) δ: 1.62-1.69 (m, 1H), 1.90 (t, J = 12.4 Hz, 1H), 2.13 (d, J = 13.7 Hz, 1H), 2.38-2.46 (m, 2H), 4.09-4.20 (m, 3H), 4.32 (d, J = 6.3 Hz, 1H), 4.37-4.41 (m, 2H), 4.71 (dd, J = 13.7, 3.4 Hz, 1H), 5.23 (s, 1H), 5.36 (dd, J = 13.7, 2.6 Hz, 1H), 5.79 (d, J = 7.8 Hz, 1H), 6.68 (d, J = 7.8 Hz, 1H), 6.82-6.87 (m, 1H), 6.94-6.99 (m, 1H), 7.05-7.15 (m, 4H). |

TABLE 5-continued

| No. | Structure | H-NMR or LC/MS |
|---|---|---|
| III-30 | 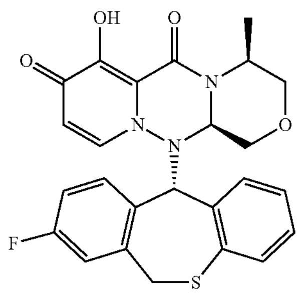 [SMILES: C[C@H]1COC[C@@H]2N1C(=O)c1c(O)c(=O)ccn1N2[C@H]1c2ccc(F)cc2CSc2ccccc21] | 1H-NMR (CDCl3) δ: 1.78 (d, J = 7.2 Hz, 3H), 3.26-3.32 (m, 1H), 3.44-3.60 (m, 3H), 3.72 (dd, J = 11.7, 2.6 Hz, 1H), 3.94 (dd, J = 11.2, 2.9 Hz, 1H), 4.42 (dd, J = 9.9, 2.8 Hz, 1H), 5.29 (s, 1H), 5.54 (d, J = 13.6 Hz, 1H), 5.76 (d, J = 7.8 Hz, 1H), 6.71 (d, J = 7.7 Hz, 1H), 6.81-6.86 (m, 1H), 6.96-7.04 (m, 2H), 7.07-7.11 (m, 3H), 7.23-7.25 (m, 1H). |
| III-31 | 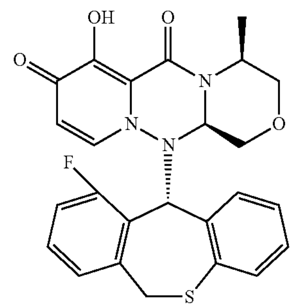 [SMILES: C[C@H]1COC[C@@H]2N1C(=O)c1c(O)c(=O)ccn1N2[C@@H]1c2ccccc2SCc2cccc(F)c21] | LC/MS (ESI): m/z = 480 [M + H]+, RT = 1.81 min, method (1) |
| III-32 | 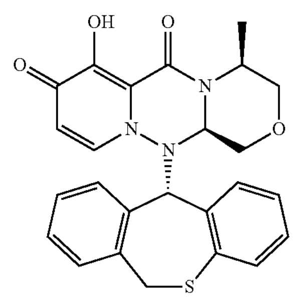 [SMILES: C[C@H]1COC[C@@H]2N1C(=O)c1c(O)c(=O)ccn1N2[C@H]1c2ccccc2CSc2ccccc21] | 1H-NMR (CDCl3) δ: 1.78 (d, J = 7.2 Hz, 3H), 3.25-3.30 (m, 1H), 3.44-3.51 (m, 2H), 3.54-3.59 (m, 2H), 3.71 (dd, J = 11.5, 2.6 Hz, 1H), 3.94 (dd, J = 11.2, 2.8 Hz, 1H), 4.45 (dd, J = 10.0, 2.8 Hz, 1H), 5.28 (s, 1H), 5.51 (d, J = 13.4 Hz, 1H), 5.77 (d, J = 7.7 Hz, 1H), 6.72 (d, J = 7.7 Hz, 1H), 6.80-6.84 (m, 1H), 7.01 (d, J = 7.7 Hz, 1H), 7.08-7.10 (m, 2H), 7.26-7.45 (m, 3H). |
| III-33 | 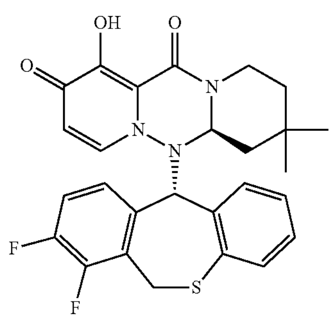 | 1H-NMR(CDCl3)δ: 0.85(s, 3H), 0.97(s, 3H), 1.34-2.00(m, 4H), 2.62-2.66(m, 1H), 4.05(d, J = 13.6 Hz, 1H), 4.40-4.48(m, 1H), 4.56-4.63(m, 1H), 5.24(s, 1H), 5.30-5.35(s, 1H), 5.80(d, J = 7.6 Hz, 1H), 6.68(d, J = 7.6 Hz, 1H), 6.78-6.90(m, 1H), 6.95-7.15(m, 4H), 7.16-7.22(m, 1H) |
| III-34 | 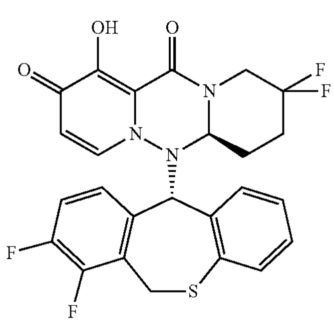 [SMILES: O=C1c2c(O)c(=O)ccn2N([C@@H]2c3ccccc3SCc3c2ccc(F)c3F)[C@@H]2CCC(F)(F)CN12] | 1H-NMR (CDCl3) δ: 1.86-2.18 (4H, m), 2.30-2.46 (1H, m), 2.90 (1H, dd, J = 30.0, 13.9 Hz), 4.07 (1H, d, J = 13.7 Hz), 4.41-4.48 (1H, m), 4.99-5.06 (1H, m), 5.20 (1H, s), 5.30 (1H, dd, J = 13.7, 2.4 Hz), 5.78 (1H, d, J = 7.8 Hz), 6.68 (1H, d, J = 7.8 Hz), 6.83-6.87 (1H, m), 7.00 (1H, dd, J = 8.3, 4.1 Hz), 7.06-7.17 (4H, m). |

TABLE 5-continued
| No. | Structure | H-NMR or LC/MS |
|---|---|---|
| III-35 | 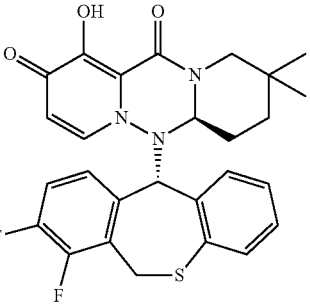 | 1H-NMR(CDCl3)δ: 0.89(s, 3H), 0.95(s, 3H), 1.25-2.20(m, 4H), 2.39(d, J = 12.4 Hz, 1H), 4.05(d, J = 12.4 Hz, 1H), 4.20-4.28(m, 1H), 4.39-4.44(m, 1H), 5.20(m, 1H), 5.33-5.38(m, 1H), 5.78(d, J = 7.6 Hz, 1H), 6.68(d, J = 7.6 Hz, 1H), 6.80-6.83(m, 1H), 6.88-7.18(m, 5H) |
TABLE 6
| No. | Structure | H-NMR or LC/MS |
|---|---|---|
| III-36 | 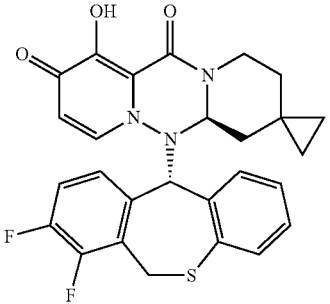 [SMILES: O=C1c2c(O)c(=O)ccn2N([C@@H]2c3ccccc3SCc3c2ccc(F)c3F)[C@@H]2CC3(CCN12)CC3] | 1H-NMR(CDCl3)δ: 0.18-0.25(m, 1H), 0.26-0.35(m, 1H), 0.36-0.50(m, 2H), 0.76-0.83(m, 1H), 0.98-1.40(m, 1H), 1.60-2.24(m, 4H), 2.60-2.70(m, 1H), 4.04(d, J = 13.6 Hz, 1H), 4.32-4.48(m, 1H), 4.69-4.75(m, 1H), 5.26(s, 1H), 5.77(d, J = 8.0 Hz, 1H), 6.69(d, J = 8.0 Hz, 1H), 6.80 6.90(m, 1H), 7.00 7.18(m, 5H) |
| III-37 | 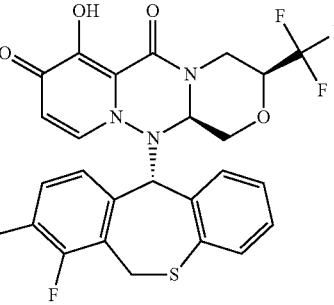 | 1H-NMR (CDCl3) δ: 3.26 (dd, J = 14.6, 5.7 Hz, 1H), 3.85-4.11 (m, 4H), 4.68 (dd, J = 10.4, 3.6 Hz, 1H), 5.07 (d, J = 14.7 Hz, 1H), 5.22-5.27 (m, 2H), 5.74 (d, J = 7.7 Hz, 1H), 6.69 (d, J = 7.5 Hz, 1H), 6.85 (t, J = 6.9 Hz, 1H), 6.97-7.15 (m, 5H). |
| III-38 | 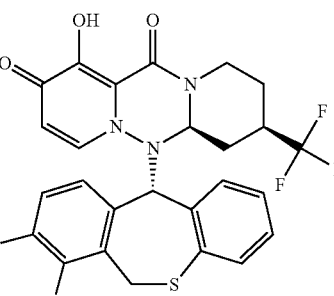 | 1H-NMR (CDCl3) δ: 1.49-1.79 (m, 2H), 1.91 (d, J = 11.9 Hz, 1H), 2.08-2.13 (m, 1H), 2.47-2.62 (m, 2H), 4.07-4.10 (m, 1H), 4.35 (dd, J = 11.9, 2.3 Hz, 1H), 4.84 (dd, J = 13.4, 4.0 Hz, 1H), 5.25 (s, 1H), 5.31 (dd, J = 13.9, 2.4 Hz, 1H), 5.79 (d, J = 7.7 Hz, 1H), 6.69 (d, J = 7.9 Hz, 1H), 6.83-6.87 (m, 1H), 6.97-7.00 (m, 1H), 7.06-7.15 (m, 4H). |

TABLE 6-continued

| No. | Structure | H-NMR or LC/MS |
|---|---|---|
| III-39 | 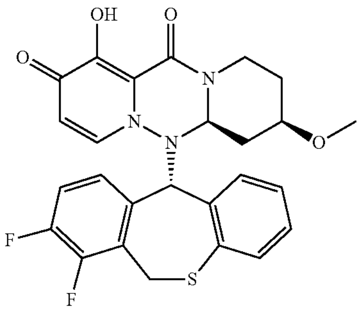 [SMILES: CO[C@@H]1CCN2C(=O)c3c(O)c(=O)ccn3N([C@@H]3c4ccccc4SCc4c3ccc(F)c4F)[C@@H]2C1] | 1H-NMR(CDCl3)δ: 1.31-1.44 (m, 1H), 1.58 (q, J = 11.6 Hz, 1H), 2.05 (d, J = 10.8 Hz, 1H), 2.26 (d, J = 11.6 Hz, 1H), 2.47 (t, J = 11.2 Hz, 1H), 3.31 (s, 3H), 3.40-3.48 (m, 1H), 4.06 (d, J = 13.6 Hz, 1H), 4.24 (d, J = 10.0 Hz, 1H), 4.68-4.76 (m, 1H), 5.23 (s, 1H), 5.34 (d, J = 13.6 Hz, 1H), 5.78 (d, J = 7.6 Hz, 1H), 6.68 (d, J = 7.6 Hz, 1H), 6.84 (t, J = 7.6 Hz, 1H), 6.95-7.00 (m, 1H), 7.03-7.15 (m, 4H). |
| III-40 | 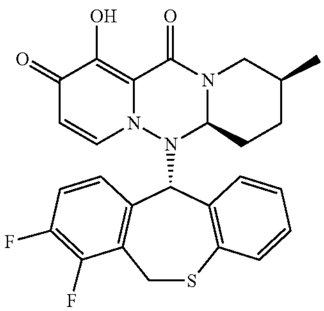 [SMILES: C[C@H]1CC[C@@H]2N(C1)C(=O)c1c(O)c(=O)ccn1N2[C@@H]1c2ccccc2SCc2c1ccc(F)c2F] | 1H-NMR (CDCl3) δ: 0.94 (3H, d, J = 7.2 Hz), 1.45-1.86 (5H, m), 1.86-2.12 (1H, m), 2.79 (1H, dd, J = 13.3, 3.5 Hz), 4.05 (1H, d, J = 13.7 Hz), 4.27 (1H, dd, J = 11.6, 2.4 Hz), 4.56 (1H, d, J = 13.2 Hz), 5.36 (1H, dd, J = 13.6, 2.4 Hz), 5.20 (1H, s), 5.79 (1H, d, J = 7.7 Hz), 6.69 (1H, d, J = 7.4 Hz), 6.81-6.87 (1H, m), 6.95-7.01 (1H, m), 7.05-7.14 (4H, m). |
| III-41 | 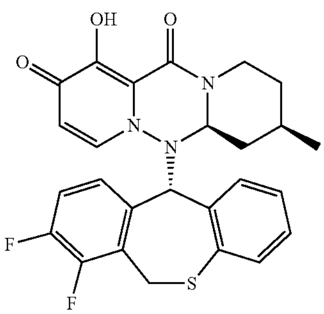 [SMILES: C[C@@H]1CCN2C(=O)c3c(O)c(=O)ccn3N([C@@H]3c4ccccc4SCc4c3ccc(F)c4F)[C@@H]2C1] | 1H-NMR (CDCl3) δ: 0.96 (3H, d, J = 6.5 Hz), 1.16-1.20 (1H, m), 1.34-1.40 (1H, m), 1.64-1.79 (3H, m), 1.85-1.89 (1H, m), 2.52 (1H, td, J = 13.1, 2.6 Hz), 4.05 (1H, d, J = 13.8 Hz), 4.28 (1H, dd, J = 11.5, 2.2 Hz), 4.70 (1H, dd, J = 13.3, 3.6 Hz), 5.23 (1H, s), 5.36 (1H, dd, J = 13.7, 2.4 Hz), 5.79 (1H, d, J = 7.8 Hz), 6.68 (1H, d, J = 7.5 Hz), 6.82-6.86 (1H, m), 6.98 (1H, dd, J = 8.3, 5.3 Hz), 7.02-7.15 (4H, m). |

TABLE 7

| No. | Structure | H-NMR or LC/MS |
|---|---|---|
| III-42 | 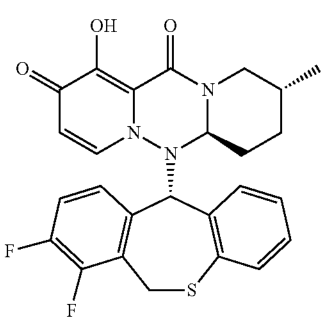 | 1H-NMR (CDCl3) δ: 0.91 (3H, d, J = 6.6 Hz), 1.22-1.29 (2H, m), 1.57-1.87 (5H, m), 1.96 (1H, d, J = 13.6 Hz), 2.18 (1H, t, J = 12.4 Hz), 4.05 (1H, d, J = 13.9 Hz), 4.25 (1H, dd, J = 11.4, 2.5 Hz), 4.57-4.65 (1H, m), 5.22 (1H, s), 5.35 (1H, dd, J = 13.8, 2.4 Hz), 5.78 (1H, d, J = 7.6 Hz), 6.68 (1H, d, J = 7.8 Hz), 6.82-6.86 (1H, m), 6.94-7.01 (1H, m), 7.03-7.15 (4H, m). |

TABLE 7-continued

| No. | Structure | H-NMR or LC/MS |
|---|---|---|
| III-43 | 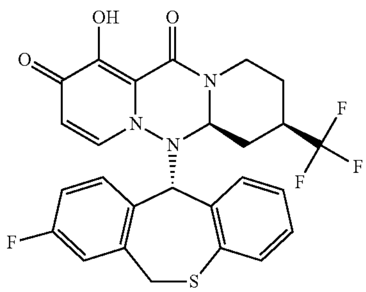 [SMILES: O=C1c2c(O)c(=O)ccn2N([C@H]2c3ccc(F)cc3CSc3ccccc32)[C@@H]2C[C@H](C(F)(F)F)CCN12] | 1H-NMR (CDCl3) δ: 1.55 (1H, ddd, J = 26.3, 13.0, 4.6 Hz), 1.74 (1H, q, J = 12.3 Hz), 1.89 (1H, d. J = 13.1 Hz), 2.09 (1H, d, J = 12.7 Hz), 2.58 (1H, td, J = 13.2, 2.6 Hz), 2.40-2.52 (1H, m), 3.54 (1H, d, J = 13.4 Hz), 4.35 (1H, dd, J = 11.7, 2.3 Hz), 4.84 (1H, dd, J = 13.4, 3.8 Hz), 5.23 (1H, s), 5.57 (1H, d, J = 13.4 Hz), 5.80 (1H, d, J = 7.7 Hz), 6.69 (1H, d, J = 7.7 Hz), 6.82-6.86 (1H, m), 6.98 (1H, td, J = 8.2, 2.6 Hz), 7.07-7.14 (4H, m), 7.20 (1H, dd, J = 8.3, 5.5 Hz). |
| III-44 | 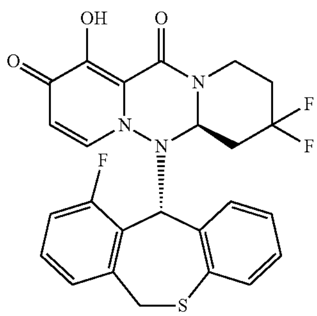 [SMILES: O=C1c2c(O)c(=O)ccn2N([C@@H]2c3ccccc3SCc3cccc(F)c32)[C@@H]2CC(F)(F)CCN12] | 1H-NMR(CDCl3)δ: 1.83-2.00 (m, 1H), 2.08-2.23 (m, 2H), 2.37 (t, J = 13.6 Hz, 1H), 2.74 (t, J = 13.2 Hz, 1H), 3.63 (d, J = 13.6 Hz, 1H), 4.51 (d, J = 11.6 Hz, 1H), 4.76-4.84 (m, 1H), 5.54 (d, J = 13.2 Hz, 1H), 5.79 (d, J = 8.0 Hz, 1H), 5.87 (s, 1H), 6.77 (d, J = 7.2 Hz, 1H), 6.85 (t, J = 7.2 Hz, 1H), 7.04-7.18 (m, 5H), 7.35-7.43 (m, 1H). |
| III-45 | 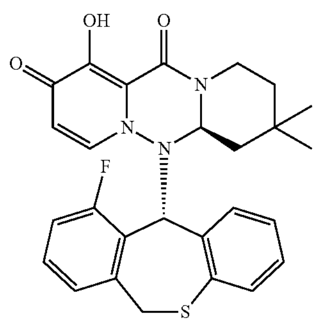 [SMILES: CC1(C)CCN2C(=O)c3c(O)c(=O)ccn3N([C@@H]3c4ccccc4SCc4cccc(F)c43)[C@@H]2C1] | 1H-NMR(CDCl3)δ: 0.82 (s, 3H), 0.96 (s, 3H), 1.30-1.61 (m, 4H), 2.71 (t, J = 13.2 Hz, 1H), 1.99 (d, J = 12.8 Hz, 1H), 2.54 (t, J = 12.8 Hz, 1H), 4.04 (d, J = 13.6 Hz, 1H), 4.27 (dd, J = 2.0 Hz, 11.2 Hz, 1H), 4.69-4.74 (m, 1H), 5.23 (s, 1H), 5.35 (dd, J = 2.4 Hz, 13.6 Hz, 1H), 5.77 (d, J = 7.6 Hz, 1H), 6.68 (d, J = 7.6 Hz, 1H), 6.80-6.86 (m, 1H), 6.95-7.00 (m, 1H), 7.03-7.14 (m, 4H). |
| III-46 | 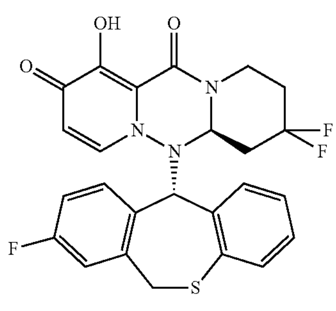 [SMILES: O=C1c2c(O)c(=O)ccn2N([C@H]2c3ccc(F)cc3CSc3ccccc32)[C@@H]2CC(F)(F)CCN12] | 1H-NMR(CDCl3)δ: 1.83-2.00 (m, 1H), 2.07-2.27 (m, 2H), 2.37 (t, J = 13.2 Hz, 1H), 2.67 (t, J = 13.2 Hz, 1H), 3.54 (d, J = 13.2 Hz, 1H), 4.51 (d, J = 11.2 Hz, 1H), 4.75-4.82 (m, 1H), 5.24 (s, 1H), 5.50 (d, J = 13.2 Hz, 1H), 5.77 (d, J = 7.2 Hz, 1H), 6.68 (d, J = 7.6 Hz, 1H), 6.80-6.86 (m, 1H), 6.95-7.02 (m, 1H), 7.05-7.14 (m, 4H), 7.16-7.23 (m, 1H) |
| III-47 | 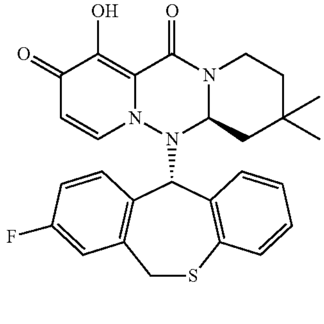 [SMILES: CC1(C)CCN2C(=O)c3c(O)c(=O)ccn3N([C@H]3c4ccc(F)cc4CSc4ccccc43)[C@@H]2C1] | 1H-NMR(CDCl3)δ: 0.82 (s, 3H), 0.97 (s, 3H), 1.24-1.44 (m, 2H), 1.46-1.60 (m, 2H), 2.58-2.68 (m, 1H), 3.50 (d, J = 13.2 Hz, 1H), 4.44 (dd, J = 2.8 Hz, 11.6 Hz, 1H), 4.57 (dd, J = 2.8 Hz, 13.2 Hz, 1H), 5.23 (s, 1H), 5.58 (d, J = 13.6 Hz, 1H), 5.78 (d, J = 7.6 Hz, 1H), 6.68 (d, J = 7.6 Hz, 1H), 6.80-6.86 (m, 1H), 6.95-7.03 (m, 2H), 7.05-7.13 (m, 3H), 7.18-7.24 (m, 1H). |

TABLE 7-continued

| No. | Structure | H-NMR or LC/MS |
|---|---|---|
| III-48 | 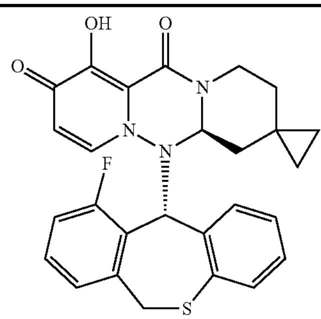 | 1H-NMR(CDCl3)δ: 0.10-0.16 (m, 1H), 0.25-0.31 (m, 1H), 0.36-0.49 (m, 2H), 0.79 (d, J = 14.0 Hz, 1H), 0.99 (d, J = 12.8 Hz, 1H), 1.92-2.03 (m, 1H), 2.18 (t, J = 12.0 Hz, 1H), 2.65-2.77 (m, 1H), 3.58 (d, J = 13.6 Hz, 1H), 4.45 (dd, J = 2.4 Hz, 11.6 Hz, 1H), 4.73 (dd, J = 3.6 Hz, 13.2 Hz, 1H), 5.58 (d, J = 13.6 Hz, 1H), 5.81 (d, J = 7.6 Hz, 1H), 5.88 (s, 1H), 6.78 (d, J = 7.2 Hz, 1H), 6.81-6.88 (m, 1H), 7.05-7.16 (m, 5H), 7.34-7.43 (m, 1H). |

TABLE 8

| No. | Structure | H-NMR or LC/MS |
|---|---|---|
| III-49 | 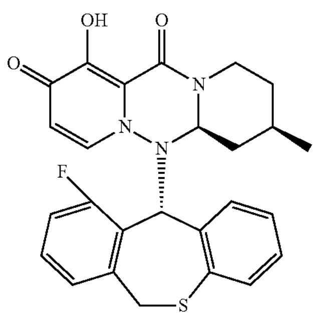 [SMILES: C[C@@H]1CCN2C(=O)c3c(O)c(=O)ccn3N([C@@H]3c4ccccc4SCc4cccc(F)c43)[C@@H]2C1] | 1H-NMR (CDCl3) δ: 0.95 (d, J = 6.5 Hz, 3H), 1.12-1.24 (m, 1H), 1.36 (dd, J = 24.1, 11.7 Hz, 1H), 1.48-1.75 (m, 2H), 1.86 (d, J = 12.7 Hz, 1H), 2.59 (td, J = 13.1, 2.8 Hz, 1H), 3.59 (d, J = 13.3 Hz, 1H), 4.28 (dd, J = 11.5, 2.4 Hz, 1H), 4.73 (dd, J = 13.6, 3.0 Hz, 1H), 5.66 (d, J = 13.3 Hz, 1H), 5.79 (d, J = 7.7 Hz, 1H), 5.85 (s, 1H), 6.77-6.79 (m, 1H), 6.82-6.86 (m, 1H), 7.03-7.11 (m, 3H), 7.14 (d, J = 7.7 Hz, 2H), 7.36 (td, J = 8.0, 5.5 Hz, 1H). |
| III-50 | 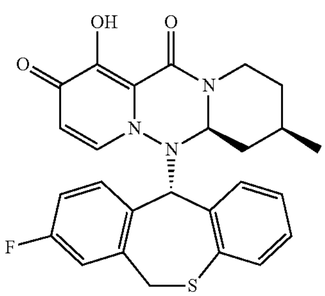 [SMILES: C[C@@H]1CCN2C(=O)c3c(O)c(=O)ccn3N([C@H]3c4ccc(F)cc4CSc4ccccc43)[C@@H]2C1] | 1H-NMR (CDCl3) δ: 0.95 (d, J = 6.5 Hz, 3H), 1.12-1.28 (m, 1H), 1.36 (q, J = 12.0 Hz, 1H), 1.63-1.78 (m, 3H), 1.86 (d, J = 12.8 Hz, 1H), 2.52 (td, J = 13.1, 2.8 Hz, 1H), 3.51 (d, J = 13.4 Hz, 1H), 4.28 (dd, J = 11.6, 2.3 Hz, 1H), 4.69 (dd, J = 13.5, 3.3 Hz, 1H), 5.22 (s, 1H), 5.62 (d, J = 13.4 Hz, 1H), 5.78 (d, J = 7.7 Hz, 1H), 6.68 (d, J = 7.7 Hz, 1H), 6.81-6.85 (m, 1H), 6.97 (td, J = 8.3, 2.6 Hz, 1H), 7.05-17.10 (m. 4H), 7.20 (dd, J = 8.4, 5.4 Hz, 1H). |
| III-51 | 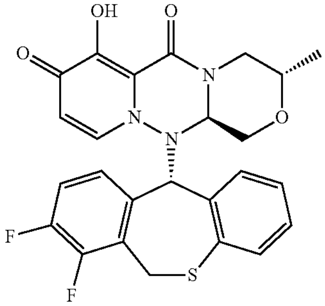 [SMILES: C[C@H]1CN2C(=O)c3c(O)c(=O)ccn3N([C@@H]3c4ccccc4SCc4c3ccc(F)c4F)[C@@H]2CO1] | 1H-NMR (CDCl3) δ: 1.17 (d, J = 6.1 Hz, 3H), 2.61 (dd, J = 13.3, 10.7 Hz, 1H), 3.54-3.59 (m, 1H), 3.64 (t, J = 10.6 Hz, 1H), 3.96 (dd, J = 11.1, 2.9 Hz, 1H), 4.07 (d, J = 13.8 Hz, 1H), 4.54 (dd, J = 10.0, 2.9 Hz, 1H), 4.64 (dd, J = 13.4, 2.3 Hz, 1H), 5.26-5.30 (m, 2H), 5.75 (d, J = 7.7 Hz, 1H), 6.68 (d, J = 7.7 Hz, 1H), 6.85 (t, J = 7.2 Hz, 1H), 6.98-7.03 (m, 2H), 7.07-7.15 (m, 3H). |

TABLE 8-continued

| No. | Structure | H-NMR or LC/MS |
|---|---|---|
| III-52 | 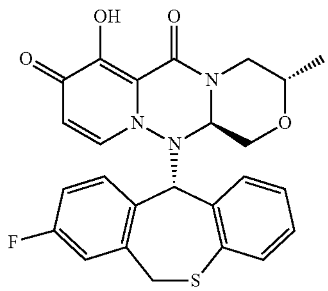 | 1H-NMR(CDCl3)δ: 1.16 (d, J = 6.0 Hz, 3H), 2.55-2.65 (m, 1H), 3.48-3.60 (m, 2H), 3.64 (t, J = 10.4 Hz, 1H), 3.94 (dd, J = 2.8 Hz, 11.2 Hz, 1H), 4.54 (dd, J = 2.8 Hz, 10.0 Hz, 1H), 4.62 (dd, J = 2.0 Hz, 13.6 Hz, 1H), 5.25 (s, 1H), 5.54 (d, J = 13.2 Hz, 1H), 5.74 (d, J = 7.2 Hz, 1H), 6.68 (d, J = 7.2 Hz, 1H), 6.79-6.86 (m, 1H), 6.96-7.05 (m, 2H), 7.05-7.15 (m, 3H), 7.17-7.24 (m, 1H). |

TABLE 9

| No. | Structure | H-NMR or LC/MS |
|---|---|---|
| III-53 | 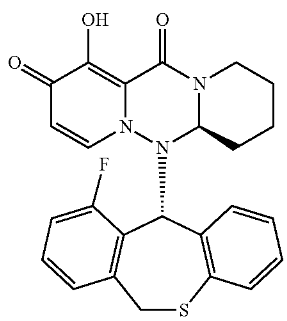 [SMILES: O=C1c2c(O)c(=O)ccn2N([C@@H]2c3ccccc3SCc3cccc(F)c32)[C@@H]2CCCCN12] | 1H-NMR (CDCl3) δ: 1.45-1.74 (m, 4H), 1.85 (d, J = 12.0 Hz, 1H), 1.95-2.02 (m, 1H), 2.61 (t, J = 12.4 Hz, 1H), 3.58 (d, J = 14.0 Hz, 1H), 4.27 (d, J = 10.8 Hz, 1H), 4.74 (d, J = 12.4 Hz, 1H), 5.65 (d, J = 14.0 Hz, 1H), 5.78 (d, J = 6.8 Hz, 1H), 5.85 (s, 1H), 6.75-6.88 (m, 2H), 7.02-7.15 (m, 5H), 7.34-7.40 (m, 1H). |
| III-54 | 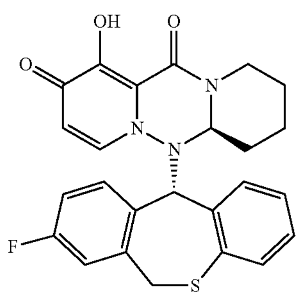 | 1H-NMR(CDCl3)δ: 1.47-2.05(m, 6H), 2.50-2.58(m, 1H), 3.51(d, J = 12.0 Hz, 1H), 4.26-4.31(m, 1H), 4.68-4.74(m, 1H), 5.22(s, 1H), 5.62(d, J = 13.6 Hz, 1H), 5.77(d, J = 7.6 Hz, 1H), 6.68(d, J = 7.6 Hz, 1H), 6.80-6.82(m, 1H), 6.88-7.02(m, 1H), 7.03-7.15(m, 5H) |
| III-55 | 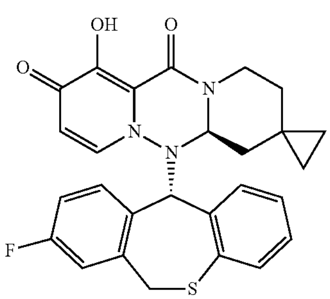 [SMILES: O=C1c2c(O)c(=O)ccn2N([C@H]2c3ccc(F)cc3CSc3ccccc32)[C@@H]2CC3(CCN12)CC3] | 1H-NMR (CDCl3) δ: 0.12-0.18 (m, 1H), 0.25-0.31 (m, 1H), 0.36-0.49 (m, 2H), 0.78 (d, J = 14.0 Hz, 1H), 0.99 (d, J = 12.4 Hz, 1H), 1.92-2.00 (m, 1H), 2.18 (t, J = 11.6 Hz, 1H), 2.58-2.68 (m, 1H), 3.48 (d, J = 13.2 Hz, 1H), 4.44 (dd, J = 2.0 Hz, 11.6 Hz, 1H), 4.70 (dd, J = 3.2 Hz, 12.8 Hz, 1H), 5.24 (s, 1H), 5.53 (d, J = 13.6 Hz, 1H), 5.77 (d, J = 8.0 Hz, 1H), 6.89 (d, J = 7.2 Hz, 1H), 6.80-6.87 (m, 1H), 6.95-7.02 (m, 2H), 7.03-7.14 (m, 3H), 7.20-7.26 (m, 1H). |

TABLE 9-continued

| No. | Structure | H-NMR or LC/MS |
|---|---|---|
| III-56 | 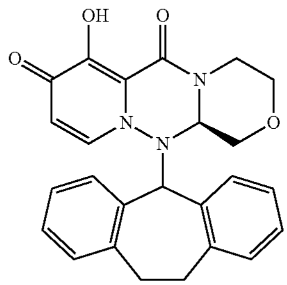 [SMILES: O=C1c2c(O)c(=O)ccn2N(C2c3ccccc3CCc3ccccc32)[C@@H]2COCCN12] | (CDCl3) δ: 7.36 (1H, t, J = 6.9 Hz), 7.29-7.19 (4H, m), 7.16 (1H, d, J = 7.8 Hz), 6.95 (1H, t, J = 7.2 Hz), 6.68 (1H, d, J = 7.5 Hz), 6.54 (1H, d, J = 7.7 Hz), 5.69 (1H, d, J = 7.4 Hz), 5.15 (1H, s), 4.63 (1H, d, J = 13.1 Hz), 4.48 (1H, d, J = 9.7 Hz), 3.94-3.85 (2H, m), 3.79-3.69 (2H, m), 3.50-3.39 (2H, m), 3.02 (1H, t, J = 13.7 Hz), 2.92 (2H, t, J = 11.7 Hz). |
| III-57 | 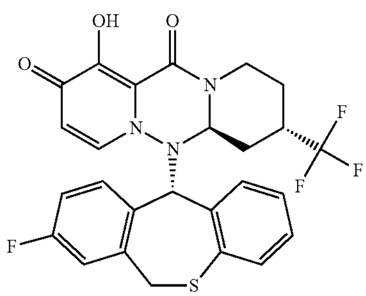 [SMILES: O=C1c2c(O)c(=O)ccn2N([C@H]2c3ccc(F)cc3CSc3ccccc32)[C@@H]2C[C@@H](C(F)(F)F)CCN12] | 1H-NMR: 7.20 (dd, J = 8.6, 5.5 Hz, 1H), 7.14-7.08 (m, 3H), 7.03-6.97 (m, 2H), 6.85-6.82 (m, 1H), 6.68 (d, J = 7.7 Hz, 1H), 5.81 (d, J = 7.5 Hz, 1H), 5.53 (d, J = 13.6 Hz, 1H), 5.21 (s, 1H), 4.69-4.63 (m, 1H), 3.54 (d, J = 13.6 Hz, 1H), 2.85-2.80 (m, 1H), 2.66 (brs, 1H), 2.15-2.00 (m, 2H), 1.95-1.80 (m, 2H) |
| III-58 | 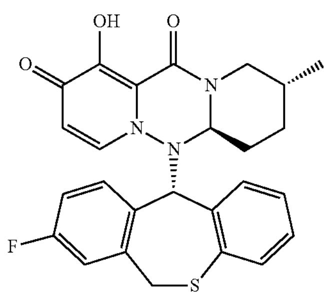 [SMILES: C[C@@H]1CC[C@@H]2N(C1)C(=O)c1c(O)c(=O)ccn1N2[C@H]1c2ccc(F)cc2CSc2ccccc21] | 1H-NMR (CDCl3) δ: 0.90 (d, J = 6.5 Hz, 3H), 1.23 (ddd, J = 25.6, 12.8, 4.1 Hz, 1H), 1.63-1.86 (m, 3H), 1.95 (d, J = 13.7 Hz, 1H), 2.17 (t, J = 12.3 Hz, 1H), 3.51 (d, J = 13.4 Hz, 1H), 4.25 (d, J = 11.0 Hz, 1H), 4.60 (d, J = 12.0 Hz, 1H), 5.21 (s, 1H), 5.61 (d, J = 13.3 Hz, 1H), 5.78 (d, J = 7.7 Hz, 1H), 6.68 (d, J = 7.8 Hz, 1H), 6.83 (t, J = 6.7 Hz, 1H), 6.99 (t, J = 8.2 Hz, 1H), 7.05-7.09 (m, 4H), 7.20 (dd, J = 8.1, 5.7 Hz, 1H). |
| III-59 | 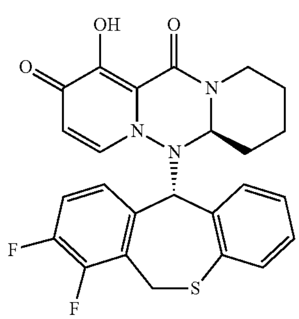 [SMILES: O=C1c2c(O)c(=O)ccn2N([C@@H]2c3ccccc3SCc3c2ccc(F)c3F)[C@@H]2CCCCN12] | 1H-NMR (CDCl3) δ: 1.45-1.79 (m, 4H), 1.87 (d, J = 10.8 Hz, 1H), 1.99 (d, J = 12.8 Hz, 1H), 2.54 (t, J = 12.8 Hz, 1H), 4.04 (d, J = 13.6 Hz, 1H), 4.27 (dd, J = 2.0 Hz, 11.2 Hz, 1H), 4.69-4.74 (m, 1H), 5.23 (s, 1H), 5.35 (dd, J = 2.4 Hz, 13.6 Hz, 1H), 5.77 (d, J = 7.6 Hz, 1H), 6.68 (d, J = 7.6 Hz, 1H), 6.80-6.86 (m, 1H), 6.95-7.00 (m, 1H), 7.03-7.14 (m, 4H). |

Example 4

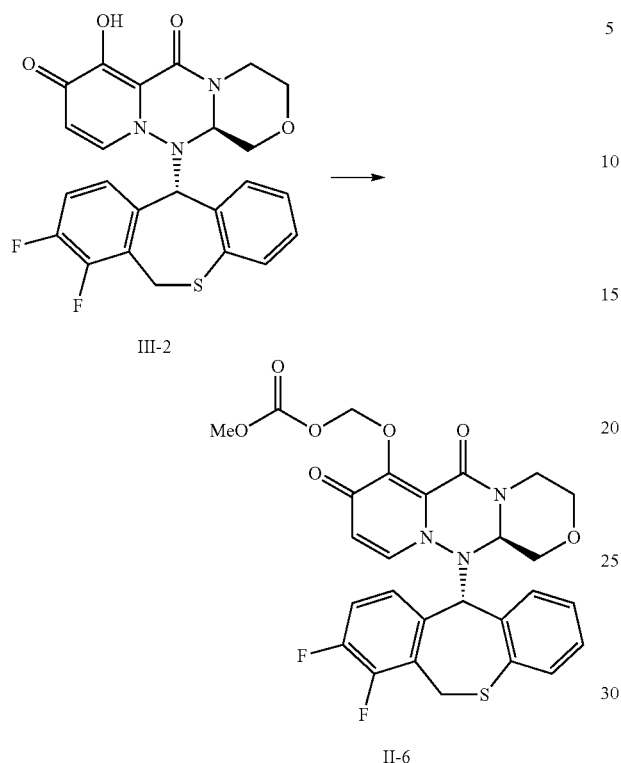

To a suspension of Compound III-2 (1.00 g, 2.07 mmol) in DMA (5 ml) were added chloromethyl methyl carbonate (0.483 g, 3.10 mmol), potassium carbonate (0.572 g, 4.14 mmol) and potassium iodide (0.343 g, 2.07 mmol) and the mixture was stirred at 50° C. for 6 hours. To the mixture was added DMA (1 ml) and the mixture was stirred for 6 hours. The mixture was cooled to room temperature, DMA (6 ml) was added thereto, and the mixture was stirred at 50° C. for 5 minutes. The mixture was filtered. To the obtained filtrate were added 1 mol/L aqueous solution of hydrochloric acid (10 ml) and water (4 ml) and the mixture was stirred for 1 hour. The precipitated solid was filtered and dried under reduced pressure at 60° C. for 3 hours to obtain Compound II-6 (1.10 g, 1.93 mmol, 93%).

1H-NMR (DMSO-D6) δ: 2.91-2.98 (1H, m), 3.24-3.31 (1H, m), 3.44 (1H, t, J=10.4 Hz), 3.69 (1H, dd, J=11.5, 2.8 Hz), 3.73 (3H, s), 4.00 (1H, dd, J=10.8, 2.9 Hz), 4.06 (1H, d, J=14.3 Hz), 4.40 (1H, d, J=11.8 Hz), 4.45 (1H, dd, J=9.9, 2.9 Hz), 5.42 (1H, dd, J=14.4, 1.8 Hz), 5.67 (1H, d, J=6.5 Hz), 5.72-5.75 (3H, m), 6.83-6.87 (1H, m), 7.01 (1H, d, J=6.9 Hz), 7.09 (1H, dd, J=8.0, 1.1 Hz), 7.14-7.18 (1H, m), 7.23 (1H, d, J=7.8 Hz), 7.37-7.44 (2H, m).

Example 5

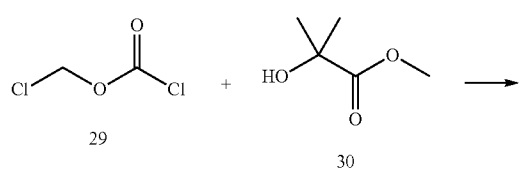

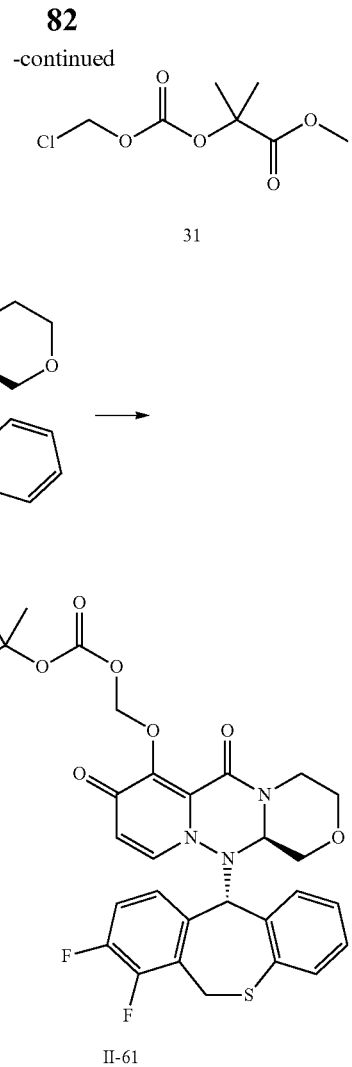

First Step

To a solution of chloromethyl chloroformate (300 mg, 2.33 mmol) and Compound 30 (330 mg, 2.79 mmol) in dichloromethane (6.0 mL) was added pyridine (207 μL, 2.56 mmol) at 00° C. under nitrogen atmosphere, and the mixture was stirred at 0° C. for 30 minutes, was warmed up to room temperature and was stirred for 1 hour. To the mixture was added 2 mol/L aqueous solution of hydrochloric acid and the mixture was extracted with dichloromethane. The obtained organic layer was washed with brine, dried over anhydrous magnesium sulfate, and concentrated under reduced pressure to obtain Compound 31 (440 mg, 90%).

1H-NMR (CDCl3) δ: 1.65 (s, 6H), 3.77 (s, 3H), 5.71 (s, 2H).

Second Step

Compound III-2 (300 mg, 0.62 mmol), potassium carbonate (172 mg, 1.24 mmol), potassium iodide (103 mg, 0.62 mmol) and Compound 31 (261 mg, 1.24 mmol) were dissolved in DMA (3.0 mL) and the mixture was stirred at 80° C. for 3 hours. To the mixture was added 2 mol/L aqueous solution of hydrochloric acid and the mixture was extracted with ethyl acetate. The obtained organic layer was washed with brine, dried over anhydrous magnesium sulfate, and concentrated under reduced pressure. The obtained residue was purified by silica gel column chromatography (chloroform-methanol) to obtain Compound II-61 (350 mg, 86%).

1H-NMR (CDCl3) δ: 1.63 (s, 3H), 1.67 (s, 3H), 2.86-2.93 (m, 1H), 3.38-3.61 (m, 2H), 3.68-3.78 (m, 4H), 3.90-3.96 (m, 1H), 4.06 (d, J=14.0 Hz, 1H), 4.51 (dd, J=2.0 Hz, 9.6 Hz, 1H), 4.65 (d, J=12.4 Hz, 1H), 5.21 (d, J=14.4 Hz, 1H), 5.36 (s, 1H), 5.80-5.95 (m, 3H), 6.85-6.92 (m, 2H), 7.03-7.22 (m, 5H).

Example 6

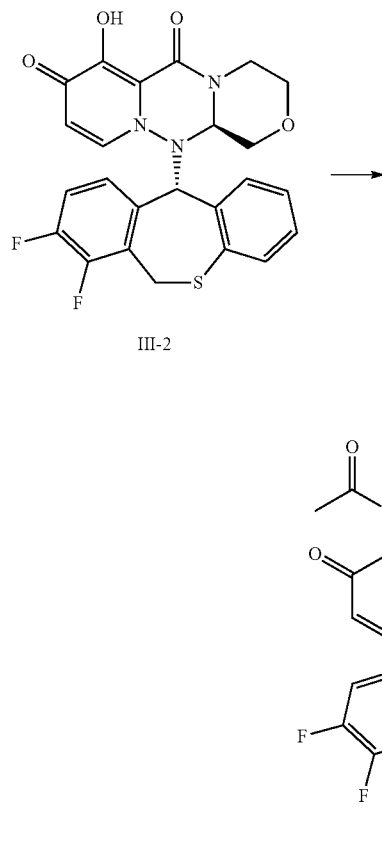

III-2

II-4

To a solution of Compound III-2 (90 mg, 0.186 mmol) in dichloromethane (2 mL) were added acetic anhydride (0.053 mL, 0.558 mmol), triethylamine (0.077 mL, 0.558 mmol) and a catalytic amount of DMAP, and the mixture was stirred at room temperature for 2 hours. The mixture was concentrated under reduced pressure and the obtained residue was purified by silica gel column chromatography (chloroform-methanol). To the obtained solution was added ether and the precipitated solid was filtered to obtain Compound II-4 (71 mg, 73%).

1H-NMR (CDCl3) δ: 2.46 (s, 3H), 2.88-2.99 (m, 1H), 3.35-3.50 (m, 1H), 3.60-3.65 (m, 1H), 3.75-3.83 (m, 1H), 3.90-4.00 (m, 1H), 4.05 (d, J=14.0 Hz, 1H), 4.52-4.57 (m, 1H), 4.60-4.70 (m, 1H), 5.24-5.34 (m, 1H), 5.35 (s, 1H), 5.88 (d, J=7.6 Hz, 1H), 6.85-6.82 (m, 1H), 6.90-7.05 (m, 2H), 7.06-7.20 (m, 4H)

LC/MS (ESI): m/z=526.2 [M+H]+, RT=1.87 min, method (1)

Example 7

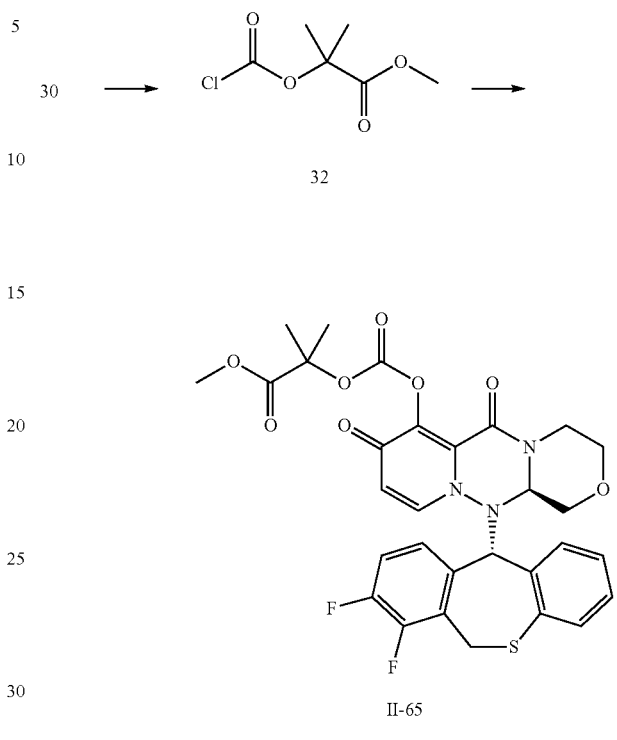

30 → 32 →

II-65

First Step

To a solution of triphosgene (300 mg, 2.54 mmol) in dichloromethane (6.0 mL) was added pyridine (257 μL, 3.17 mmol) at 0° C. under nitrogen atmosphere and the mixture was stirred for 15 minutes. To the mixture was added a solution of Compound 30 (377 mg, 1.27 mmol) in dichloromethane (1.0 mL), and the mixture was stirred at 0° C. for 15 minutes, warmed up to room temperature and stirred for 15 minutes. The mixture was concentrated under reduced pressure, ethyl acetate (4.0 mL) was added thereto, and the mixture was filtered. The filtrate was concentrated under reduced pressure to obtain Compound 32 (380 mg).

Second Step

To a solution of Compound III-2 (350 mg, 0.724 mmol) in dichloromethane (3.5 mL) were added Compound 32 (196 mg, 1.09 mmol) and triethylamine (301 μL, 2.17 mmol) at 0° C. and the mixture was stirred at 0° C. for 30 minutes. To the mixture was added 2 mol/L aqueous solution of hydrochloric acid and the mixture was extracted with dichloromethane. The obtained organic layer was washed with brine, dried over anhydrous magnesium sulfate, and concentrated under reduced pressure. The obtained residue was purified by silica gel column chromatography (chloroform-methanol) to obtain Compound II-65 (380 mg, 84%).

1H-NMR (CDCl3) δ: 1.73 (s, 3H), 1.77 (s, 3H), 2.90-2.99 (m, 1H), 3.37-3.43 (m, 1H), 3.57 (t, J=8.8 Hz, 1H), 3.76 (dd, J=2.8 Hz, 12.0 Hz, 1H), 3.81 (s, 3H), 3.94 (d d, J=2.8 Hz, 10.8 Hz, 1H), 4.05 (d, J=14.0 Hz, 1H), 4.55 (dd, J=2.8 Hz, 9.6 Hz, 1H), 4.65 (d, J=12.0 Hz, 1H), 5.28 (d, J=12.0 Hz, 1H), 5.34 (s, 1H), 5.89 (d, J=8.0 Hz, 1H), 6.86-6.95 (m, 2H), 7.03-7.15 (m, 5H).

Example 8

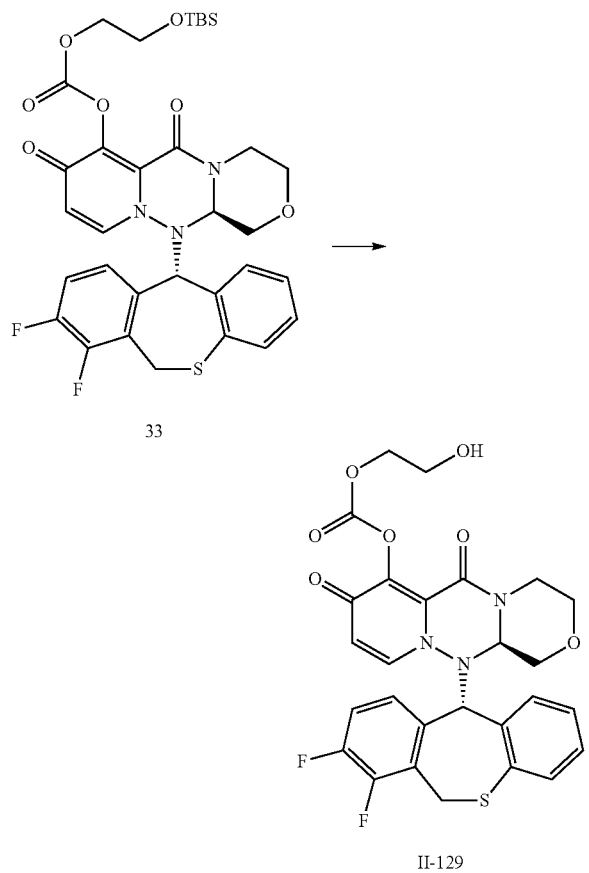

To a solution of Compound 33 (276 mg, 0.402 mmol) in THF (1 mL) were added acetic acid (121 mg, 2.01 mmol) and 1 mol/L TBAF in THF (1.21 mL, 1.21 mmol) under ice-water bath and the mixture was stirred at room temperature for 4 hours. The mixture was concentrated under reduced pressure. The obtained residue was purified by silica gel column chromatography (ethyl acetate-methanol) to obtain Compound II-129 (179 mg, 78%).

LC/MS (ESI): m/z=572.0 [M+H]$^+$, RT=1.74 min, method (2)

Example 9

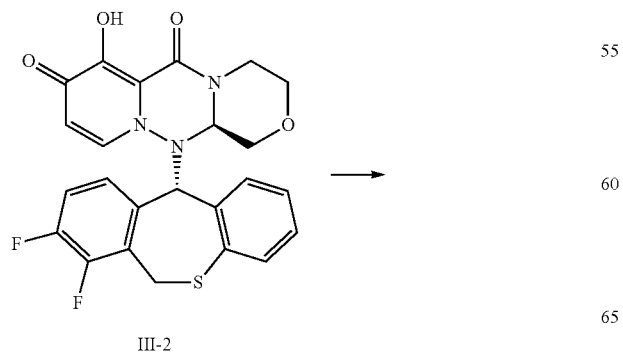

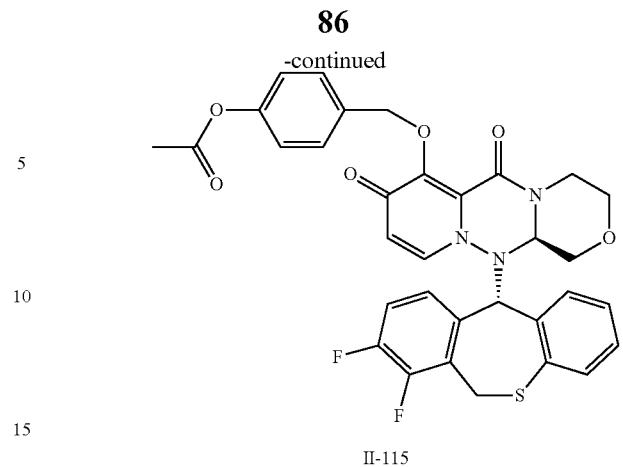

To a solution of Compound III-2 (300 mg, 0.62 mmol) in DMF (4 mL) were added potassium carbonate (258 mg, 1.87 mmol), 4-(chloromethyl)phenyl acetate (344 mg, 1.87 mmol) and sodium iodide (139 mg, 1.87 mmol) at room temperature and the mixture was stirred at 65° C. for 1 hour. To the mixture was added water and the mixture was extracted with ethyl acetate. The obtained organic layer was washed with water, dried over anhydrous sodium sulfate, and concentrated under reduced pressure. The obtained residue was purified by silica gel column chromatography (ethyl acetate-methanol) to obtain Compound II-115 (120 mg, 31%).

LC/MS (ESI): m/z=631.95 [M+H]$^+$, RT=2.07 min, method (2)

Example 10

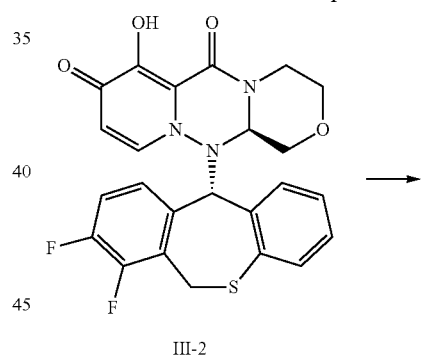

To a solution of Compound III-2 (150 mg, 0.31 mmol) in dichloromethane (2 mL) 3 mmol/g triphenylphosphine supported on polymer (310 mg, 0.93 mmol), pyridin-4-ylmethanol (68 mg, 0.62 mmol) and 40% DEAD in toluene (270 mg, 0.62 mmol) at room temperature and the mixture was stirred at room temperature for 30 minutes. The mixture was purified by amino column chromatography (ethyl acetate-methanol) to obtain Compound II-143 (63 mg, 35%).

LC/MS (ESI): m/z=575.00 [M+H]$^+$, RT=1.43 min, method (2)

Example 11

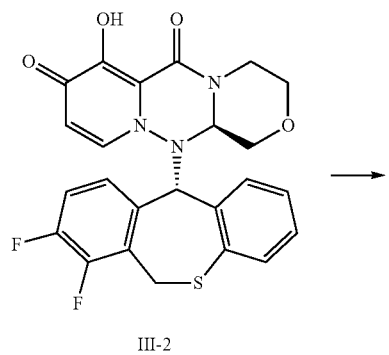

III-2

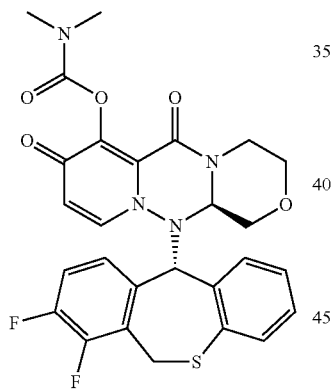

II-27

To a solution of Compound III-2 (65 mg, 0.134 mmol) in pyridine (0.8 mL) was added dimethylcarbamoyl chloride (21.7 mg, 0.202 mmol) and the mixture was stirred at 80° C. over night. To the mixture was added 1 mol/L aqueous solution of hydrochloric acid and the mixture was extracted with ethyl acetate. The obtained organic layer was washed with brine, dried over anhydrous magnesium sulfate, and concentrated under reduced pressure. The obtained residue was solidified with ethyl acetate-hexane to obtain Compound II-27 (65 mg, 87%).

1H-NMR (CDCl3) δ: 2.89 (t, J=11.2 Hz, 1H), 2.99 (s, 1H), 3.01 (s, 3H), 3.18-3.26 (m, 4H), 3.45 (t, J=10.8 Hz, 1H), 3.59 (t, J=10.8 Hz, 1H), 3.70-3.80 (m, 1H), 3.90-3.98 (m, 1H), 4.03 (d, J=13.6 Hz, 1H), 4.50-4.70 (m, 2H), 5.21-5.35 (m, 2H), 5.82 (d, J=7.6 Hz, 1H), 6.91 (t, J=7.6 Hz, 1H), 7.00-7.20 (m, 6H).

Example 12

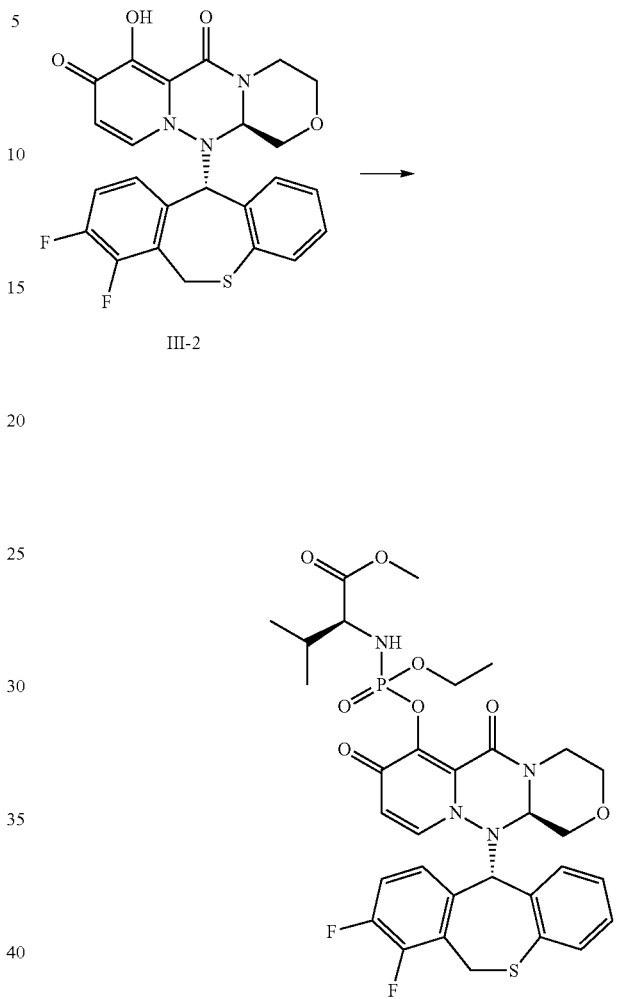

To a solution of ethyl phosphorodichloridate (135 mg, 0.829 mmol) in dichloromethane (3 mL) was added L-valine methyl ester hydrochloride (139 mg, 0.829 mmol) and then added dropwise a solution of triethylamine (168 mg, 1.66 mmol) in dichloromethane (2 mL) at −78° C. The mixture was stirred at room temperature for 1 hour. Compound III-2 (200 mg, 0.414 mmol) and triethylamine (126 mg, 1.25 mmol) were added thereto, and the mixture was stirred at same temperature for 6 hours. The mixture was concentrated and the obtained residue was purified by silica gel column chromatography (ethyl acetate-methanol) to obtain Compound II-55 (112 mg, 38%).

LC/MS (ESI): m/z=705.05 [M+H]$^+$, RT=2.18 min, method (2)

Example 13

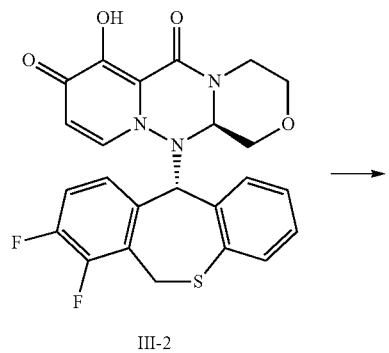

III-2

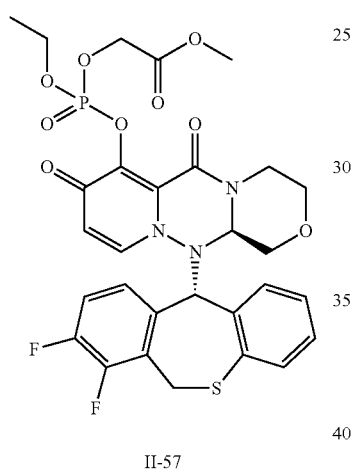

II-57

Example 14

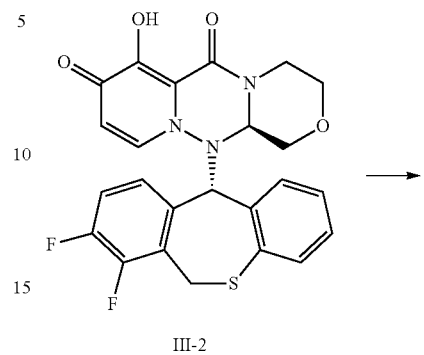

III-2

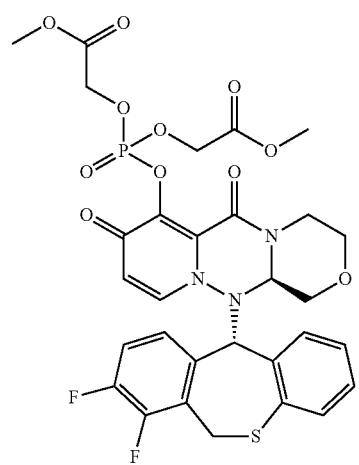

II-58

To a solution of ethyl phosphorodichloridate (202 mg, 1.24 mmol) in dichloromethane (3 mL) was added dropwise a mixture of triethylamine (126 mg, 1.24 mmol) and methyl glycolate (112 mg, 1.24 mmol) in dichloromethane (2 mL). The mixture was stirred at room temperature for 2 hours. Compound III-2 (200 mg, 0.414 mmol) and triethylamine (126 mg, 1.25 mmol) were added thereto and the mixture was stirred at same temperature for 1 hour. The mixture was concentrated and the obtained residue was purified by silica gel column chromatography (ethyl acetate-methanol) to obtain Compound II-57 (143 mg, 52%).

LC/MS (ESI): m/z=664.00 [M+H]$^+$, RT=1.93 min, method (2)

To a solution of phosphoryl chloride (1.53 g, 10 mmol) in dichloromethane (10 mL) was added dropwise the mixture of triethylamine (2.12 g, 20.95 mmol) and methyl glycolate (1.89 mg, 21 mmol) in dichloromethane (5 mL). The mixture was stirred at room temperature for 2 hours. To the mixture (2 mL) were added Compound III-2 (200 mg, 0.414 mmol) and triethylamine (126 mg, 1.25 mmol) and the mixture was stirred at same temperature for 1 hour. The mixture was concentrated and the obtained residue was purified by silica gel column chromatography (ethyl acetate-methanol) to obtain Compound II-58 (166 mg, 57%).

LC/MS (ESI): m/z=707.90 [M+H]$^+$, RT=1.93 min, method (2)

The following example compounds were synthesized from commercially available compounds according to the above examples.

TABLE 10

| No. | Structure | NMR or LC/MS |
|---|---|---|
| II-1 | 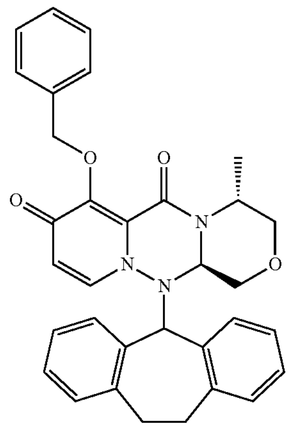 [SMILES: C[C@@H]1COC[C@@H]2N1C(=O)c1c(OCc3ccccc3)c(=O)ccn1N2C1c2ccccc2CCc2ccccc21] | LC/MS (ESI): m/z = 534.2 [M + H]+, RT = 2.22 min, method (1) |
| II-2 | 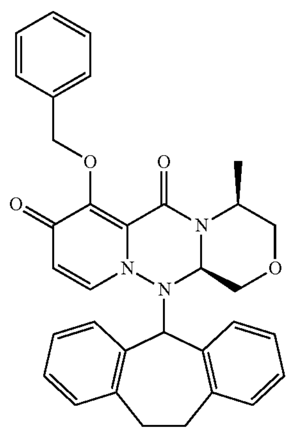 [SMILES: C[C@H]1COC[C@@H]2N1C(=O)c1c(OCc3ccccc3)c(=O)ccn1N2C1c2ccccc2CCc2ccccc21] | LC/MS (ESI): m/z = 534.2 [M + H]+, RT = 2.24 min, method (2) |
| II-3 | 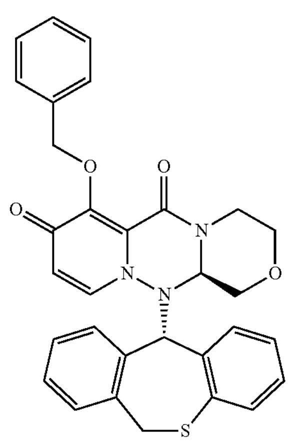 [SMILES: O=C1c2c(OCc3ccccc3)c(=O)ccn2N([C@H]2c3ccccc3CSc3ccccc32)[C@@H]2COCCN12] | 1H-NMR (CDCl3) δ: 2.86 (dd, J = 11.4, 11.4 Hz, 1H), 3.26-3.40 (m, 2H), 3.55 (d, J = 13.4 Hz, 1H), 3.70 (d, J = 10.4 Hz, 1H), 3.86 (d, J = 10.4 Hz, 1H), 4.48 (d, J = 9.5 Hz, 1H), 4.66 (d, J = 13.4 Hz, 1H), 5.20 (s, 1H), 5.43-5.50 (m, 2H), 5.63 (d, J = 10.9 Hz, 1H), 5.79 (d, J = 7.8 Hz, 1H), 6.40 (d, J = 7.7 Hz, 1H), 6.62-6.69 (m, 1H), 7.02-7.07 (m, 3H), 7.18 (d, J = 7.4 Hz, 1H), 7.27-7.44 (m, 6H), 7.60-7.66 (m, 2H). |

TABLE 10-continued
| No. | Structure | NMR or LC/MS |
|---|---|---|
| II-5 | 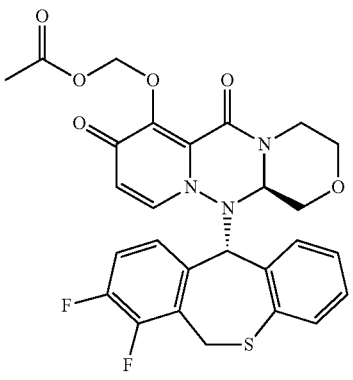 [SMILES: CC(=O)OCOc1c2n(ccc1=O)N([C@@H]1c3ccccc3SCc3c1ccc(F)c3F)[C@@H]1COCCN1C2=O] | 1H-NMR(DMSO-d6)δ: 2.04(s, 3H), 2.90-3.00(m, 1H), 3.44-3.50(m, 2H), 3.64-3.72(m, 1H), 3.95-4.00(m, 1H), 4.11-4.10(m, 1H), 4.20-4.30(m, 2H), 5.40-5.5.46(m, 1H), 6.62-5.75(m, 4H), 6.80-6.90(m, 1H), 6.98-7.10(m, 1H), 7.11-7.20(m, 2H), 7.21-7.30(m, 1H), 7.45-7.50(m, 2H) |
| II-7 | 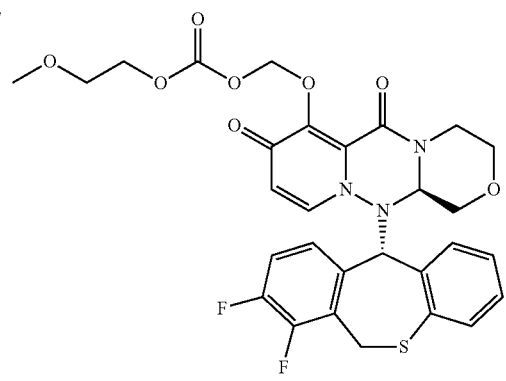 | 1H-NMR(CDCl3)δ: 2.85-2.97 (m, 1H), 3.38 (s, 3H), 3.39-3.48 (m, 1H), 3.54 (t, J = 10.4 Hz, 1H), 3.68 (t, J = 4.4 Hz, 2H), 3.74 (dd, J = 2.8 Hz, 12.0 Hz, 1H), 3.92 (dd, J = 2.8 Hz, 10.8 Hz, 1H), 4.05 (d, J = 13.6 Hz, 1H), 4.36 (q, J = 4.4 Hz, 2H), 4.51 (dd, J = 2.8 Hz, 9.6 Hz, 1H), 4.65 (d, J = 12.0 Hz, 1H), 5.27 (dd, J = 2.0 Hz, 13.6 Hz, 1H), 5.34 (s, 1H), 5.86 (d, J = 8.0 Hz, 1H), 5.93 (s, 2H), 6.81-6.89 (m, 2H), 6.98-7.15 (m, 5H). |
TABLE 11
| No. | Structure | NMR or LC/MS |
|---|---|---|
| II-8 | 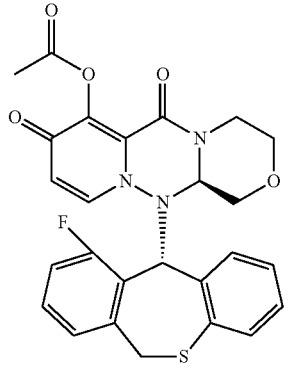 [SMILES: CC(=O)Oc1c2n(ccc1=O)N([C@@H]1c3ccccc3SCc3cccc(F)c31)[C@@H]1COCCN1C2=O] | LC/MS (ESI): m/z = 508 [M + H]+, RT = 1.76 min, method (2) |

TABLE 11-continued

| No. | Structure | NMR or LC/MS |
|---|---|---|
| II-9 | 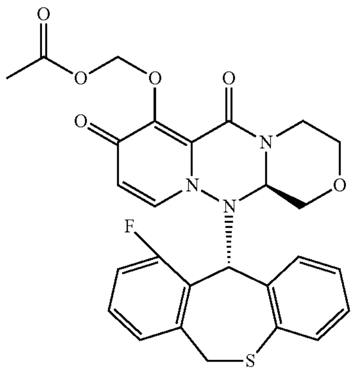 [SMILES: CC(=O)OCOc1c2n(ccc1=O)N([C@@H]1c3ccccc3SCc3cccc(F)c31)[C@@H]1COCCN1C2=O] | 1H-NMR(CDCl3)δ: 2.05(s, 3H), 2.92-3.02(m, 1H), 3.40-3.48(m, 1H), 3.51-3.62(m, 2H), 3.72-3.80(m, 1H), 3.88-3.92(m, 1H), 4.50-4.56(m, 1H), 4.64-4.72(m, 1H), 5.55(d, J = 13.6 Hz, 1H), 5.78-5.82(m, 1H), 5.84-5.88(m, 1H), 5.90-5.98(m, 2H), 6.82-7.00(m, 2H), 7.00-7.20(m, 5H), 7.35-7.42(m, 1H) |
| II-10 | 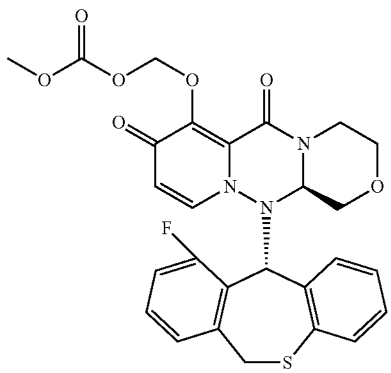 [SMILES: COC(=O)OCOc1c2n(ccc1=O)N([C@@H]1c3ccccc3SCc3cccc(F)c31)[C@@H]1COCCN1C2=O] | LC/MS (ESI): m/z = 554 [M + H]+, RT = 1.76 min, method (1) |
| II-11 | 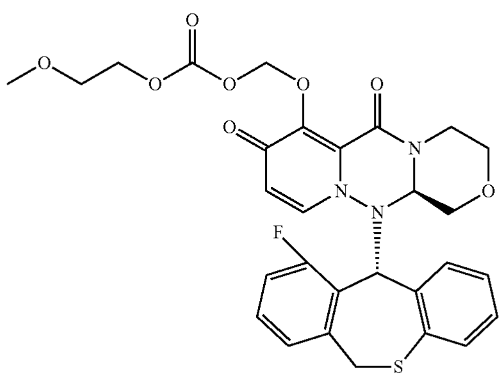 [SMILES: COCCOC(=O)OCOc1c2n(ccc1=O)N([C@@H]1c3ccccc3SCc3cccc(F)c31)[C@@H]1COCCN1C2=O] | LC/MS (ESI): m/z = 598 [M + H]+, RT = 1.80 min, method (2) |
| II-12 | 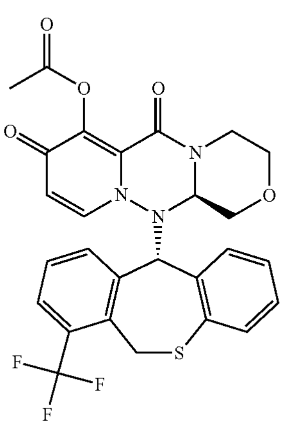 [SMILES: CC(=O)Oc1c2n(ccc1=O)N([C@@H]1c3ccccc3SCc3c1cccc3C(F)(F)F)[C@@H]1COCCN1C2=O] | LC/MS (ESI): m/z = 558 [M + H]+, RT = 1.97 min, method (2) |

TABLE 12
| No. | Structure | NMR or LC/MS |
|---|---|---|
| II-13 | 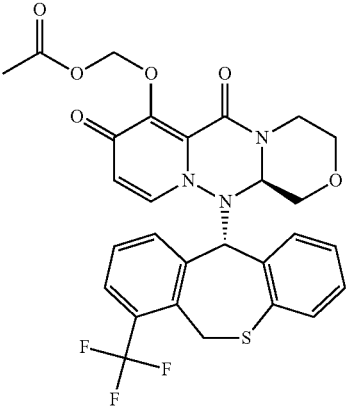 [SMILES: CC(=O)OCOc1c2n(ccc1=O)N([C@@H]1c3ccccc3SCc3c1cccc3C(F)(F)F)[C@@H]1COCCN1C2=O] | LC/MS (ESI): m/z = 588 [M + H]+, RT = 2.00 min, method (2) |
| II-14 | 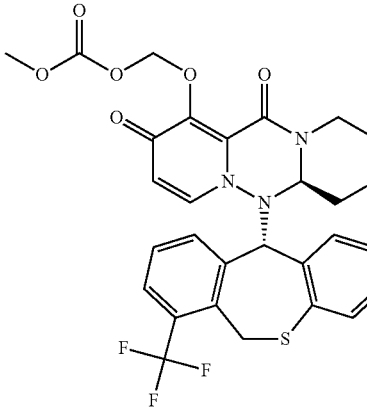 | LC/MS (ESI): m/z = 604 [M + H]+, RT = 2.02 min, method (2) |
| II-15 | 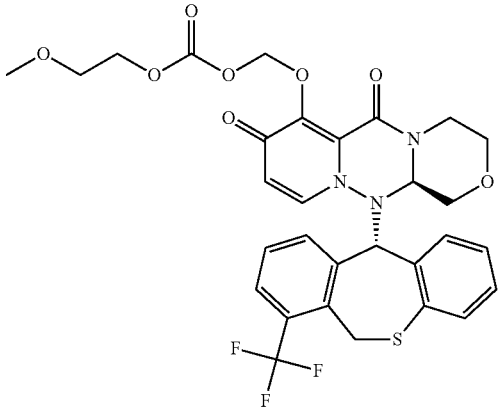 [SMILES: COCCOC(=O)OCOc1c2n(ccc1=O)N([C@@H]1c3ccccc3SCc3c1cccc3C(F)(F)F)[C@@H]1COCCN1C2=O] | LC/MS (ESI): m/z = 648 [M + H]+, RT = 2.06 min, method (2) |
| II-16 | 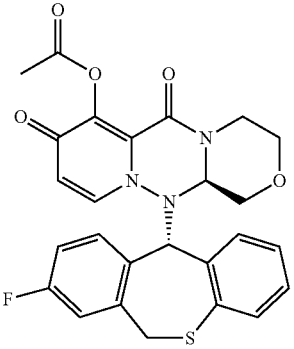 [SMILES: CC(=O)Oc1c2n(ccc1=O)N([C@H]1c3ccc(F)cc3CSc3ccccc31)[C@@H]1COCCN1C2=O] | LC/MS (ESI): m/z = 508 [M + H]+, RT = 1.76 min, method (2) |

TABLE 12-continued

| No. | Structure | NMR or LC/MS |
| --- | --- | --- |
| II-17 | 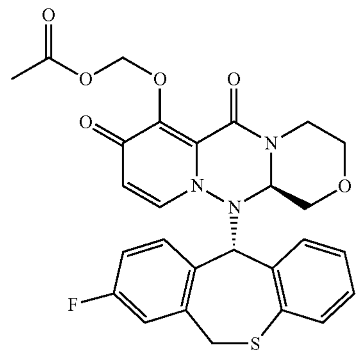 [SMILES: CC(=O)OCOc1c2n(ccc1=O)N([C@H]1c3ccc(F)cc3CSc3ccccc31)[C@@H]1COCCN1C2=O] | LC/MS (ESI): m/z = 538 [M + H]+, RT = 1.78 min, method (2) |

TABLE 13

| No. | Structure | NMR or LC/MS |
| --- | --- | --- |
| II-18 | 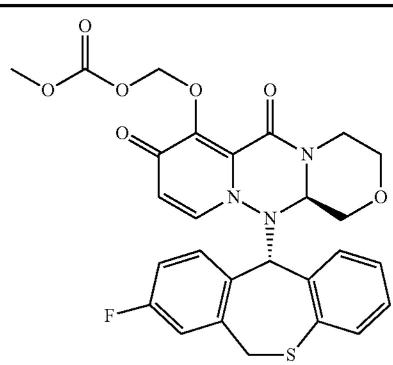 | LC/MS (ESI): m/z = 554 [M + H]+, RT = 1.81 min, method (2) |
| II-19 | 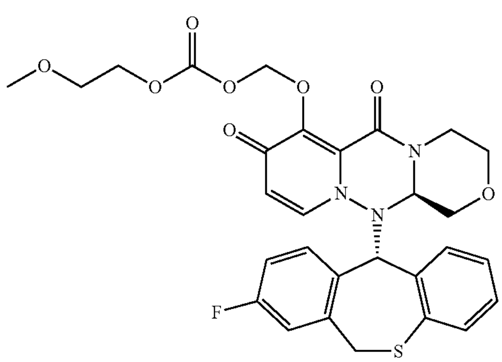 [SMILES: COCCOC(=O)OCOc1c2n(ccc1=O)N([C@H]1c3ccc(F)cc3CSc3ccccc31)[C@@H]1COCCN1C2=O] | LC/MS (ESI): m/z = 598 [M + H]+, RT = 1.85 min, method (2) |
| II-20 | 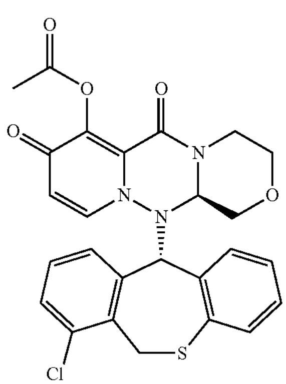 [SMILES: CC(=O)Oc1c2n(ccc1=O)N([C@@H]1c3ccccc3SCc3c(Cl)cccc31)[C@@H]1COCCN1C2=O] | LC/MS (ESI): m/z = 524 [M + H]+, RT = 1.91 min, method (2) |

TABLE 13-continued

| No. | Structure | NMR or LC/MS |
|---|---|---|
| II-21 | 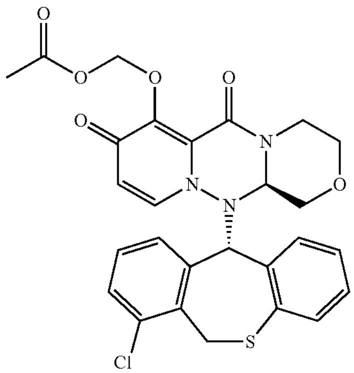 [SMILES: CC(=O)OCOc1c2n(ccc1=O)N([C@@H]1c3ccccc3SCc3c(Cl)cccc31)[C@@H]1COCCN1C2=O] | LC/MS (ESI): m/z = 554 [M + H]+, RT = 1.94 min, method (2) |
| II-22 | 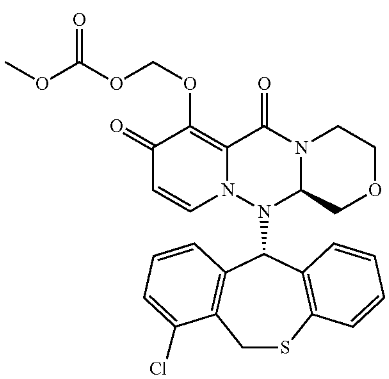 [SMILES: COC(=O)OCOc1c2n(ccc1=O)N([C@@H]1c3ccccc3SCc3c(Cl)cccc31)[C@@H]1COCCN1C2=O] | LC/MS (ESI): m/z = 570 [M + H]+, RT = 1.97 min, method (2) |
| II-23 | 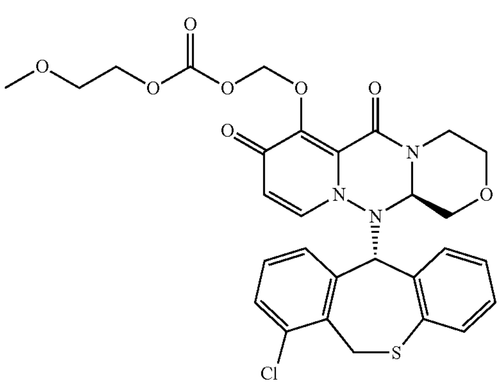 [SMILES: COCCOC(=O)OCOc1c2n(ccc1=O)N([C@@H]1c3ccccc3SCc3c(Cl)cccc31)[C@@H]1COCCN1C2=O] | LC/MS (ESI): m/z = 614 [M + H]+, RT = 2.00 min, method (2) |

TABLE 14
| No. | Structure | NMR or LC/MS |
|---|---|---|
| II-24 | 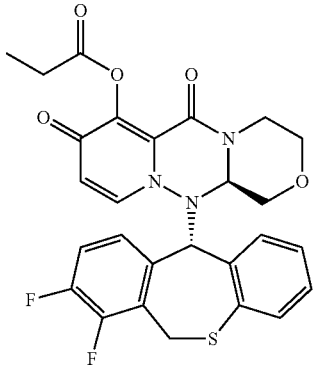 [SMILES: CCC(=O)Oc1c2n(ccc1=O)N([C@@H]1c3ccccc3SCc3c1ccc(F)c3F)[C@@H]1COCCN1C2=O] | 1H-NMR (CDCl3) δ: 1.33 (3H, t, J = 7.0 Hz), 2.82 (2H, d, J = 6.1 Hz), 2.93 (1H, t, J = 11.2 Hz), 3.42 (1H, t, J = 11.4 Hz), 3.59 (1H, t, J = 10.2 Hz), 3.78 (1H, d, J = 11.2 Hz), 3.96 (1H, d, J = 10.3 Hz), 4.06 (1H, d, J = 13.8 Hz), 4.55 (1H, d, J = 8.9 Hz), 4.63 (1H, d, J = 13.6 Hz), 5.29 (1H, d, J = 13.9 Hz), 5.36 (1H, s), 5.88 (1H, d, J = 7.4 Hz), 6.90 (1H, s), 7.03-7.12 (6H, m). |
| II-25 | 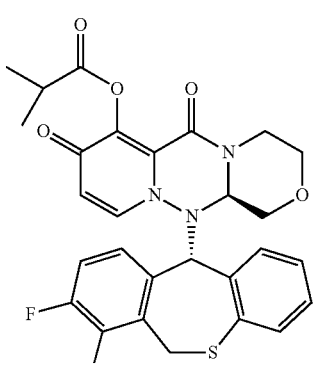 | 1H-NMR (CDCl3) δ: 1.42 (d, J = 6.8 Hz, 6H), 2.85-3.05 (m, 2H), 3.40-3.49 (m, 1H), 3.59 (t, J = 10.4 Hz, 1H), 3.76 (d, J = 11.4 Hz, 1H), 3.94 (d, J = 10.4 Hz, 1H), 4.06 (d, J = 14.1 Hz, 1H), 4.51-4.57 (m, 1H), 4.59-4.70 (m, 1H), 5.25-5.32 (m, 1H), 5.35-5.39 (m, 1H), 5.80-5.89 (m, 1H), 6.85-7.15 (m, 7H). |
| II-26 | 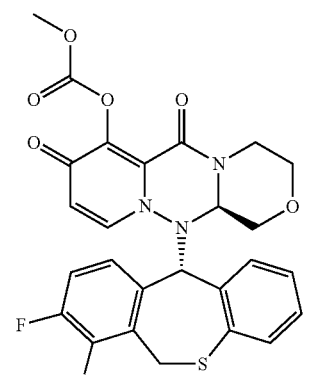 | LC/MS (ESI): m/z = 542 [M + H]+, RT = 1.92 min, method (1) |

TABLE 14-continued

| No. | Structure | NMR or LC/MS |
|---|---|---|
| II-28 | 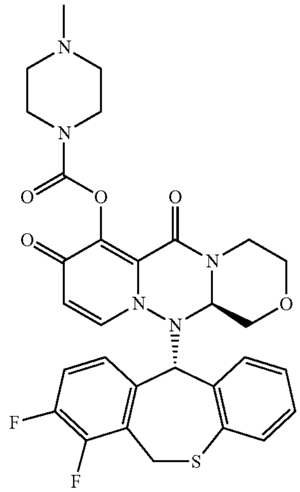 [SMILES: CN1CCN(C(=O)Oc2c3n(ccc2=O)N([C@@H]2c4ccccc4SCc4c2ccc(F)c4F)[C@@H]2COCCN2C3=O)CC1] | LC/MS (ESI): m/z = 610 [M + H]+, RT = 1.57 min, method (1) |
| II-29 | 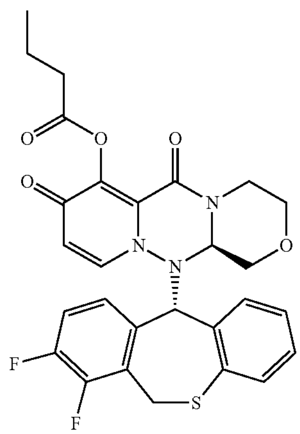 [SMILES: CCCC(=O)Oc1c2n(ccc1=O)N([C@@H]1c3ccccc3SCc3c1ccc(F)c3F)[C@@H]1COCCN1C2=O] | LC/MS (ESI): m/z = 554 [M + H]+, RT = 2.10 min, method (1) |

TABLE 15

| No. | Structure | NMR or LC/MS |
|---|---|---|
| II-30 | 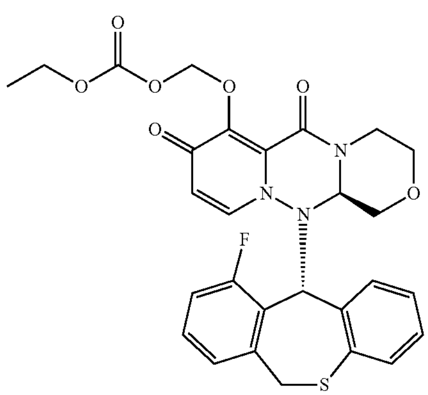 [SMILES: CCOC(=O)OCOc1c2n(ccc1=O)N([C@@H]1c3ccccc3SCc3cccc(F)c31)[C@@H]1COCCN1C2=O] | LC/MS (ESI): m/z = 568 [M + H]+, RT = 1.91 min, method (1) |

TABLE 15-continued

| No. | Structure | NMR or LC/MS |
|---|---|---|
| II-31 | 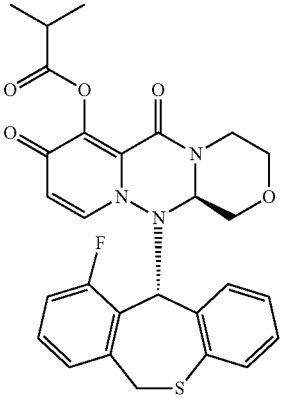 [SMILES: CC(C)C(=O)Oc1c2n(ccc1=O)N([C@@H]1c3ccccc3SCc3cccc(F)c31)[C@@H]1COCCN1C2=O] | 1H-NMR (CDCl3) δ: 1.42 (d, J = 6.8 Hz, 6H), 2.90-3.07 (m, 2H), 3.44 (t, J = 10.8 Hz, 1H), 3.60 (d, J = 12.8 Hz, 2H), 3.77 (d, J = 10.8 Hz, 1H), 3.93 (dd, J = 10.8, 2.8 Hz, 1H), 4.56 (dd, J = 9.6, 2.8 Hz, 1H), 4.67 (m, 1H), 5.59 (m, 1H), 5.87 (m, 1H), 5.59 (s, 1H), 6.91-7.21 (m, 7H), 7.38 (m, 1H). |
| II-32 | 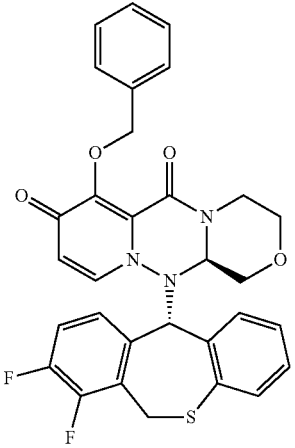 [SMILES: O=C1c2c(OCc3ccccc3)c(=O)ccn2N([C@@H]2c3ccccc3SCc3c2ccc(F)c3F)[C@@H]2COCCN12] | 1H-NMR (CDCl3) δ: 2.88 (1H, t, J = 11.2 Hz), 3.28-3.39 (2H, m), 3.72 (1H, d, J = 12.6 Hz), 3.86 (1H, d, J = 9.6 Hz), 4.03 (1H, d, J = 13.9 Hz), 4.45 (1H, d, J = 8.6 Hz), 4.67 (1H, d, J = 13.1 Hz), 5.19-5.26 (2H, m), 5.45 (1H, d, J = 10.9 Hz), 5.63 (1H, d, J = 10.9 Hz), 5.77 (1H, d, J = 7.6 Hz), 6.40 (1H, d, J = 7.8 Hz), 6.68 (1H, t, J = 6.9 Hz), 6.94-7.01 (2H, m), 7.03-7.12 (3H, m), 7.29-7.38 (3H, m), 7.61 (2H, d, J = 7.1 Hz). |
| II-33 | 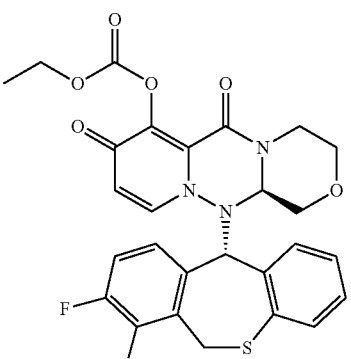 | 1H-NMR (CDCl3) δ: 1.46 (t, J = 7.2 Hz, 3H), 2.95 (m, 1H), 3.42 (td, J = 12.0, 2.4 Hz, 1H), 3.58 (t, J = 10.4 Hz, 1H), 3.78 (dd, J = 12.0, 2.8 Hz, 1H), 3.95 (dd, J = 11.2, 2.8 Hz, 1H), 4.07 (d, J = 13.6 Hz, 1H), 4.41 (m, 2H), 4.56 (dd, J = 10.0, 2.8 Hz, 1H), 4.67 (dd, J = 10.0, 2.4 Hz, 1H), 5.29 (dd, J = 13.6, 2.0 Hz, 1H), 5.36 (s, 1H), 5.91 (d, J = 8.0 Hz, 1H), 6.88-7.15 (m, 7H). |
| II-34 | 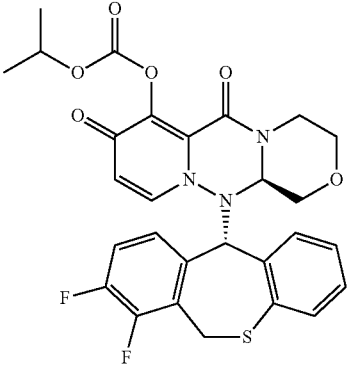 [SMILES: CC(C)OC(=O)Oc1c2n(ccc1=O)N([C@@H]1c3ccccc3SCc3c1ccc(F)c3F)[C@@H]1COCCN1C2=O] | 1H-NMR (CDCl3) δ: 1.46 (m, 6H), 2.95 (m, 1H), 3.41 (td, J = 12.0, 2.0 Hz, 1H), 3.58 (t, J = 10.8 Hz, 1H), 3.77 (dd, J = 12.0, 3.2 Hz, 1H), 3.95 (dd, J = 10.8, 2.4 Hz, 1H), 4.06 (d, J = 14.0 Hz, 1H), 4.55 (dd, J = 9.6, 2.8 Hz, 1H), 4.67 (d, J = 13.6 Hz, 1H), 5.04 (m, 1H), 5.29 (d, J = 13.6 Hz, 1H), 5.36 (s, 1H), 5.90 (d, J = 8.0 Hz, 1H), 6.90-7.13 (m, 7H). |

TABLE 16

| No. | Structure | NMR or LC/MS |
|---|---|---|
| II-35 | 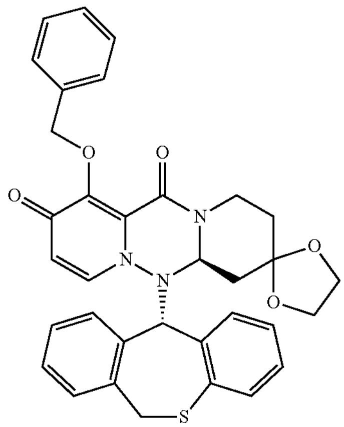 [SMILES: O=C1c2c(OCc3ccccc3)c(=O)ccn2N([C@H]2c3ccccc3CSc3ccccc32)[C@@H]2CC3(CCN12)OCCO3] | LC/MS (ESI): m/z = 594 [M + H]+, RT = 2.13 min, method (1) |
| II-36 | 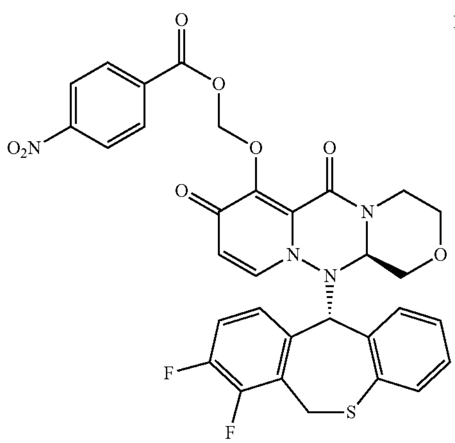 [SMILES: O=C(OCOc1c2n(ccc1=O)N([C@@H]1c3ccccc3SCc3c1ccc(F)c3F)[C@@H]1COCCN1C2=O)c1ccc([N+](=O)[O-])cc1] | LC/MS (ESI): m/z = 663 [M + H]+, RT = 2.29 min, method (1) |
| II-37 | 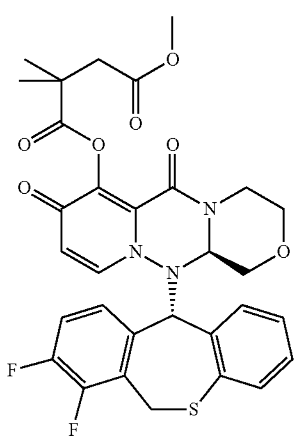 [SMILES: COC(=O)CC(C)(C)C(=O)Oc1c2n(ccc1=O)N([C@@H]1c3ccccc3SCc3c1ccc(F)c3F)[C@@H]1COCCN1C2=O] | LC/MS (ESI): m/z = 626 [M + H]+, RT = 2.18 min, method (1) |

TABLE 16-continued

| No. | Structure | NMR or LC/MS |
|---|---|---|
| II-38 | 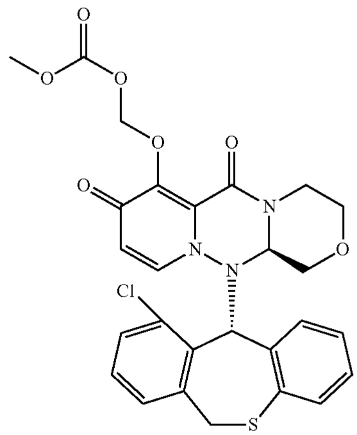 [SMILES: COC(=O)OCOc1c2n(ccc1=O)N([C@@H]1c3ccccc3SCc3cccc(Cl)c31)[C@@H]1COCCN1C2=O] | LC/MS (ESI): m/z = 570 [M + H]+, RT = 1.85 min, method (2) |
| II-39 | 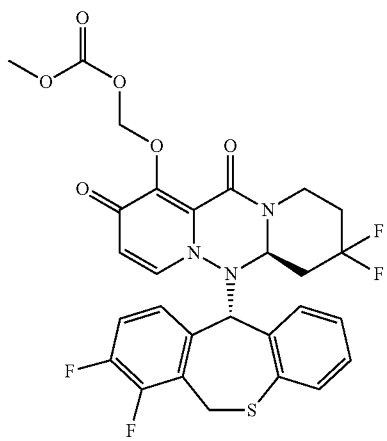 [SMILES: COC(=O)OCOc1c2n(ccc1=O)N([C@@H]1c3ccccc3SCc3c1ccc(F)c3F)[C@@H]1CC(F)(F)CCN1C2=O] | LC/MS (ESI): m/z = 606 [M + H]+, RT = 2.12 min, method (2) |

TABLE 17

| No. | Structure | NMR or LC/MS |
|---|---|---|
| II-40 | 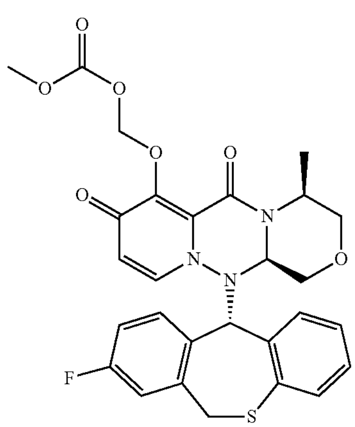 [SMILES: COC(=O)OCOc1c2n(ccc1=O)N([C@H]1c3ccc(F)cc3CSc3ccccc31)[C@@H]1COC[C@H](C)N1C2=O] | LC/MS (ESI): m/z = 568 [M + H]+, RT = 1.92 min, method (2) |

TABLE 17-continued

| No. | Structure | NMR or LC/MS |
|---|---|---|
| II-41 | 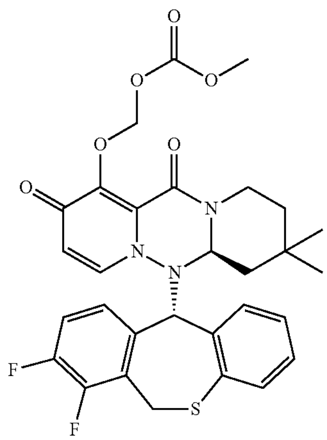 [SMILES: COC(=O)OCOc1c2n(ccc1=O)N([C@@H]1c3ccccc3SCc3c1ccc(F)c3F)[C@@H]1CC(C)(C)CCN1C2=O] | LC/MS (ESI): m/z = 598 [M + H]+, RT = 2.27 min, method (2) |
| II-42 | 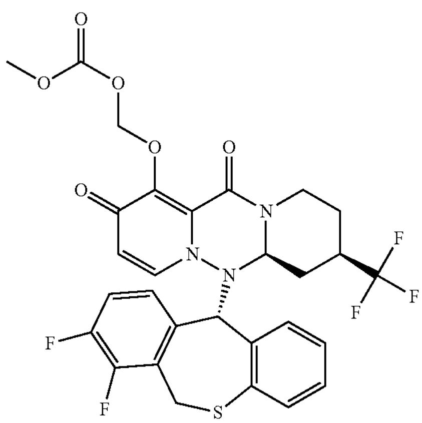 [SMILES: COC(=O)OCOc1c2n(ccc1=O)N([C@@H]1c3ccccc3SCc3c1ccc(F)c3F)[C@@H]1C[C@H](C(F)(F)F)CCN1C2=O] | LC/MS (ESI): m/z = 638 [M + H]+, RT = 2.17 min, method (2) |
| II-43 | 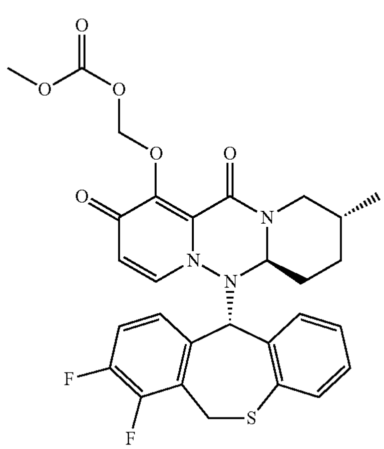 | LC/MS (ESI): m/z = 584 [M + H]+, RT = 2.18 min, method (2) |

TABLE 17-continued

| No. | Structure | NMR or LC/MS |
|---|---|---|
| II-44 | 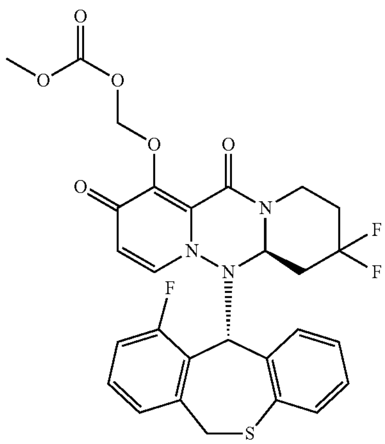 [SMILES: COC(=O)OCOc1c2n(ccc1=O)N([C@@H]1c3ccccc3SCc3cccc(F)c31)[C@@H]1CC(F)(F)CCN1C2=O] | LC/MS (ESI): m/z = 588 [M + H]+, RT = 2.00 min, method (2) |

TABLE 18

| No. | Structure | NMR or LC/MS |
|---|---|---|
| II-45 | 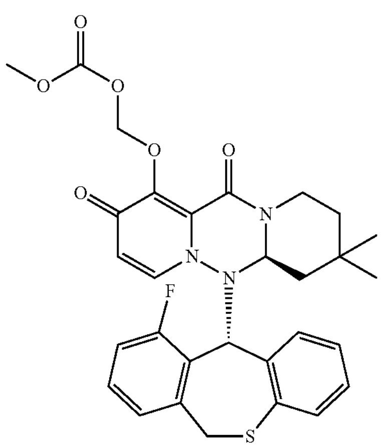 | LC/MS (ESI): m/z = 580 [M + H]+, RT = 2.14 min, method (2) |
| II-46 | 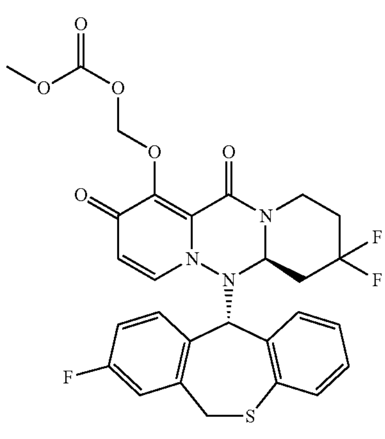 [SMILES: COC(=O)OCOc1c2n(ccc1=O)N([C@H]1c3ccc(F)cc3CSc3ccccc31)[C@@H]1CC(F)(F)CCN1C2=O] | LC/MS (ESI): m/z = 588 [M + H]+, RT = 2.04 min, method (2) |

TABLE 18-continued

| No. | Structure | NMR or LC/MS |
|---|---|---|
| II-47 | 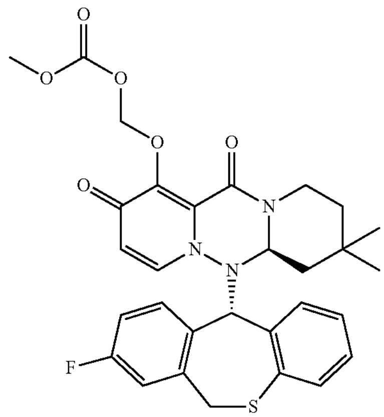 | LC/MS (ESI): m/z = 580 [M + H]+, RT = 2.17 min, method (2) |
| II-48 | 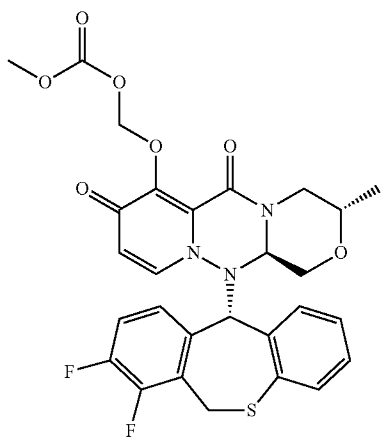 | LC/MS (ESI): m/z = 586 [M + H]+, RT = 2.03 min, method (2) |
| II-49 | 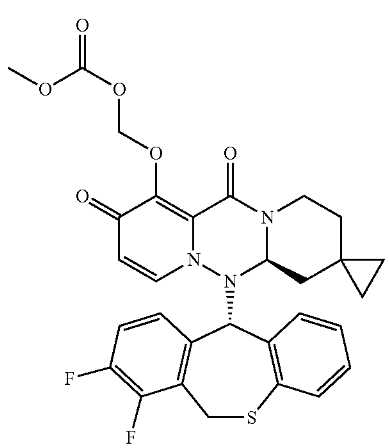 [SMILES: COC(=O)OCOc1c2n(ccc1=O)N([C@@H]1c3ccccc3SCc3c1ccc(F)c3F)[C@@H]1CC3(CCN1C2=O)CC3] | LC/MS (ESI): m/z = 596 [M + H]+, RT = 2.18 min, method (2) |

TABLE 19

| No. | Structure | NMR or LC/MS |
|---|---|---|
| II-50 | 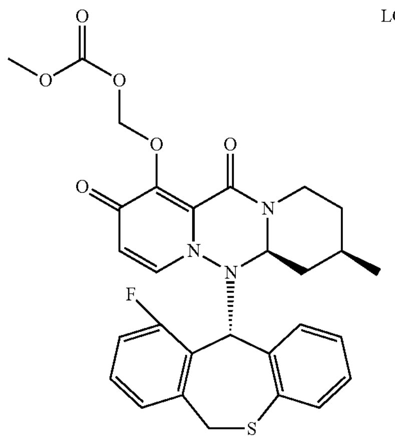 | LC/MS (ESI): m/z = 566 [M + H]+, RT = 2.02 min, method (2) |
| II-51 | 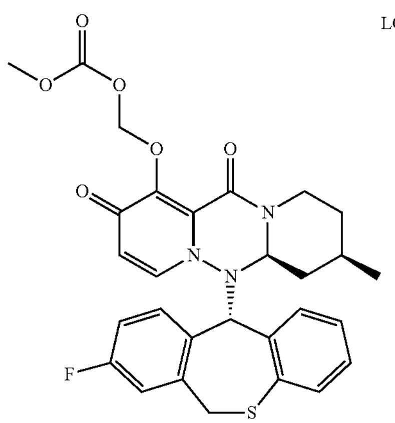 | LC/MS (ESI): m/z = 566 [M + H]+, RT = 2.08 min, method (2) |
| II-52 | 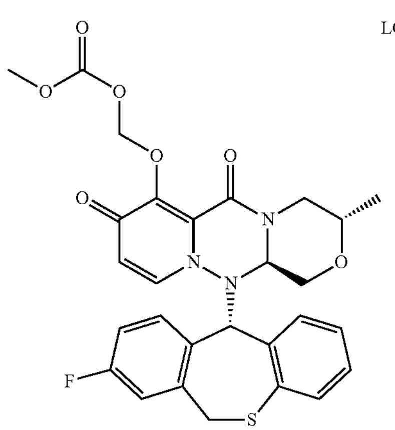 | LC/MS (ESI): m/z = 568 [M + H]+, RT = 1.93 min, method (2) |

TABLE 19-continued

| No. | Structure | NMR or LC/MS |
|---|---|---|
| II-53 | 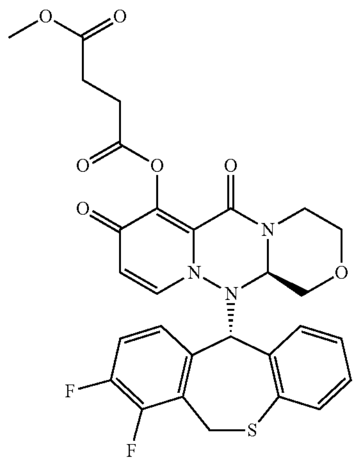 [SMILES: COC(=O)CCC(=O)Oc1c2n(ccc1=O)N([C@@H]1c3ccccc3SCc3c1ccc(F)c3F)[C@@H]1COCCN1C2=O] | LC/MS (ESI): m/z = 598.1 [M + H]+, RT = 1.96 min, method (2) |
| II-54 | 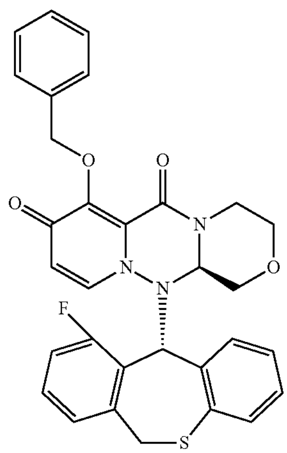 [SMILES: O=C1c2c(OCc3ccccc3)c(=O)ccn2N([C@@H]2c3ccccc3SCc3cccc(F)c32)[C@@H]2COCCN12] | 1H-NMR (CDCl3) δ: 2.89-2.98 (m, 1H), 3.30-3.43 (m, 2H), 3.57 (d, J = 13.4 Hz, 1H), 3.73 (dd, J = 11.6, 2.8 Hz, 1H), 3.87 (dd, J = 10.7, 2.4 Hz, 1H), 4.49 (dd, J = 9.9, 2.5 Hz, 1H), 4.72 (d, J = 12.9 Hz, 1H), 5.43 (d, J = 10.8 Hz, 1H), 5.51 (d, J = 13.4 Hz, 1H), 5.64 (d, J = 10.9 Hz, 1H), 5.78 (d, J = 7.7 Hz, 1H), 5.84 (s, 1H), 6.44 (d, J = 7.8 Hz, 1H), 6.67 (t, J = 7.0 Hz, 1H), 7.02-7.13 (m, 5H), 7.29-7.40 (m, 4H), 7.64 (d, J = 7.7 Hz, 2H). |

40

TABLE 20

| No. | Structure | NMR or LC/MS |
|---|---|---|
| II-56 | 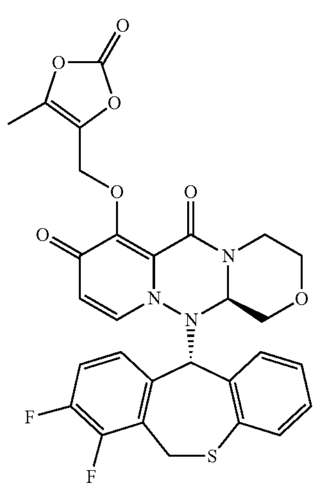 [SMILES: Cc1oc(=O)oc1COc1c2n(ccc1=O)N([C@@H]1c3ccccc3SCc3c1ccc(F)c3F)[C@@H]1COCCN1C2=O] | LC/MS (ESI): m/z = 595.90 [M + H]+, RT = 1.93 min, method (2) |

TABLE 20-continued

| No. | Structure | NMR or LC/MS |
| --- | --- | --- |
| II-59 | 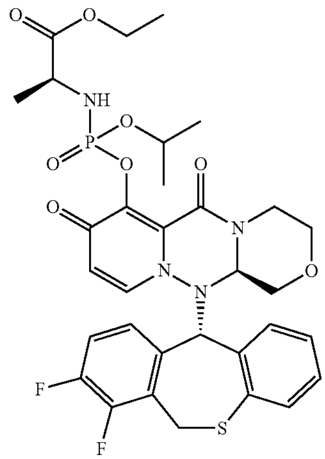 [SMILES: CCOC(=O)[C@H](C)NP(=O)(Oc1c2n(ccc1=O)N([C@@H]1c3ccccc3SCc3c1ccc(F)c3F)[C@@H]1COCCN1C2=O)OC(C)C] | LC/MS (ESI): m/z = 705.05 [M + H]+, RT = 2.16 min, method (2) |
| II-60 | 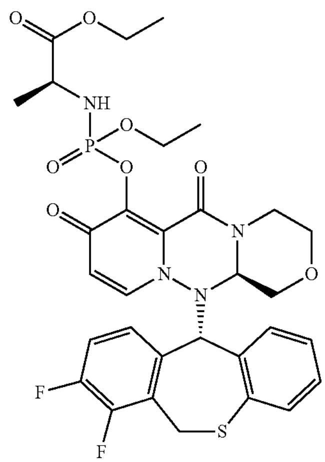 [SMILES: CCOC(=O)[C@H](C)NP(=O)(OCC)Oc1c2n(ccc1=O)N([C@@H]1c3ccccc3SCc3c1ccc(F)c3F)[C@@H]1COCCN1C2=O] | LC/MS (ESI): m/z = 691.00 [M + H]+, RT = 2.08 min, method (2) |
| II-62 | 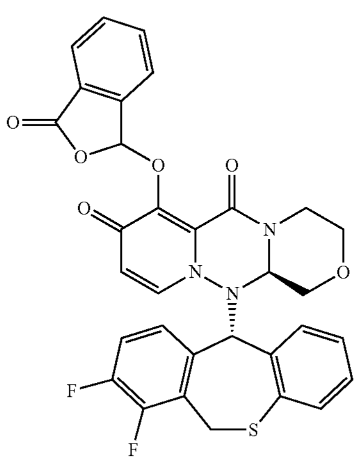 [SMILES: O=C1OC(Oc2c3n(ccc2=O)N([C@@H]2c4ccccc4SCc4c2ccc(F)c4F)[C@@H]2COCCN2C3=O)c2ccccc21] | LC/MS (ESI): m/z = 615.95 [M + H]+, RT = 2.07 min, method (2) |

TABLE 21

| No. | Structure | NMR or LC/MS |
| --- | --- | --- |
| II-63 | 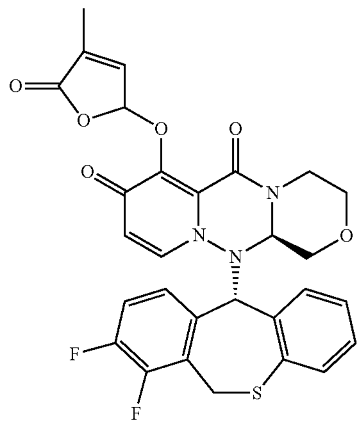 [SMILES: CC1=CC(Oc2c3n(ccc2=O)N([C@@H]2c4ccccc4SCc4c2ccc(F)c4F)[C@@H]2COCCN2C3=O)OC1=O] | LC/MS (ESI): m/z = 579.95 [M + H]+, RT = 1.92 min, method (2) |
| II-64 | 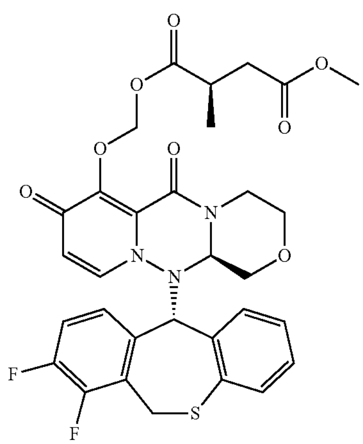 [SMILES: COC(=O)C[C@@H](C)C(=O)OCOc1c2n(ccc1=O)N([C@@H]1c3ccccc3SCc3c1ccc(F)c3F)[C@@H]1COCCN1C2=O] | LC/MS (ESI): m/z = 642.35 [M + H]+, RT = 2.05 min, method (2) |
| II-66 | 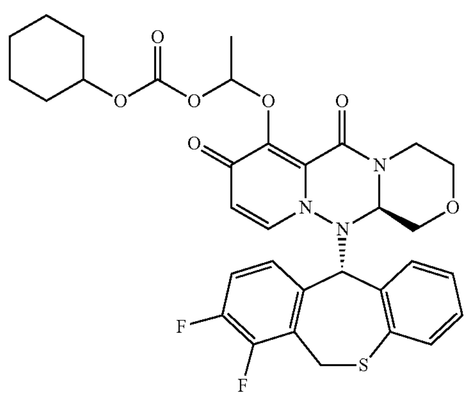 [SMILES: CC(OC(=O)OC1CCCCC1)Oc1c2n(ccc1=O)N([C@@H]1c3ccccc3SCc3c1ccc(F)c3F)[C@@H]1COCCN1C2=O] | LC/MS (ESI): m/z = 654.05 [M + H]+, RT = 2.43, 2.51 min, method (2) |

TABLE 21-continued

| No. | Structure | NMR or LC/MS |
|---|---|---|
| II-67 | 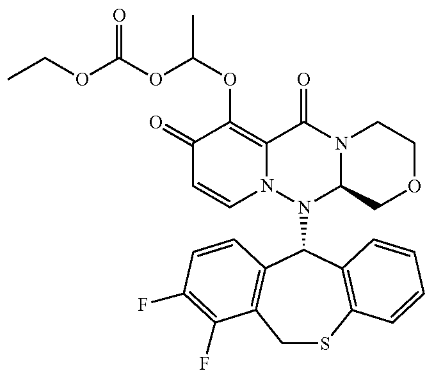 [SMILES: CCOC(=O)OC(C)Oc1c2n(ccc1=O)N([C@@H]1c3ccccc3SCc3c1ccc(F)c3F)[C@@H]1COCCN1C2=O] | LC/MS (ESI): m/z = 600.00 [M + H]+, RT = 2.05, 2.11 min, method (2) |
| II-68 | 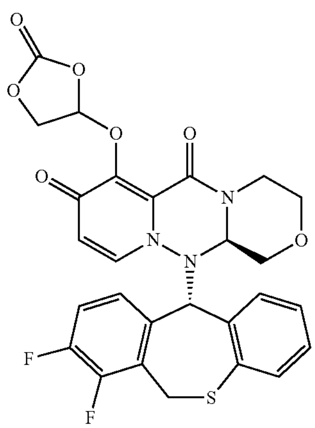 [SMILES: O=C1OCC(Oc2c3n(ccc2=O)N([C@@H]2c4ccccc4SCc4c2ccc(F)c4F)[C@@H]2COCCN2C3=O)O1] | LC/MS (ESI): m/z = 569.95 [M + H]+, RT = 1.84 min, method (2) |

TABLE 22

| No. | Structure | NMR or LC/MS |
|---|---|---|
| II-69 | 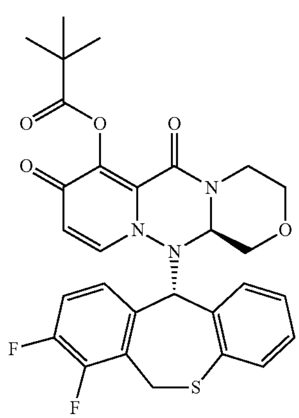 [SMILES: CC(C)(C)C(=O)Oc1c2n(ccc1=O)N([C@@H]1c3ccccc3SCc3c1ccc(F)c3F)[C@@H]1COCCN1C2=O] | LC/MS (ESI): m/z = 568.00 [M + H]+, RT = 2.17 min, method (2) |

TABLE 22-continued

| No. | Structure | NMR or LC/MS |
| --- | --- | --- |
| II-70 | 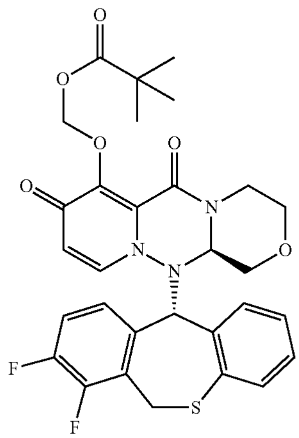 [SMILES: CC(C)(C)C(=O)OCOc1c2n(ccc1=O)N([C@@H]1c3ccccc3SCc3c1ccc(F)c3F)[C@@H]1COCCN1C2=O] | LC/MS (ESI): m/z = 598.00 [M + H]+, RT = 2.23 min, method (2) |
| II-71 | 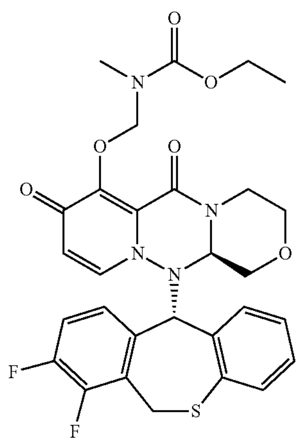 [SMILES: CCOC(=O)N(C)COc1c2n(ccc1=O)N([C@@H]1c3ccccc3SCc3c1ccc(F)c3F)[C@@H]1COCCN1C2=O] | LC/MS (ESI): m/z = 599.05 [M + H]+, RT = 1.99 min, method (2) |
| II-72 | 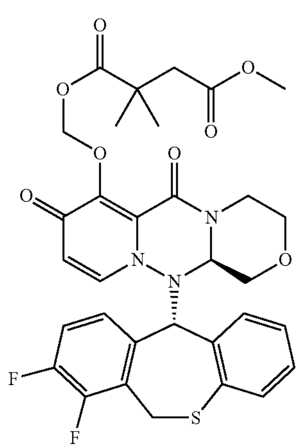 [SMILES: COC(=O)CC(C)(C)C(=O)OCOc1c2n(ccc1=O)N([C@@H]1c3ccccc3SCc3c1ccc(F)c3F)[C@@H]1COCCN1C2=O] | LC/MS (ESI): m/z = 656.00 [M + H]+, RT = 2.13 min, method (2) |

TABLE 22-continued

| No. | Structure | NMR or LC/MS |
|---|---|---|
| II-73 | 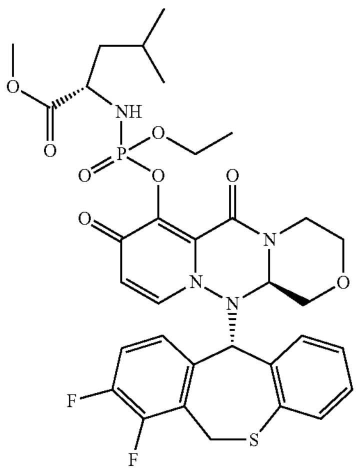 [SMILES: CCOP(=O)(N[C@@H](CC(C)C)C(=O)OC)Oc1c2n(ccc1=O)N([C@@H]1c3ccccc3SCc3c1ccc(F)c3F)[C@@H]1COCCN1C2=O] | LC/MS (ESI): m/z = 719.05 [M + H]+, RT = 2.28 min, method (2) |

TABLE 23

| No. | Structure | NMR or LC/MS |
|---|---|---|
| II-74 | 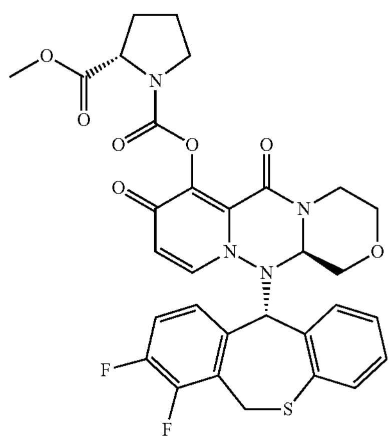 [SMILES: COC(=O)[C@@H]1CCCN1C(=O)Oc1c2n(ccc1=O)N([C@@H]1c3ccccc3SCc3c1ccc(F)c3F)[C@@H]1COCCN1C2=O] | LC/MS (ESI): m/z = 638.95 [M + H]+, RT = 1.89 min, method (2) |
| II-75 | 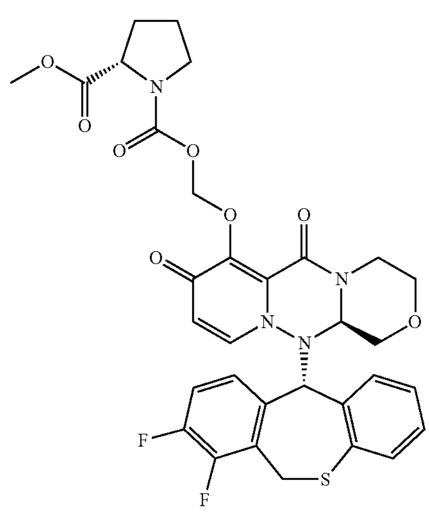 [SMILES: COC(=O)[C@@H]1CCCN1C(=O)OCOc1c2n(ccc1=O)N([C@@H]1c3ccccc3SCc3c1ccc(F)c3F)[C@@H]1COCCN1C2=O] | LC/MS (ESI): m/z = 668.95 [M + H]+, RT = 1.97 min, method (2) |

TABLE 23-continued

| No. | Structure | NMR or LC/MS |
|---|---|---|
| II-76 | 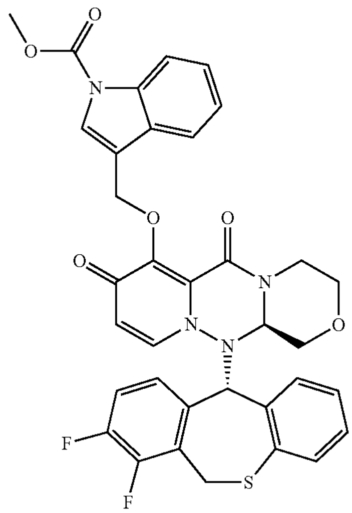 [SMILES: COC(=O)n1cc(COc2c3n(ccc2=O)N([C@@H]2c4ccccc4SCc4c2ccc(F)c4F)[C@@H]2COCCN2C3=O)c2ccccc21] | LC/MS (ESI): m/z = 671.00 [M + H]+, RT = 2.24 min, method (2) |
| II-77 | 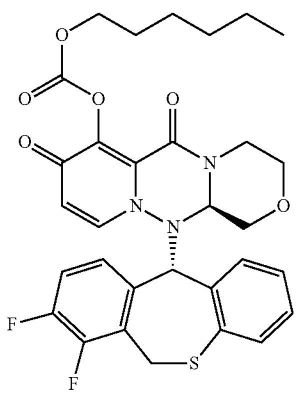 [SMILES: CCCCCCOC(=O)Oc1c2n(ccc1=O)N([C@@H]1c3ccccc3SCc3c1ccc(F)c3F)[C@@H]1COCCN1C2=O] | LC/MS (ESI): m/z = 612.10 [M + H]+, RT = 2.45 min, method (2) |
| II-78 | 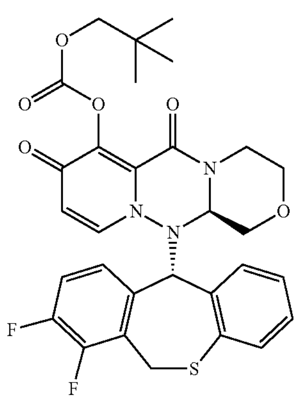 [SMILES: CC(C)(C)COC(=O)Oc1c2n(ccc1=O)N([C@@H]1c3ccccc3SCc3c1ccc(F)c3F)[C@@H]1COCCN1C2=O] | LC/MS (ESI): m/z = 598.00 [M + H]+, RT = 2.29 min, method (2) |

TABLE 24
| No. | Structure | NMR or LC/MS |
|---|---|---|
| II-79 | 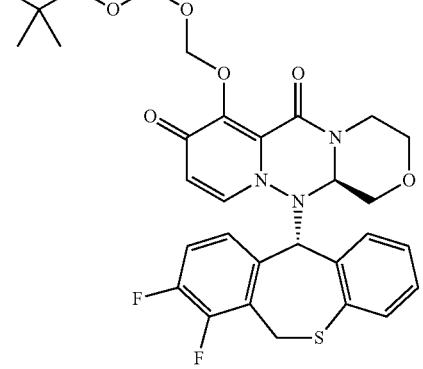 | LC/MS (ESI): m/z = 672 [M + H]+, RT = 2.27 min, method (1) |
| II-80 | 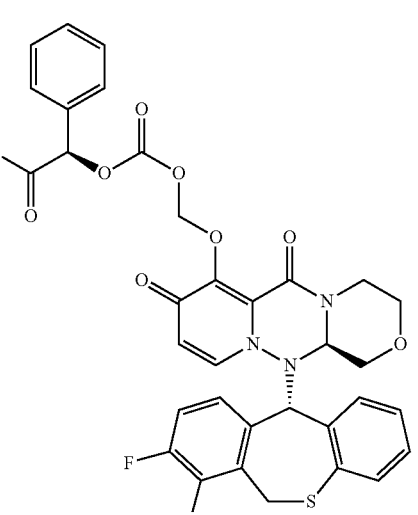 | LC/MS (ESI): m/z = 706 [M + H]+, RT = 2.39 min, method (1) |
| II-81 | 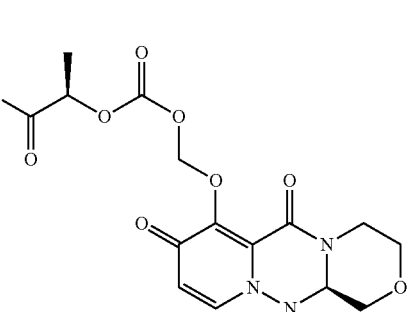 | LC/MS (ESI): m/z = 644 [M + H]+, RT = 2.13 min, method (1) |

TABLE 24-continued
| No. | Structure | NMR or LC/MS |
|---|---|---|
| II-82 | 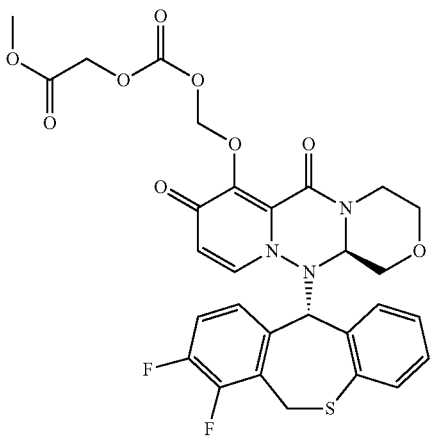 [SMILES: COC(=O)COC(=O)OCOc1c2n(ccc1=O)N([C@@H]1c3ccccc3SCc3c1ccc(F)c3F)[C@@H]1COCCN1C2=O] | LC/MS (ESI): m/z = 630 [M + H]+, RT = 2.03 min, method (1) |
TABLE 25
| No. | Structure | NMR or LC/MS |
|---|---|---|
| II-83 | 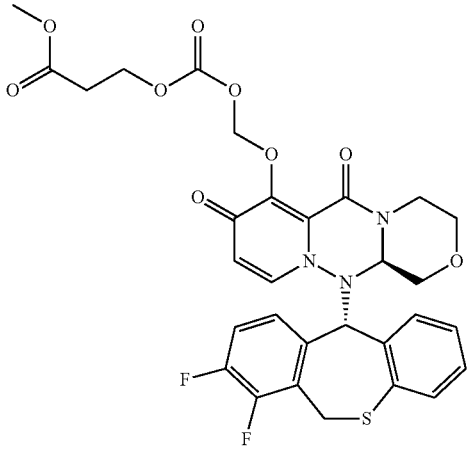 [SMILES: COC(=O)CCOC(=O)OCOc1c2n(ccc1=O)N([C@@H]1c3ccccc3SCc3c1ccc(F)c3F)[C@@H]1COCCN1C2=O] | LC/MS (ESI): m/z = 644 [M + H]+, RT = 2.06 min, method (1) |
| II-84 | 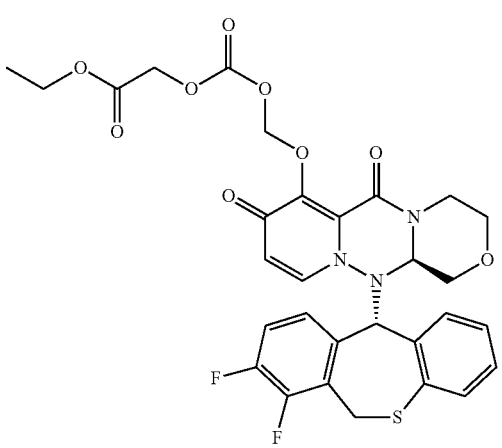 [SMILES: CCOC(=O)COC(=O)OCOc1c2n(ccc1=O)N([C@@H]1c3ccccc3SCc3c1ccc(F)c3F)[C@@H]1COCCN1C2=O] | LC/MS (ESI): m/z = 644 [M + H]+, RT = 2.15 min, method (1) |

TABLE 25-continued
| No. | Structure | NMR or LC/MS |
|---|---|---|
| II-85 | 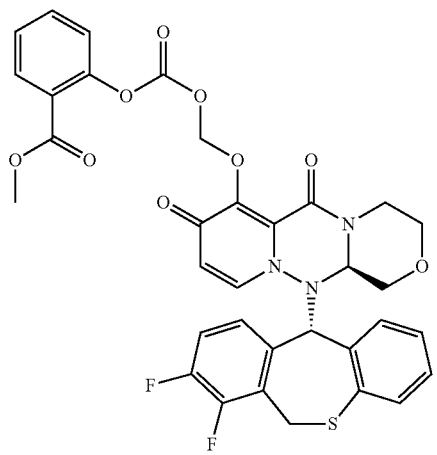 [SMILES: COC(=O)c1ccccc1OC(=O)OCOc1c2n(ccc1=O)N([C@@H]1c3ccccc3SCc3c1ccc(F)c3F)[C@@H]1COCCN1C2=O] | LC/MS (ESI): m/z = 692 [M + H]+, RT = 2.31 min, method (1) |
| II-86 | 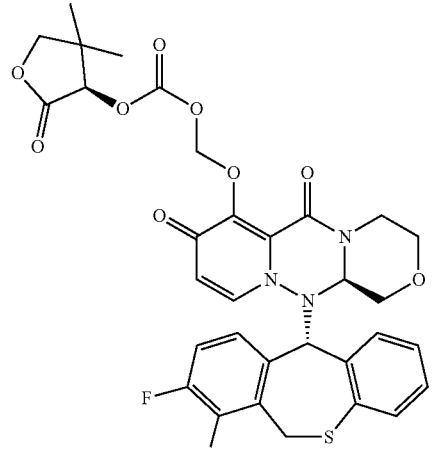 | LC/MS (ESI): m/z = 670 [M + H]+, RT = 2.20 min, method (1) |
TABLE 26
| No. | Structure | NMR or LC/MS |
|---|---|---|
| II-87 | 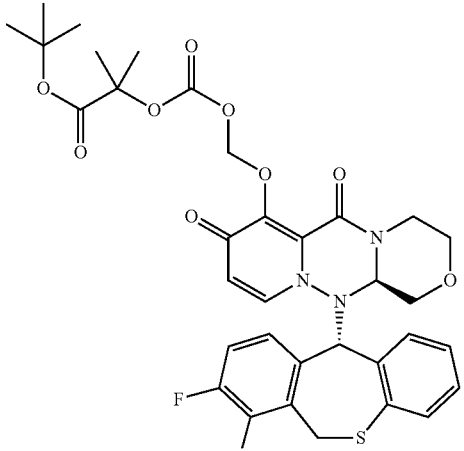 | LC/MS (ESI): m/z = 700 [M + H]+, RT = 2.45 min, method (1) |

| No. | Structure | NMR or LC/MS |
| --- | --- | --- |
| II-88 | 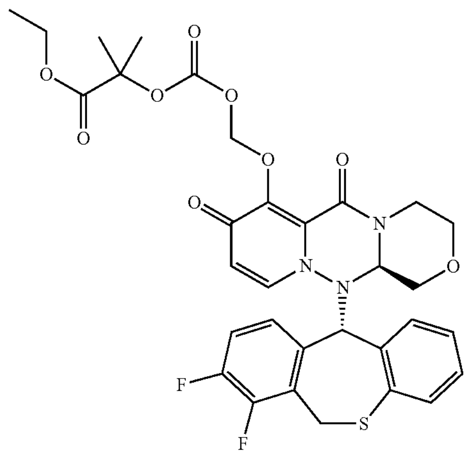 [SMILES: CCOC(=O)C(C)(C)OC(=O)OCOc1c2n(ccc1=O)N([C@@H]1c3ccccc3SCc3c1ccc(F)c3F)[C@@H]1COCCN1C2=O] | LC/MS (ESI): m/z = 672 [M + H]+, RT = 2.31 min, method (1) |
| II-89 | 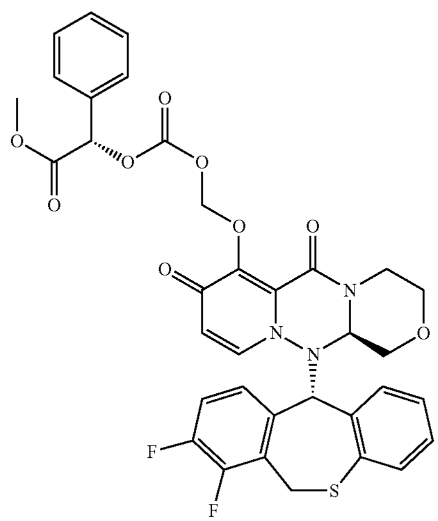 [SMILES: COC(=O)[C@@H](OC(=O)OCOc1c2n(ccc1=O)N([C@@H]1c3ccccc3SCc3c1ccc(F)c3F)[C@@H]1COCCN1C2=O)c1ccccc1] | LC/MS (ESI): m/z = 706 [M + H]+, RT = 2.37 min, method (1) |
| II-90 | 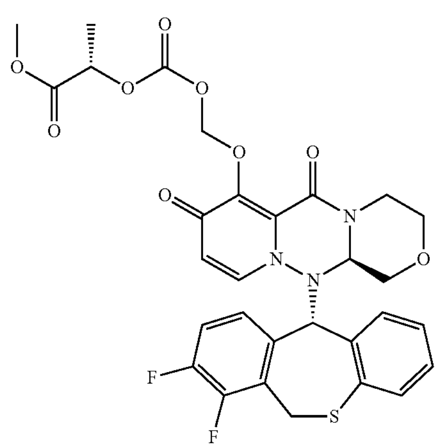 [SMILES: COC(=O)[C@H](C)OC(=O)OCOc1c2n(ccc1=O)N([C@@H]1c3ccccc3SCc3c1ccc(F)c3F)[C@@H]1COCCN1C2=O] | LC/MS (ESI): m/z = 644 [M + H]+, RT = 2.13 min, method (1) |

TABLE 27

| No. | Structure | NMR or LC/MS |
|---|---|---|
| II-91 | 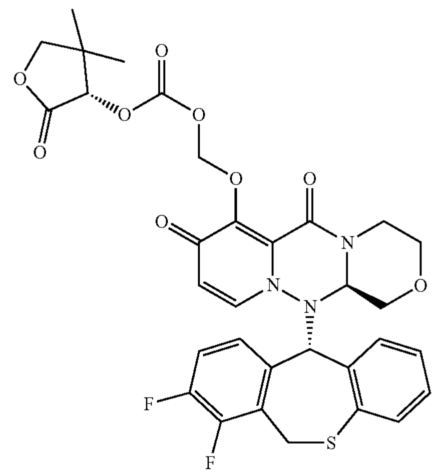 [SMILES: CC1(C)COC(=O)[C@H]1OC(=O)OCOc1c2n(ccc1=O)N([C@@H]1c3ccccc3SCc3c1ccc(F)c3F)[C@@H]1COCCN1C2=O] | LC/MS (ESI): m/z = 670 [M + H]+, RT = 2.16 min, method (1) |
| II-92 | 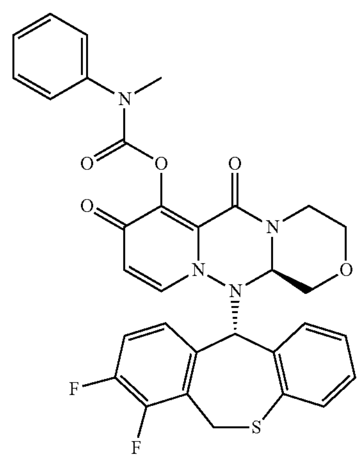 [SMILES: CN(C(=O)Oc1c2n(ccc1=O)N([C@@H]1c3ccccc3SCc3c1ccc(F)c3F)[C@@H]1COCCN1C2=O)c1ccccc1] | LC/MS (ESI): m/z = 617.00 [M + H]+, RT = 2.09 min, method (2) |
| II-93 | 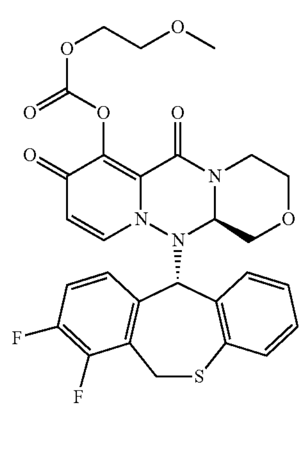 [SMILES: COCCOC(=O)Oc1c2n(ccc1=O)N([C@@H]1c3ccccc3SCc3c1ccc(F)c3F)[C@@H]1COCCN1C2=O] | LC/MS (ESI): m/z = 586.00 [M + H]+, RT = 1.91 min, method (2) |

TABLE 27-continued

| No. | Structure | NMR or LC/MS |
|---|---|---|
| II-94 | 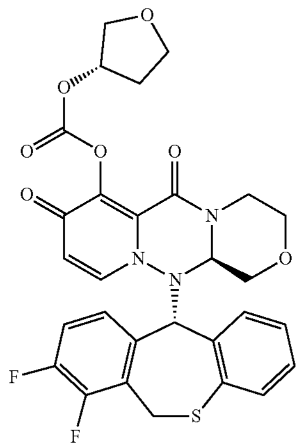 [SMILES: O=C(Oc1c2n(ccc1=O)N([C@@H]1c3ccccc3SCc3c1ccc(F)c3F)[C@@H]1COCCN1C2=O)O[C@H]1CCOC1] | LC/MS (ESI): m/z = 598.00 [M + H]+, RT = 1.89 min, method (2) |
| II-95 | 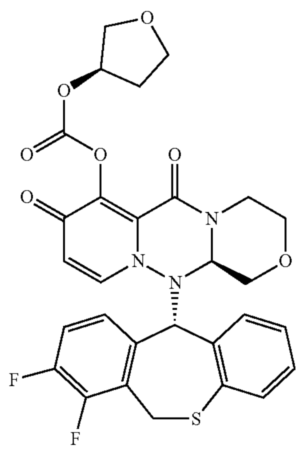 [SMILES: O=C(Oc1c2n(ccc1=O)N([C@@H]1c3ccccc3SCc3c1ccc(F)c3F)[C@@H]1COCCN1C2=O)O[C@@H]1CCOC1] | LC/MS (ESI): m/z = 598.00 [M + H]+, RT = 1.89 min, method (2) |

TABLE 28

| No. | Structure | NMR or LC/MS |
|---|---|---|
| II-96 | 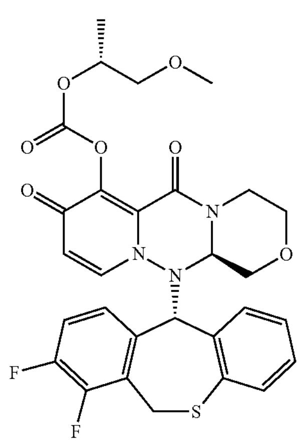 [SMILES: COC[C@@H](C)OC(=O)Oc1c2n(ccc1=O)N([C@@H]1c3ccccc3SCc3c1ccc(F)c3F)[C@@H]1COCCN1C2=O] | LC/MS (ESI): m/z = 600.00 [M + H]+, RT = 2.01 min, method (2) |

TABLE 28-continued

| No. | Structure | NMR or LC/MS |
|---|---|---|
| II-97 | 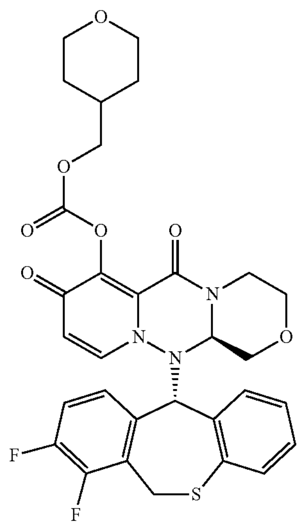 [SMILES: O=C(OCC1CCOCC1)Oc1c2n(ccc1=O)N([C@@H]1c3ccccc3SCc3c1ccc(F)c3F)[C@@H]1COCCN1C2=O] | LC/MS (ESI): m/z = 626.00 [M + H]+, RT = 1.98 min, method (2) |
| II-98 | 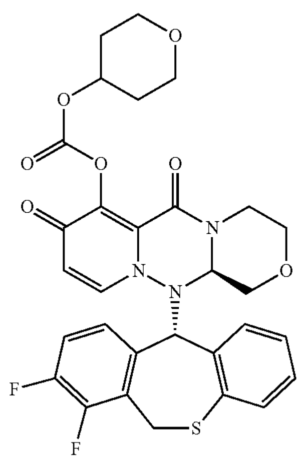 [SMILES: O=C(Oc1c2n(ccc1=O)N([C@@H]1c3ccccc3SCc3c1ccc(F)c3F)[C@@H]1COCCN1C2=O)OC1CCOCC1] | LC/MS (ESI): m/z = 611.95 [M + H]+, RT = 1.93 min, method (2) |
| II-99 | 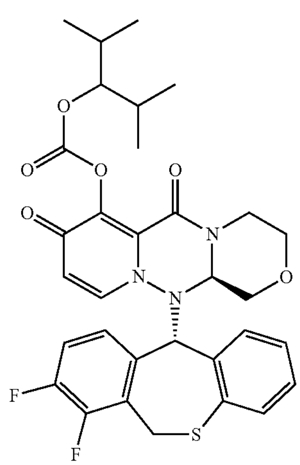 [SMILES: CC(C)C(OC(=O)Oc1c2n(ccc1=O)N([C@@H]1c3ccccc3SCc3c1ccc(F)c3F)[C@@H]1COCCN1C2=O)C(C)C] | LC/MS (ESI): m/z = 626.05 [M + H]+, RT = 2.46 min, method (2) |

TABLE 29

| No. | Structure | NMR or LC/MS |
|---|---|---|
| II-100 | 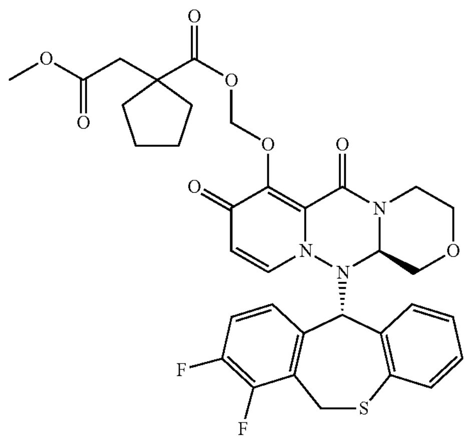 [SMILES: COC(=O)CC1(C(=O)OCOc2c3n(ccc2=O)N([C@@H]2c4ccccc4SCc4c2ccc(F)c4F)[C@@H]2COCCN2C3=O)CCCC1] | LC/MS (ESI): m/z = 682.05 [M + H]+, RT = 2.27 min, method (2) |
| II-101 | 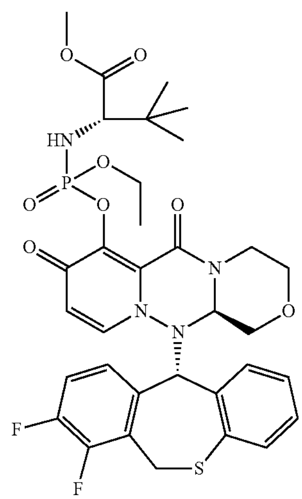 [SMILES: CCOP(=O)(N[C@H](C(=O)OC)C(C)(C)C)Oc1c2n(ccc1=O)N([C@@H]1c3ccccc3SCc3c1ccc(F)c3F)[C@@H]1COCCN1C2=O] | LC/MS (ESI): m/z = 719.05 [M + H]+, RT = 2.26 min, method (2) |
| II-102 | 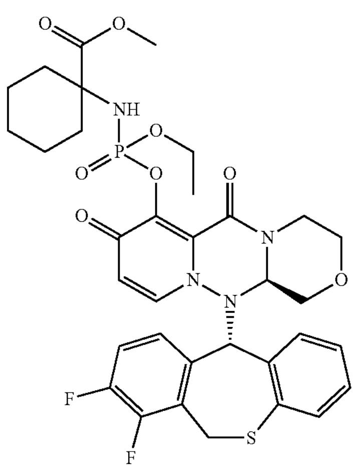 [SMILES: CCOP(=O)(NC1(C(=O)OC)CCCCC1)Oc1c2n(ccc1=O)N([C@@H]1c3ccccc3SCc3c1ccc(F)c3F)[C@@H]1COCCN1C2=O] | LC/MS (ESI): m/z = 731.15 [M + H]+, RT = 2.29 min, method (2) |

TABLE 29-continued

| No. | Structure | NMR or LC/MS |
|---|---|---|
| II-103 | 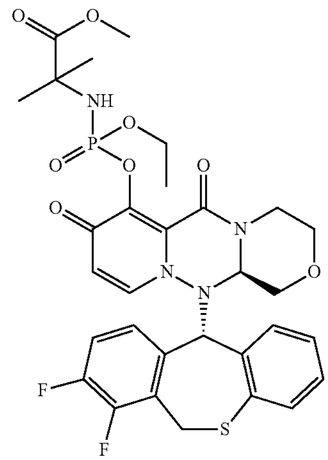 [SMILES: CCOP(=O)(NC(C)(C)C(=O)OC)Oc1c2n(ccc1=O)N([C@@H]1c3ccccc3SCc3c1ccc(F)c3F)[C@@H]1COCCN1C2=O] | LC/MS (ESI): m/z = 691.10 [M + H]+, RT = 2.05 min, method (2) |

TABLE 30

| No. | Structure | NMR or LC/MS |
|---|---|---|
| II-104 | 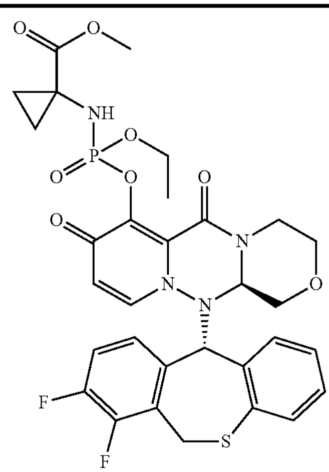 | LC/MS (ESI): m/z = 688.95 [M + H]+, RT = 1.98 min, method (2) |
| II-105 | 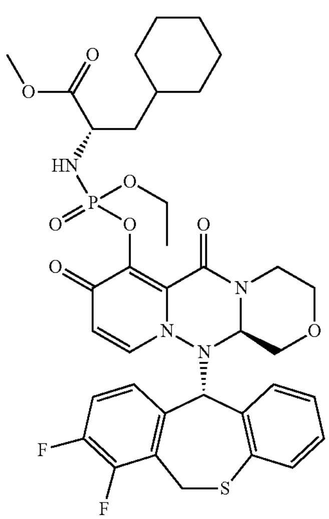 [SMILES: CCOP(=O)(N[C@@H](CC1CCCCC1)C(=O)OC)Oc1c2n(ccc1=O)N([C@@H]1c3ccccc3SCc3c1ccc(F)c3F)[C@@H]1COCCN1C2=O] | LC/MS (ESI): m/z = 759.05 [M + H]+, RT = 2.53 min, method (2) |

TABLE 30-continued

| No. | Structure | NMR or LC/MS |
|---|---|---|
| II-106 | 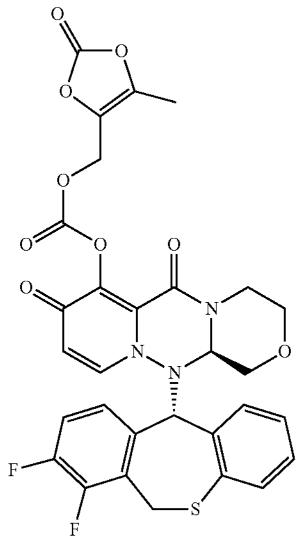 [SMILES: Cc1oc(=O)oc1COC(=O)Oc1c2n(ccc1=O)N([C@@H]1c3ccccc3SCc3c1ccc(F)c3F)[C@@H]1COCCN1C2=O] | LC/MS (ESI): m/z = 639.95 [M + H]+, RT = 2.01 min, method (2) |
| II-107 | 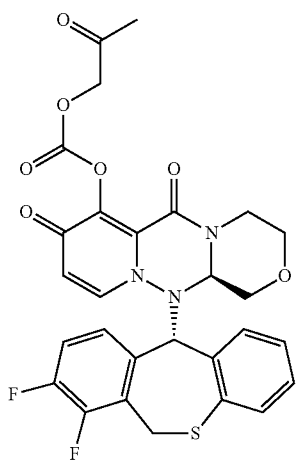 | LC/MS (ESI): m/z = 683.95 [M + H]+, RT = 1.87 min, method (2) |

TABLE 31

| No. | Structure | NMR or LC/MS |
|---|---|---|
| II-108 | 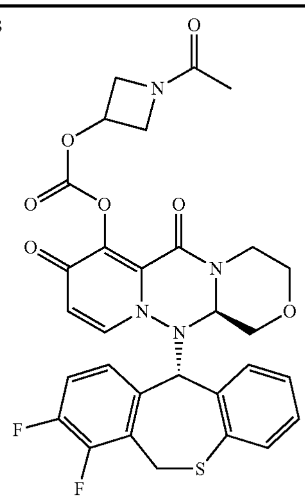 | LC/MS (ESI): m/z = 625.00 [M + H]+, RT = 1.75 min, method (2) |

TABLE 31-continued

| No. | Structure | NMR or LC/MS |
| --- | --- | --- |
| II-109 | 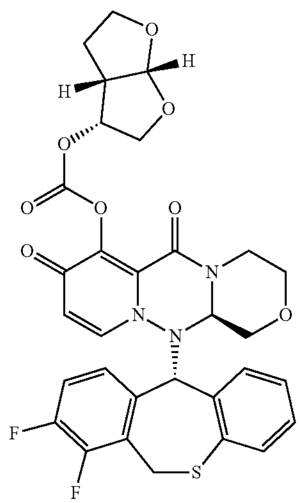 [SMILES: O=C(Oc1c2n(ccc1=O)N([C@@H]1c3ccccc3SCc3c1ccc(F)c3F)[C@@H]1COCCN1C2=O)O[C@H]1CO[C@H]2OCC[C@H]21] | LC/MS (ESI): m/z = 640.00 [M + H]+, RT = 1.90 min, method (2) |
| II-110 | 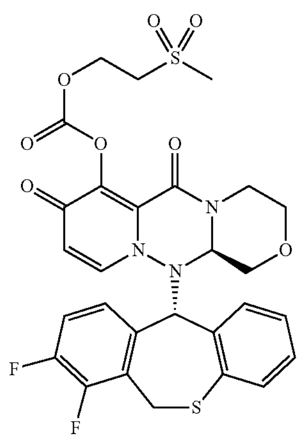 [SMILES: CS(=O)(=O)CCOC(=O)Oc1c2n(ccc1=O)N([C@@H]1c3ccccc3SCc3c1ccc(F)c3F)[C@@H]1COCCN1C2=O] | LC/MS (ESI): m/z = 633.90 [M + H]+, RT = 1.82 min, method (2) |
| II-111 | 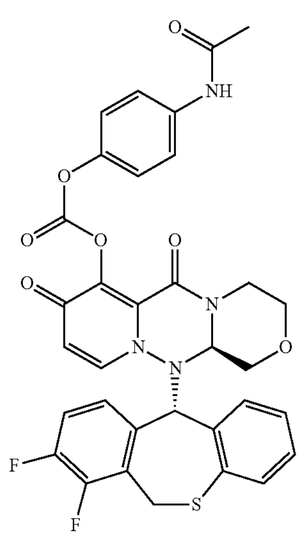 [SMILES: CC(=O)Nc1ccc(OC(=O)Oc2c3n(ccc2=O)N([C@@H]2c4ccccc4SCc4c2ccc(F)c4F)[C@@H]2COCCN2C3=O)cc1] | LC/MS (ESI): m/z = 661.00 [M + H]+, RT = 1.90 min, method (2) |

TABLE 32

| No. | Structure | NMR or LC/MS |
|---|---|---|
| II-112 | 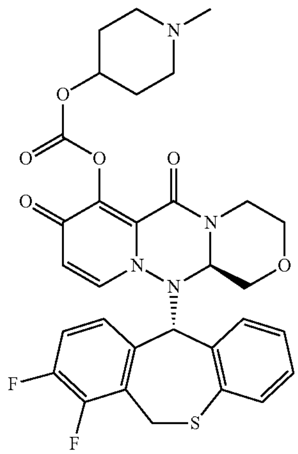 [SMILES: CN1CCC(OC(=O)Oc2c3n(ccc2=O)N([C@@H]2c4ccccc4SCc4c2ccc(F)c4F)[C@@H]2COCCN2C3=O)CC1] | LC/MS (ESI): m/z = 624.95 [M + H]+, RT = 1.38 min, method (2) |
| II-113 | 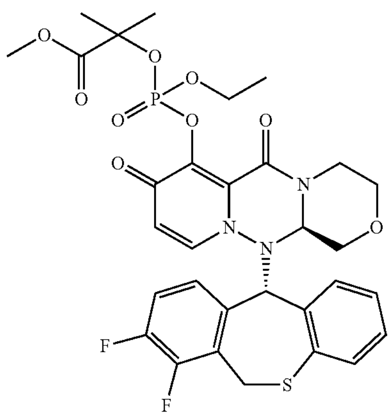 [SMILES: CCOP(=O)(Oc1c2n(ccc1=O)N([C@@H]1c3ccccc3SCc3c1ccc(F)c3F)[C@@H]1COCCN1C2=O)OC(C)(C)C(=O)OC] | LC/MS (ESI): m/z = 691.95 [M + H]+, RT = 2.00 min, method (2) |
| II-114 | 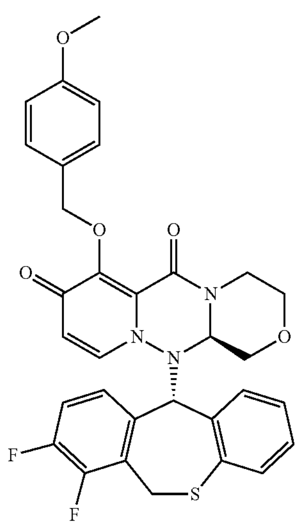 [SMILES: COc1ccc(COc2c3n(ccc2=O)N([C@@H]2c4ccccc4SCc4c2ccc(F)c4F)[C@@H]2COCCN2C3=O)cc1] | LC/MS (ESI): m/z = 604.00 [M + H]+, RT = 2.09 min, method (2) |

TABLE 32-continued

| No. | Structure | NMR or LC/MS |
|---|---|---|
| II-116 | 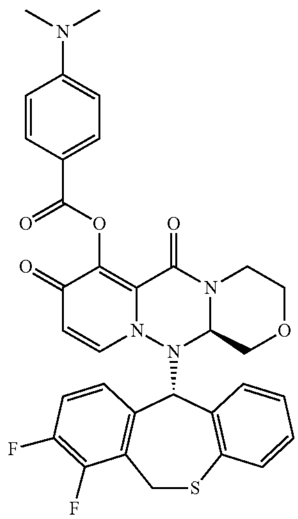 [SMILES: CN(C)c1ccc(C(=O)Oc2c3n(ccc2=O)N([C@@H]2c4ccccc4SCc4c2ccc(F)c4F)[C@@H]2COCCN2C3=O)cc1] | LC/MS (ESI): m/z = 631.00 [M + H]+, RT = 2.18 min, method (2) |

TABLE 33

| No. | Structure | NMR or LC/MS |
|---|---|---|
| II-117 | 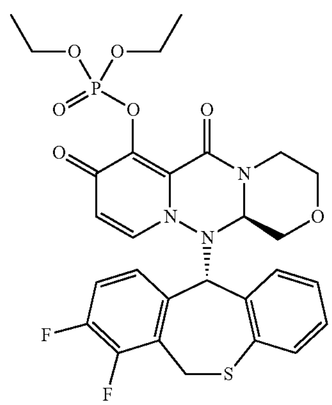 [SMILES: CCOP(=O)(OCC)Oc1c2n(ccc1=O)N([C@@H]1c3ccccc3SCc3c1ccc(F)c3F)[C@@H]1COCCN1C2=O] | LC/MS (ESI): m/z = 620.00 [M + H]+, RT = 1.93 min, method (2) |
| II-118 | 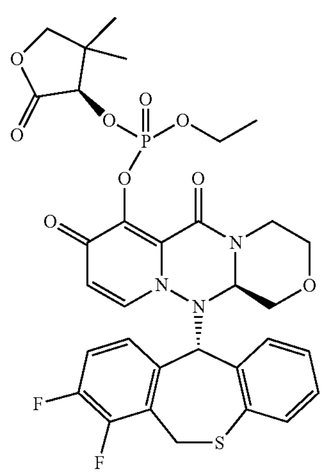 | LC/MS (ESI): m/z = 620.00 [M + H]+, RT = 1.93 min, method (2) |

TABLE 33-continued

| No. | Structure | NMR or LC/MS |
|---|---|---|
| II-119 | 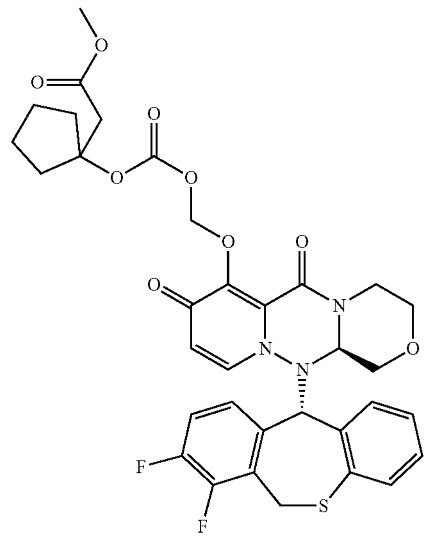 | LC/MS (ESI): m/z = 614 [M + H]+, RT = 2.31 min, method (1) |
| II-120 | 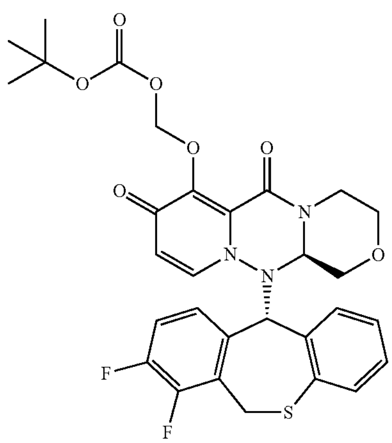 [SMILES: CC(C)(C)OC(=O)OCOc1c2n(ccc1=O)N([C@@H]1c3ccccc3SCc3c1ccc(F)c3F)[C@@H]1COCCN1C2=O] | LC/MS (ESI): m/z = 614 [M + H]+, RT = 2.24 min, method (1) |

TABLE 34

| No. | Structure | NMR or LC/MS |
|---|---|---|
| II-121 | 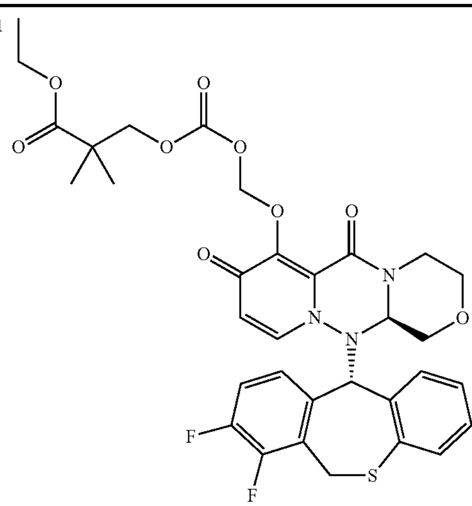 | LC/MS (ESI): m/z = 686 [M + H]+, RT = 2.27 min, method (1) |

TABLE 34-continued

| No. | Structure | NMR or LC/MS |
|---|---|---|
| II-122 | 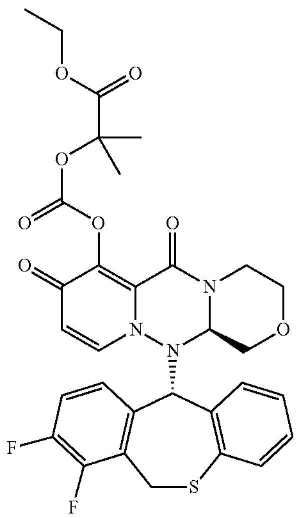 [SMILES: CCOC(=O)C(C)(C)OC(=O)Oc1c2n(ccc1=O)N([C@@H]1c3ccccc3SCc3c1ccc(F)c3F)[C@@H]1COCCN1C2=O] | LC/MS (ESI): m/z = 642 [M + H]+, RT = 2.19 min, method (1) |
| II-123 | 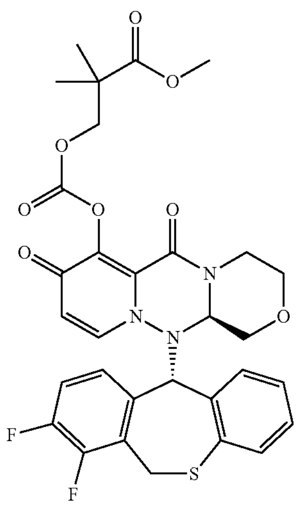 [SMILES: COC(=O)C(C)(C)COC(=O)Oc1c2n(ccc1=O)N([C@@H]1c3ccccc3SCc3c1ccc(F)c3F)[C@@H]1COCCN1C2=O] | LC/MS (ESI): m/z = 642 [M + H]+, RT = 2.17 min, method (1) |
| II-124 | 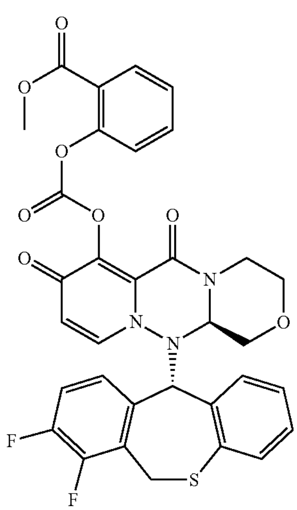 [SMILES: COC(=O)c1ccccc1OC(=O)Oc1c2n(ccc1=O)N([C@@H]1c3ccccc3SCc3c1ccc(F)c3F)[C@@H]1COCCN1C2=O] | LC/MS (ESI): m/z = 662 [M + H]+, RT = 2.22 min, method (1) |

TABLE 35

| No. | Structure | NMR or LC/MS |
| --- | --- | --- |
| II-125 | 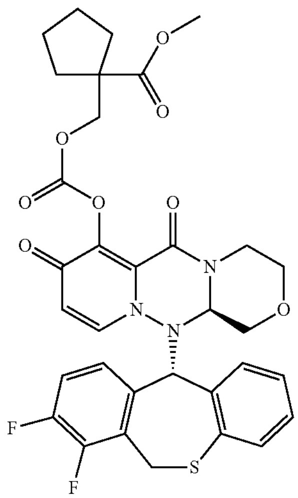 [SMILES: COC(=O)C1(COC(=O)Oc2c3n(ccc2=O)N([C@@H]2c4ccccc4SCc4c2ccc(F)c4F)[C@@H]2COCCN2C3=O)CCCC1] | LC/MS (ESI): m/z = 668 [M + H]+, RT = 2.32 min, method (1) |
| II-126 | 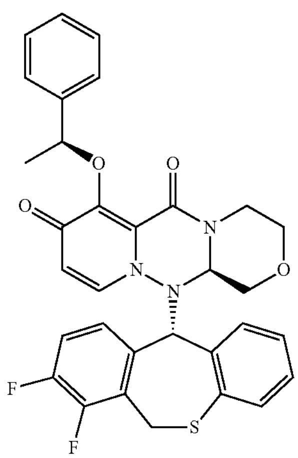 [SMILES: C[C@H](Oc1c2n(ccc1=O)N([C@@H]1c3ccccc3SCc3c1ccc(F)c3F)[C@@H]1COCCN1C2=O)c1ccccc1] | LC/MS (ESI): m/z = 587.95 [M + H]+, RT = 2.24 min, method (2) |
| II-127 | 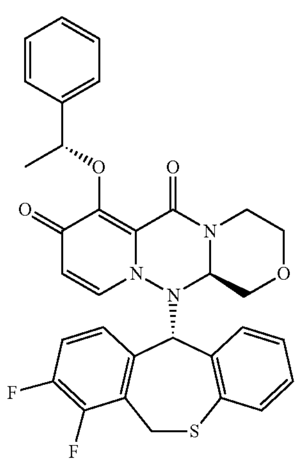 [SMILES: C[C@@H](Oc1c2n(ccc1=O)N([C@@H]1c3ccccc3SCc3c1ccc(F)c3F)[C@@H]1COCCN1C2=O)c1ccccc1] | LC/MS (ESI): m/z = 588.05 [M + H]+, RT = 2.17 min, method (2) |

TABLE 35-continued

| No. | Structure | NMR or LC/MS |
|---|---|---|
| II-128 | 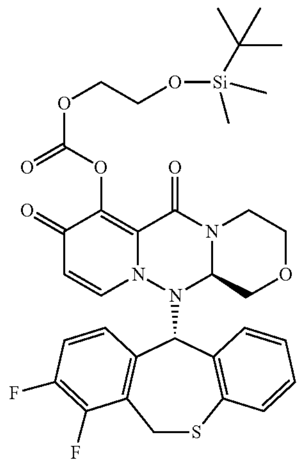 [SMILES: CC(C)(C)[Si](C)(C)OCCOC(=O)Oc1c2n(ccc1=O)N([C@@H]1c3ccccc3SCc3c1ccc(F)c3F)[C@@H]1COCCN1C2=O] | LC/MS (ESI): m/z = 686.00 [M + H]+, RT = 2.67 min, method (2) |

TABLE 36

| No. | Structure | NMR or LC/MS |
|---|---|---|
| II-130 | 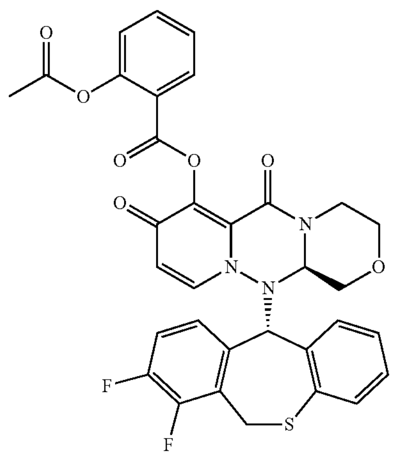 [SMILES: CC(=O)Oc1ccccc1C(=O)Oc1c2n(ccc1=O)N([C@@H]1c3ccccc3SCc3c1ccc(F)c3F)[C@@H]1COCCN1C2=O] | LC/MS (ESI): m/z = 645.95 [M + H]+, RT = 2.12 min, method (2) |
| II-131 | 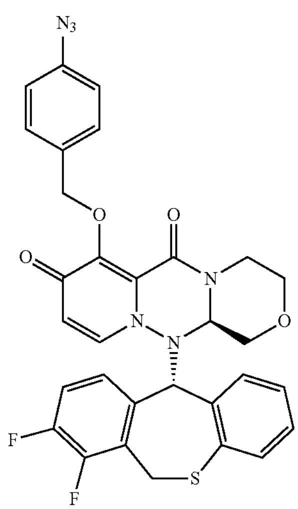 [SMILES: [N-]=[N+]=Nc1ccc(COc2c3n(ccc2=O)N([C@@H]2c4ccccc4SCc4c2ccc(F)c4F)[C@@H]2COCCN2C3=O)cc1] | LC/MS (ESI): m/z = 615.00 [M + H]+, RT = 2.24 min, method (2) |

TABLE 36-continued
| No. | Structure | NMR or LC/MS |
|---|---|---|
| II-132 | 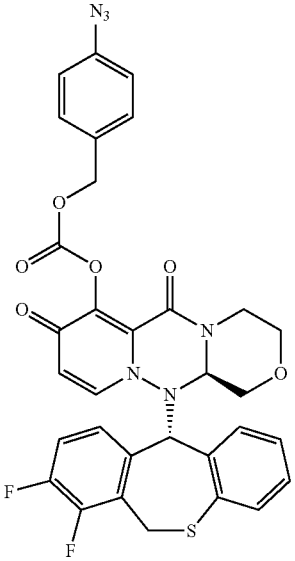 [SMILES: [N-]=[N+]=Nc1ccc(COC(=O)Oc2c3n(ccc2=O)N([C@@H]2c4ccccc4SCc4c2ccc(F)c4F)[C@@H]2COCCN2C3=O)cc1] | LC/MS (ESI): m/z = 658.95 [M + H]+, RT = 2.31 min, method (2) |
| II-133 | 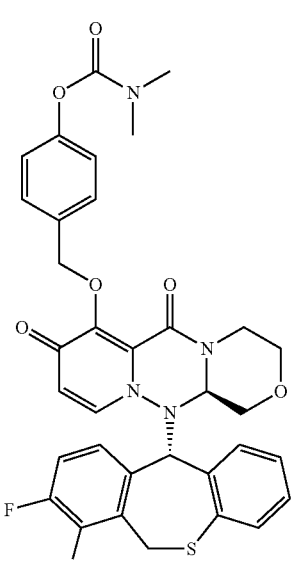 | LC/MS (ESI): m/z = 661.00 [M + H]+, RT = 2.06 min, method (2) |

TABLE 37

| No. | Structure | NMR or LC/MS |
|---|---|---|
| II-134 | 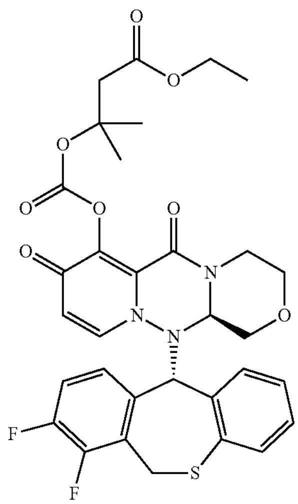 [SMILES: CCOC(=O)CC(C)(C)OC(=O)Oc1c2n(ccc1=O)N([C@@H]1c3ccccc3SCc3c1ccc(F)c3F)[C@@H]1COCCN1C2=O] | LC/MS (ESI): m/z = 656 [M + H]+, RT = 2.24 min, method (1) |
| II-135 | 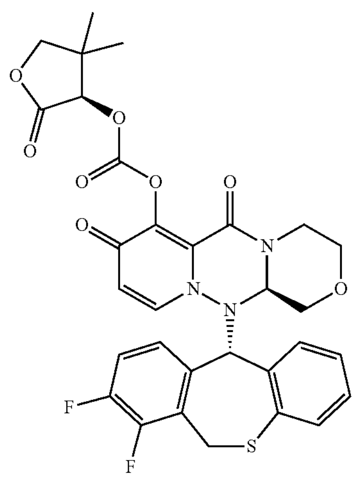 [SMILES: CC1(C)COC(=O)[C@@H]1OC(=O)Oc1c2n(ccc1=O)N([C@@H]1c3ccccc3SCc3c1ccc(F)c3F)[C@@H]1COCCN1C2=O] | 1H-NMR (CDCl3) δ: 1.24 (s, 3H), 1.38 (s, 3H), 2.94 (td, J = 11.8, 3.5 Hz, 1H), 3.44 (dd, J = 12.0, 10.9 Hz, 1H), 3.57 (t, J = 10.9 Hz, 1H), 3.78 (dd, J = 12.0, 3.5 Hz, 1H), 3.96 (dd, J = 10.9, 2.9 Hz, 1H), 4.05-4.12 (m, 3H), 4.58 (dd, J = 10.0, 2.9 Hz, 1H), 4.66 (d, J = 13.5 Hz, 1H), 5.24 (d, J = 13.5 Hz, 1H), 5.32 (s, 1H), 5.58 (s, 1H), 5.91 (d, J = 7.8 Hz, 1H), 6.81 (s, 2H), 7.06-7.20 (m, 5H). |
| II-136 | 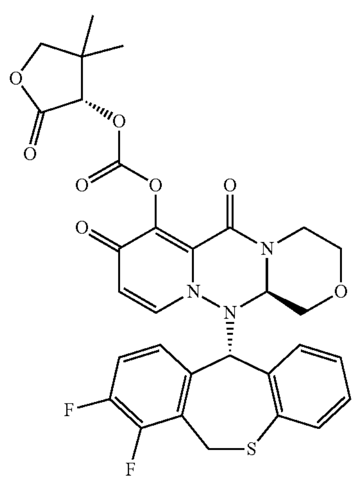 [SMILES: CC1(C)COC(=O)[C@H]1OC(=O)Oc1c2n(ccc1=O)N([C@@H]1c3ccccc3SCc3c1ccc(F)c3F)[C@@H]1COCCN1C2=O] | 1H-NMR (CDCl3) δ: 1.26 (s, 3H), 1.33 (s, 3H), 2.96 (t, J = 11.9 Hz, 1H), 3.46 (t, J = 10.6 Hz, 1H), 3.59 (t, J = 10.6 Hz, 1H), 3.77 (dd, J = 11.9, 2.9 Hz, 1H), 3.95 (dd, J = 11.0, 2.9 Hz, 1H), 4.04-4.13 (m, 3H), 4.56 (dd, J = 10.0, 2.9 Hz, 1H), 4.72 (d, J = 13.4 Hz, 1H), 5.27-5.31 (m, 2H), 5.37 (s, 1H), 5.91 (d, J = 8.0 Hz, 1H), 6.87-6.91 (m, 2H), 7.00-7.05 (m, 1H), 7.07-7.15 (m, 4H). |

TABLE 37-continued
| No. | Structure | NMR or LC/MS |
|---|---|---|
| II-137 | 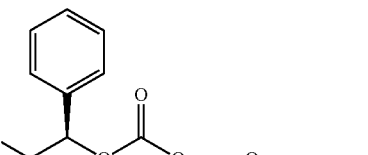 | 1H-NMR (CDCl3) δ: 2.92 (t, J = 11.0 Hz, 1H), 3.38 (t, J = 11.0 Hz, 1H), 3.56 (t, J = 10.4 Hz, 1H), 3.75 (d, J = 9.3 Hz, 1H), 3.81 (s, 3H), 3.95 (d, J = 9.3 Hz, 1H), 4.06 (d, J = 13.9 Hz, 1H), 4.55 (d, J = 8.1 Hz, 1H), 4.63 (d, J = 13.0 Hz, 1H), 5.27 (d, J = 13.9 Hz, 1H), 5.43 (br s, 1H), 5.91 (d, J = 8.1 Hz, 1H), 6.09 (s, 1H), 6.82-6.86 (m, 1H), 6.93 (d, J = 8.1 Hz, 1H), 7.04-7.13 (m, 5H), 7.39-7.43 (m, 3H), 7.56-7.59 (m, 2H). |
TABLE 38
| No. | Structure | NMR or LC/MS |
|---|---|---|
| II-138 | 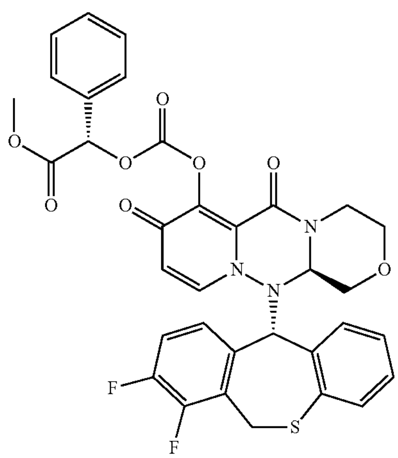 [SMILES: COC(=O)[C@@H](OC(=O)Oc1c2n(ccc1=O)N([C@@H]1c3ccccc3SCc3c1ccc(F)c3F)[C@@H]1COCCN1C2=O)c1ccccc1] | 1H-NMR (CDCl3) δ: 2.94 (t, J = 11.3 Hz, 1H), 3.41 (t, J = 11.3 Hz, 1H), 3.57 (t, J = 10.5 Hz, 1H), 3.76 (d, J = 11.0 Hz, 1H), 3.83 (s, 3H), 3.94 (dd, J = 10.5, 2.7 Hz, 1H), 4.06 (d, J = 14.0 Hz, 1H), 4.55 (dd, J = 9.5, 2.7 Hz, 1H), 4.68 (d, J = 12.6 Hz, 1H), 5.28 (d, J = 14.0 Hz, 1H), 5.35 (s, 1H), 5.90 (d, J = 8.0 Hz, 1H), 6.05 (s, 1H), 6.84-6.90 (m, 2H), 7.00-7.15 (m, 5H), 7.38-7.42 (m, 3H), 7.56-7.60 (m, 2H). |
| II-139 | 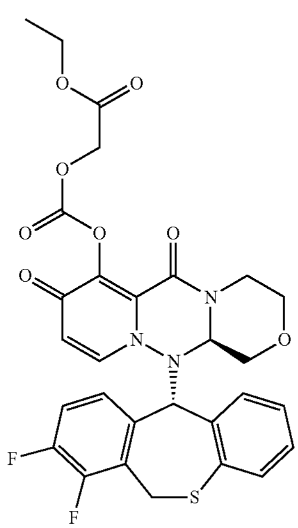 [SMILES: CCOC(=O)COC(=O)Oc1c2n(ccc1=O)N([C@@H]1c3ccccc3SCc3c1ccc(F)c3F)[C@@H]1COCCN1C2=O] | LC/MS (ESI): m/z = 614 [M + H]+, RT = 2.10 min, method (1) |

TABLE 38-continued

| No. | Structure | NMR or LC/MS |
|---|---|---|
| II-140 | 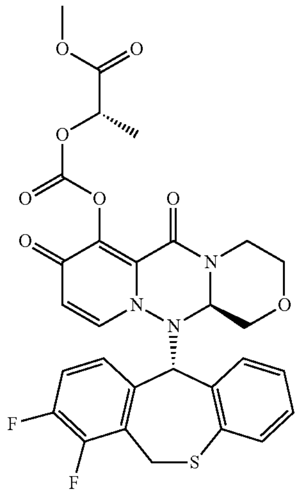 [SMILES: COC(=O)[C@H](C)OC(=O)Oc1c2n(ccc1=O)N([C@@H]1c3ccccc3SCc3c1ccc(F)c3F)[C@@H]1COCCN1C2=O] | LC/MS (ESI): m/z = 614 [M + H]+, RT = 2.04 min, method (1) |
| II-141 | 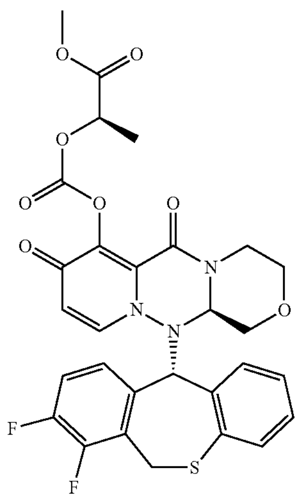 [SMILES: COC(=O)[C@@H](C)OC(=O)Oc1c2n(ccc1=O)N([C@@H]1c3ccccc3SCc3c1ccc(F)c3F)[C@@H]1COCCN1C2=O] | LC/MS (ESI): m/z = 614 [M + H]+, RT = 2.02 min, method (1) |

TABLE 39

| No. | Structure | NMR or LC/MS |
|---|---|---|
| II-142 | 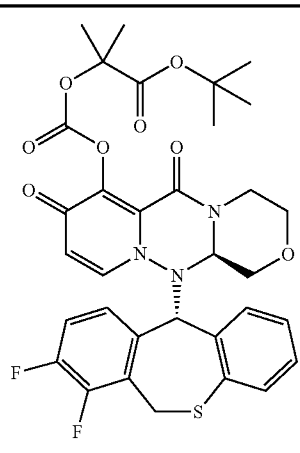 | LC/MS (ESI): m/z = 670 [M + H]+, RT = 2.41 min, method (1) |

TABLE 39-continued

| No. | Structure | NMR or LC/MS |
|---|---|---|
| II-144 | 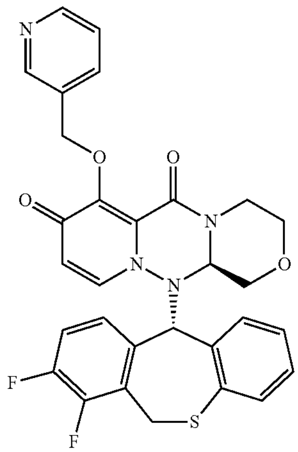 [SMILES: O=C1c2c(OCc3cccnc3)c(=O)ccn2N([C@@H]2c3ccccc3SCc3c2ccc(F)c3F)[C@@H]2COCCN12] | LC/MS (ESI): m/z = 575.20 [M + H]+, RT = 1.49 min, method (2) |
| II-145 | 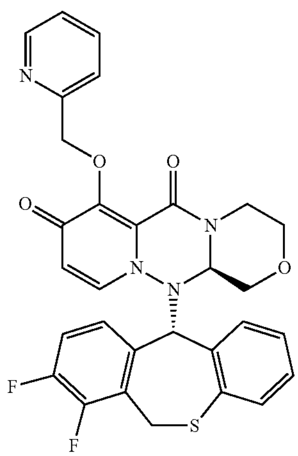 [SMILES: O=C1c2c(OCc3ccccn3)c(=O)ccn2N([C@@H]2c3ccccc3SCc3c2ccc(F)c3F)[C@@H]2COCCN12] | LC/MS (ESI): m/z = 575.00 [M + H]+, RT = 1.52 min, method (2) |
| II-146 | 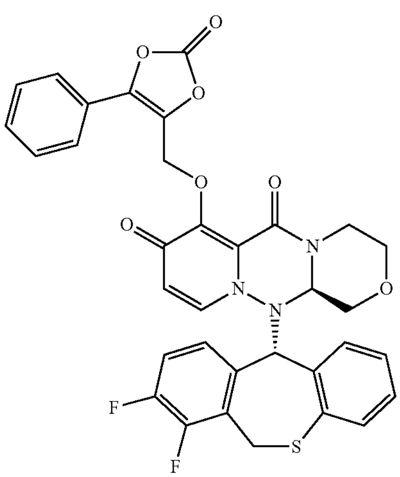 [SMILES: O=C1c2c(OCc3oc(=O)oc3-c3ccccc3)c(=O)ccn2N([C@@H]2c3ccccc3SCc3c2ccc(F)c3F)[C@@H]2COCCN12] | LC/MS (ESI): m/z = 657.90 [M + H]+, RT = 2.23 min, method (2) |

The compounds in connection with the present invention and/or the parent compounds of the compounds in connection with the present invention are useful for symptoms and/or diseases which are induced by influenza virus. For example, they are useful for treating and/or preventing, or improving symptoms of, cold-like symptoms accompanying fever, algor, headache, muscular pain, general malaise etc., airway inflammation symptoms such as pharyngalgia, nasal secretion, nasal congestion, cough, sputum etc., gastrointestinal symptoms such as abdominal pain, vomitus, diarrhea etc. and, further, complications accompanying secondary infection such as acute encephalopathy and pneumonia.

Since the compounds in connection with the present invention are a prodrug and thus have advantages that oral absorbability is high, good bioavailability is exhibited, good clearance is exhibited, and pulmonary transitivity is high, they can be excellent medicaments.

Since the parent compounds of the compounds in connection with the present invention have the effects such as high inhibitory activity on cap structure-dependent endonuclease, and high selectivity due to a virus-specific enzyme, they can be medicaments having reduced side effects.

Further, since the compounds in connection with the present invention and/or the parent compounds of the compounds in connection with the present invention also have advantages that metabolism stability is high, solubility is high, oral absorbability is high, good bioavailability is exhibited, good clearance is exhibited, pulmonary transitivity is high, a half life is long, a non-protein binding rate is high, hERG channel inhibition is low, CYP inhibition is low, CPE (CytoPathic Effect) inhibiting effect is recognized, and/or negativity is exhibited in a phototoxicity test, an Ames test and a gene toxicity test, or toxicity such as liver damage is not caused. Therefore, the compounds in connection with the present invention can be excellent medicaments.

The compounds in connection with the present invention and/or the parent compounds of the compounds in connection with the present invention can be administered orally or parenterally. In the case of oral administration, the present compounds can be also used as a normal preparation, for example, as any dosage form of solid preparations such as tablets, powders, granules, capsules etc.; solutions; oleaginous suspensions; or liquid preparations such as syrups or elixirs etc. In the case of parenteral administration, the compounds in connection with the present invention can be used as aqueous or oleaginous suspension injectables, or nose drops. Upon preparation of them, conventional excipients, binders, lubricants, aqueous solvents, oleaginous solvents, emulsifiers, suspending agents, preservatives, stabilizers etc. can be arbitrarily used. The pharmaceutical composition of the present invention can be produced by combining (for example, mixing) a therapeutically effective amount of the present compound with pharmaceutically acceptable carriers or diluents.

A dose of the compounds in connection with the present invention is different depending on an administration method, an age, a weight and the state of a patient, and a kind of a disease and, usually, in the case of oral administration, about 0.05 mg to 3000 mg, preferably about 0.1 mg to 1000 mg for adult per day may be administered, if necessary, by division. In addition, in the case of parenteral administration, about 0.01 mg to 1000 mg, preferably about 0.05 mg to 500 mg for adult per day is administered.

Test Example 1: Measurement of Cap-Dependant Endonuclease (CEN) Inhibitory Activity 1) Preparation of Substrate 30 merRNA(5'-pp-[m2'-O]GAA UAU(-Cy3) GCA UCA CUA GUA AGC UUU GCU CUA-BHQ2-3': manufactured by Japan Bio Services Co., LTD.) in which G at a 5' end is diphosphate-modified, a hydroxy group at 2' position is methoxylation-modified, U sixth from a 5' end is labelled with Cy3, and a 3' end is labelled with BHQ2 was purchased, and a cap structure was added using ScriptCap system manufactured by EPICENTRE (a product was m7G [5']-ppp-[5'] [m2'-O]GAA UAU(-Cy3) GCA UCA CUA GUAAGC UUU GCU CUA(-BHQ2)-3'). This was separated and purified by denatured polyacrylamide gel electrophoresis, and used as a substrate.

2) Preparation of Enzyme

RNP was prepared from a virus particle using standard method (Reference Document: VIROLOGY (1976) 73, p 327-338 OLGA M. ROCHOVANSKY). Specifically, A/WSN/33 virus ($1\times10^3$ PFU/mL, 200 μL) was inoculated in a 10 days old embryonated chicken egg. After incubation at 37° C. for 2 days, the allantoic fluid of the chicken egg was recovered. A virus particle was purified by ultracentrifugation using 20% sucrose, solubilized using TritonX-100 and lysolecithin, and an RNP fraction (50-70% glycerol fraction) was collected by ultracentrifugation using a 30-70% glycerol density gradient, and was used as an enzyme solution (containing approximately 1 nM PB1-PB2-PA complex).

3) Enzymatic Reaction

An enzymatic reaction solution (2.5 μL) (composition: 53 mM Tris-hydrochloride (pH 7.8), 1 mM $MgCl_2$, 1.25 mM dithiothreitol, 80 mM NaCl, 12.5% glycerol, enzyme solution 0.15 μL) was dispensed into a 384-well plate made of polypropylene. Then, 0.5 μL of a test compound solution which had been serially diluted with dimethyl sulfoxide (DMSO) was added to the plate. As a positive control (PC) or a negative control (NC), 0.5 μL of DMSO was added to the plate respectively. Each plate was mixed well. Then, 2 μL of a substrate solution (1.4 nM substrate RNA, 0.05% Tween20) was added to initiate a reaction. After room temperature incubation for 60 minutes, 1 μL of the reaction solution was collected and added to 10 μL of a Hi-Di formamide solution (containing GeneScan 120 Liz Size Standard as a sizing marker: manufactured by Applied Biosystems (ABI)) in order to stop the reaction. For NC, the reaction was stopped in advance by adding EDTA (4.5 mM) before initiation of the reaction (all concentrations described above are final concentrations).

3) Measurement of Inhibition Ratio ($IC_{50}$ Value)

The solution for which the reaction was stopped was heated at 85° C. for 5 minutes, rapidly cooled on ice for 2 minutes, and analyzed with an ABI PRIZM 3730 genetic analyzer. A peak of the cap-dependent endonuclease product was quantitated by analysis software ABI Genemapper, a CEN reaction inhibition ratio (%) of a test compound was obtained by setting fluorescent intensities of PC and NC to be 0% inhibition and 100% inhibition, respectively, an $IC_{50}$ value was obtained using curve fitting software (XLfit2.0: Model 205 (manufactured by IDBS) etc.). The $IC_{50}$ values of test substances being a parent compound, are shown in Table 40.

Test Example 2: CPE Inhibitory Effect Confirming Assay

<Material>

2% FCS E-MEM (prepared by adding kanamycin and FCS to MEM (Minimum Essential Medium) (Invitrogen))

0.5% BSA E-MEM (prepared by adding kanamycin and BSA to MEM (Minimum Essential Medium) (Invitrogen))

HBSS (Hanks' Balanced Salt Solution)

MDBK cell

Cells were adjusted to the appropriate cell number ($3\times10^5$/mL) with 2% FCS E-MEM.

MDCK cell

After washing with HBSS two times, cells were adjusted to the appropriate cell number ($5\times10^5$/mL) with 0.5% BSA E-MEM.

Trypsin solution

Trypsin from porcine pancreas (SIGMA) was dissolved in PBS(−), and filtrated with a 0.45 μm filter.

EnVision (PerkinElmer)

WST-8 Kit (Kishida Chemical Co., Ltd.)
10% SDS solution
<Operation Procedure>
Dilution and Dispensation of Test Sample As a culture medium, 2% FCS E-MEM was used at the use of MDBK cells, and 0.5% BSA E-MEM was used at the use of MDCK cells. Hereinafter, for diluting virus, cells and a test sample, the same culture medium was used.

A test sample was diluted with a culture medium to an appropriate concentration in advance, and then 2 to 5-fold serial dilution on a 96 well plate (50 µL/well) was prepared. Two plates, one for measuring anti-Flu activity and the another for measuring cytotoxity, were prepared. Each assay was performed triplicate for each drug.

At the use of MDCK cells, Trypsin was added to the cells to be a final concentration of 3 µg/mL only for measuring anti-Flu activity.

Dilution and Dispensation of Influenza Virus

An influenza virus was diluted with a culture medium to an appropriate concentration in advance, and each 50 µL/well was dispensed on a 96-well plate containing a test substance. Each 50 µL/well of a culture medium was dispensed on a plate containing a test substance for measuring cytotoxicity.

Dilution and Dispensation of Cell

Each 100 µL/well of cells which had been adjusted to the appropriate cell number was dispensed on a 96 well plate containing a test sample.

This was mixed with a plate mixer, and incubated in a CO2 incubator for 3 days for measuring anti-Flu activity and measuring cytotoxicity.

Dispensation of WST-8

The cells in the 96-well plate which had been incubated for 3 days was observed visually under a microscope, and appearance of the cells, the presence or absence of a crystal of test substance were checked. The supernatant was removed so that the cells were not absorbed from the plate.

WST-8 Kit was diluted 10-fold with a culture medium, and each 100 µL was dispensed into each well. After mixing with a plate mixer, cells were incubated in a CO2 incubator for 1 to 3 hours.

After incubation, regarding the plate for measuring anti-Flu activity, each 10 µL/well of a 10% SDS solution was dispensed in order to inactivate a virus.

Measurement of Absorbance

After the 96-well plate was mixed, absorbance was measured with EnVision at two wavelengths of 450 nm/620 nm.
<Calculation of Each Measurement Item Value>

The value was calculated using Microsoft Excel or a program having the equivalent calculation and processing ability, based on the following calculation equation.

Calculation of Effective Inhibition Concentration to Achieve 50% Influenza Infected Cell Death (EC50)

$$EC50 = 10^Z$$

$$Z = (50\% - \text{High }\%)/(\text{High }\% - \text{Low }\%) \times \{\log(\text{High conc.}) - \log(\text{Low conc.})\} + \log(\text{High conc.})$$

For test substances (compounds of Reference examples) being a parent compound, measurement results of Test Example 1 and Test Example 2 are shown in Table 40.

TABLE 40

| No. | CEN_IC50 nM | CPE_EC50 nM |
|---|---|---|
| III-1 | 10.90 | 2.10 |
| III-2 | 1.93 | 1.13 |

TABLE 40-continued

| No. | CEN_IC50 nM | CPE_EC50 nM |
|---|---|---|
| III-3 | 2.22 | 3.39 |
| III-4 | 2.81 | 2.08 |
| III-5 | 10.80 | 4.28 |
| III-7 | 8.09 | 11.50 |
| III-8 | 2.81 | 7.18 |
| III-9 | 2.17 | 10.90 |
| III-10 | 4.05 | 3.46 |
| III-11 | 13.10 | 9.98 |
| III-12 | 2.18 | 3.38 |
| III-13 | 3.94 | 4.00 |
| III-14 | 15.00 | 15.70 |
| III-15 | 37.30 | 16.90 |
| III-16 | 4.33 | 10.20 |
| III-17 | 3.89 | 8.14 |
| III-18 | 2.37 | 3.28 |
| III-19 | 2.37 | 1.43 |
| III-20 | 3.24 | 4.00 |
| III-21 | 4.06 | 2.70 |
| III-22 | 3.46 | 3.07 |
| III-23 | 1.48 | 0.86 |
| III-24 | 13.30 | 24.10 |
| III-25 | 2.96 | 2.35 |
| III-26 | 1.63 | 3.00 |
| III-27 | 4.19 | 3.61 |
| III-28 | 10.70 | 5.67 |
| III-29 | 0.87 | 0.66 |
| III-30 | 5.68 | 3.01 |
| III-31 | 18.50 | 3.17 |
| III-32 | 27.60 | 7.23 |
| III-33 | 2.08 | 2.36 |
| III-34 | 4.69 | 2.85 |
| III-35 | 3.86 | 3.00 |
| III-36 | 2.37 | 2.45 |
| III-37 | 4.24 | 3.43 |
| III-38 | 8.26 | 4.04 |
| III-39 | 2.75 | 2.81 |
| III-40 | 2.99 | 2.95 |
| III-41 | 2.10 | 2.17 |
| III-42 | 3.93 | 2.64 |
| III-43 | 3.90 | 3.18 |
| III-44 | 3.81 | 3.68 |
| III-45 | 1.63 | 3.07 |
| III-46 | 2.91 | 3.18 |
| III-47 | 2.25 | 2.53 |
| III-48 | 3.49 | 3.57 |
| III-49 | 6.79 | 4.17 |
| III-50 | 2.55 | 4.36 |
| III-51 | 2.22 | 2.58 |
| III-52 | 3.62 | 3.28 |

TABLE 41

| No. | CEN_IC50 nM | CPE_EC50 nM |
|---|---|---|
| III-53 | 2.46 | 3 |
| III-54 | 1.27 | 1.18 |
| III-55 | 2.13 | 3.45 |
| III-56 | 6.64 | 4.99 |
| III-57 | 4.27 | 3.47 |
| III-58 | 2.65 | 3.13 |
| III-59 | 0.57 | 3.11 |

Based on the above results, the parent compounds exhibit high cap-dependent endonuclease (CEN) inhibitory activity and/or high CPE inhibitory effect and thus can be a useful agent for treatment and/or prevention of symptom and/or disease induced by infection with influenza virus.

Biological test examples for compounds of the present invention were described below.

Test Example 3: CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a compound of the present invention was assessed.

The reaction conditions were as follows: substrate, 0.5 µmol/L ethoxyresorufin (CYP1A2), 100 µmol/L tolbutamide (CYP2C9), 50 µmol/L S-mephenytoinmephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; concentration of a compound of the present invention, 1, 5, 10, 20 µmol/L (four points).

Each five kinds of substrates, human hepatic microsome, or a compound of the present invention in 50 mmol/L Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and toltributamide hydroxide (CYP2C9P metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a compound of the present invention to a reaction system was adopted as a control (100%), remaining activity (%) was calculated at each concentration of a compound of the present invention added as the solution and IC50 was calculated by reverse presumption by a logistic model using a concentration and an inhibition rate.

(Result)
Compound III-2: five kinds >20 µmol/L

Test Example 4: BA Test

Materials and Methods for Experiments to Evaluate Oral Absorption
(1) Experimental animals: mice or SD rats were used.
(2) Rearing condition: mice or SD rats were allowed free access to solid feed and sterilized tap water.
(3) Setting of dosage and grouping: Oral administration and intravenous administration were performed with the predetermined dosage. Grouping was set as below. (Dosage was changed per compound)
  Oral administration 1 to 30 mg/kg (n=2 to 3)
  Intravenous administration 0.5 to 10 mg/kg (n=2 to 3)
(4) Preparation of administration solutions: Oral administration was performed as solution or suspension. Intravenous administration was performed after solubilization.
(5) Routes of administration: Oral administration was performed mandatory into the stomach by oral sonde. Intravenous administration was performed from caudal vein by syringes with needle.
(6) Evaluation items: Blood was collected serially and concentration of a compound of the present invention in plasma was measured by LC/MS/MS.
(7) Statistical analysis: About transition of concentration of a compound of the present invention in plasma, the area under the plasma concentration versus time curve (AUC) was calculated by non-linear least-squares method program, WinNonlin (a registered trademark), and bioavailability (BA) of a compound of the present invention was calculated from AUCs of the oral administration group and the intravenous administration group.

(Result)
Compound II-6: 14.9%
Compound III-2: 4.2%

Based on the above results, the prodrug had improved bioavailability other than the parent compound.

Therefore, the compound of the present invention has excellent oral absorb ability and can be a useful agent for treatment and/or prevention of symptom an d/or disease induced by infection with influenza virus.

Test Example 5: Metabolism Stability Test

Using commercially available pooled human hepatic microsomes, a compound of the present invention was reacted for a constant time, and a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The compound of the present invention in the supernatant was quantified by LC/MS/MS or Solid Phase Extraction (SPE)/MS, and a remaining amount of the compound of the present invention after the reaction was calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.

(Result) % inhibition was shown at 2 µmol/L of test compound.
Compound III-2: 90.1%

Test Example 6: CYP3A4 Fluorescent MBI Test

The CYP3A4 fluorescent MBI test is a test of investigating enhancement of CYP3A4 inhibition of a compound of the present invention by a metabolism reaction, and the test was performed using, as CYP3A4 enzyme expressed in *Escherichia coli* and employing, as an index, a reaction in which 7-benzyloxytrifluoromethylcoumarin (7-BFC) is debenzylated by the CYP3A4 enzyme to produce a metabolite, 7-hydroxytrifluoromethylcoumarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 µmol/mL, at reaction 6.25 µmol/mL (at 10-fold dilution); test drug concentration of a compound of the present invention, 0.625, 1.25, 2.5, 5, 10, 20 μmol/L (six points).

An enzyme in a K-Pi buffer (pH 7.4) and a solution of a compound of the present invention as a pre-reaction solution were added to a 96-well plate at the above composition of the pre-reaction, a part of it was transferred to another 96-well plate so that it was 1/10 diluted with a substrate and a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 (V/V) was added to stop the reaction. In addition, NADPH was added to a remaining preincubation solution to initiate a preincubation (with pre-incubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 (V/V) was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a compound of the present invention to a reaction system was adopted as a control (100%), remaining activity (%) was calculated at each concentration of a compound of the present invention added as the solution, and $IC_{50}$ was calculated by reverse-presumption by a logistic model using a concentration and an inhibition rate. When a difference between $IC_{50}$ values is 5 μmol/L or more, this was defined as (+) and, when the difference is 3 μmol/L or less, this was defined as (−).
(Result)
Compound III-2: (−)

Test Example 7: Fluctuation Ames Test

Mutagenicity of compounds of the present invention was evaluated.

20 μL of freezing-stored rat typhoid *bacillus* (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution. The bacteria was suspended in 9 mL of a Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4 \cdot 7H_2O$: 0.1 g/L), the suspension was added to 110 mL of an Exposure medium (Micro F buffer containing Biotin: 8 μg/mL, histidine: 0.2 μg/mL, glucose: 8 mg/mL). The TA100 strain was added to 120 mL of the Exposure medium relative to 3.16 mL of the bacterial solution to prepare a test bacterial solution. Each 12 μL of DMSO solution of a compound of the present invention (several stage dilution from maximum dose 50 mg/mL at 2 to 3 fold ratio), DMSO as a negative control, and 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μl of the test bacterial solution and 90 μL of S9 mix under the metabolism activating condition) were mixed, and this was shaking-cultured at 37° C. for 90 minutes. 460 μL of the bacterial solution exposed to a compound of the present invention was mixed with 2300 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group. (−) means that mutagenicity is negative and (+) is positive.
(Result)
Compound III-2: (−)

Test Example 8: hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds, was recorded. After the generated current was stabilized, extracellular solution (NaCl: 135 mmol/L, KCl: 5.4 mmol/L, $NaH_2PO_4$: 0.3 mmol/L, $CaCl_2 \cdot 2H_2O$: 1.8 mmol/L, $MgCl_2 \cdot 6H_2O$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration, was applied to the cell at room temperature for 10 minutes. From the recording $I_{Kr}$, an absolute value of the tail peak current was measured based on the current value at the resting membrane potential using analysis software (DataXpress ver. 1, Molecular Devices Corporation). Further, the % inhibition relative to the tail peak current before application of the compound of the present invention was calculated, and compared with the vehicle-applied group (0.1% dimethyl sulfoxide solution) to assess influence of the compound of the present invention on $I_{Kr}$.
(Result) % inhibition was shown at 0.3 to 10 μM of test compound.
Compound III-2: 7.9%

Test Example 9: Solubility Test

The solubility of the compound of the present invention was determined under 1% DMSO addition conditions. A 10 mmol/L solution of the compound was prepared with DMSO, and 2 μL of the solution of the compound of the present invention was added, respectively, to 198 μL of JP-1 solution (water were added to 2.0 g of sodium chloride and 7.0 mL of hydrochloric acid to reach 1000 mL) and JP-2 solution (1 volume of water were added to 1 volume of the solution which 3.40 g of potassium dihydrogen phosphate and 3.55 g of anhydrous disodium hydrogen phosphate to reach 1000 mL). The mixture was shaked for 1 hour at a room temperature, and the mixture was filtered. The filtrate was ten-fold diluted with methanol/water=1/1(v/v), and the compound concentration in the filtrate was measured with LC/MS or SPE/MS by the absolute calibration method.
(Result)
Compound III-2: 42.2 μmol/L Test Example 10: Powder Solubility Test Appropriate amounts of the compound of the present invention was put into vials and 200 μL of JP-1st Fluid (water was added to 2.0 g of sodium chloride in 7.0 mL of hydrochloride acid to reach 1000 mL), JP-2nd Fluid (water was added to 500 mL of phosphate buffer solution with a pH of 6.8) and 20 mmol/L sodium taurocholate (TCA)/JP-2nd Fluid (JP-2nd Fluid was added to 1.08 g of TCA in JP-2nd Fluid to reach 100 mL) was added to each vial. When the compound was completely dissolved, appropriate amount of compound was added. After shaken for 1 hour at 37° C., the mixture was filtered and 100 μL of methanol was added to 100 μL of each filtrate (double dilution). Dilution magnification was changed if necessary. After it was confirmed whether there were air bubbles and precipitates in the vials, the vials were shaken with tight stopper. The compound concentration was determined with HPLC by the absolute calibration method.
(Result)
Compound III-2: JP-1 solution; 7.1 μg/mL, JP-2 solution; 4.4 μg/mL, 20 mmol/L TCA/JP-2 solution; 16.1 μg/mL Test Example 11: Ames Test Ames test was performed by using Salmonellas (*Salmonella typhimurium*) TA 98, TA100, TA1535 and TA1537 and *Escherichia coli* WP2uvrA as test strains with or without metabolic activation in the pre-incubation method to check the presence or absence of gene mutagenicity of compounds of the present invention.
(Result)
Compound III-2: (−)

Test Example 12: Light Hemolysis Test

The compound of the present invention was dissolved at target concentrations and was mixed with a 2.5 v/v % suspension of red blood cells prepared from a defibrinated blood of sheep on a microplate at concentrations of 0.0008 to 0.1 w/v %. The mixtures were exposed to 10 J/cm$^2$ of UV-irradiation within a range of wavelength 290 to 400 nm, UVA and UVB using ultra violet fluorescent lamps, GL20SE and FL20S-BLB lamps manufactured by Sankyo Denki Co., Ltd. and Panasonic Corporation, respectively. After the completion of the irradiation, the mixtures were centrifuged, and a supernatant of the mixture was collected and was located on a microplate. The phototoxicity was assessed by measuring an absorbance at wavelength of 540 nm and 630 nm in the supernatant. The absorbance data at wavelength of 540 nm and 630 nm were used as indicators of biomembrane damage (photohemolysis %) and hyperoxidation of lipid membrane (methemoglobin formation), respectively. The criteria of phototoxicity was as follows; It was judged to be non-phototoxic (−) when the photohemolysis %<10 and the maximal change in the absorbance at 630 nm (ΔOD)<0.05 were observed. It was judged to be non-phototoxic (+) when the photohemolysis was more than 10% and the maximal change in the absorbance at 630 nm (ΔOD) was more than 0.05.
(Result)
Compound III-2: (−)

FIGS. 1 and 2 show a result of measuring the plasma concentration of Compound III-2 and Compound II-6 after oral administration of prodrug Compound II-6, the parent compound of which is Compound III-2, to rat under non-fasting conditions.

In addition, the concentration of Compound II-6 in all plasma samples was a determination limit or less. Therefore, prodrug Compound II-6, the parent compound of which is Compound III-2 is found to have changed promptly to Compound III-2 in vivo after administration (see FIG. 2).

Based on the above test results, it was revealed that the compound converted into a prodrug was absorbed into the body after oral administration, and rapidly converted into a parent compound in the blood. Therefore, the compound of the present invention can be a useful agent for treatment and/or prevention of symptom and/or disease induced by infection with influenza virus.

Test Example 13: Intravenous Administration Test

Examined experimental materials and method of intravenous administration test
(1) Animals used: SD rats were used.
(2) Rearing conditions: Pellets and sterilized tap water were fed to SD rats ad libitum.
(3) Dosage and grouping: A predetermined dosage was intravenously administered. Groups were set as follows. (Dosage varied for each compound)
Intravenous administration 0.5-1 mg/kg (n=2-3)
(4) Preparation of administration solution: Intravenous administration was performed after solubilization.
(5) Administration method: Intravenous administration was performed with a needle-equipped syringe on the caudal vein.
(6) End point: Blood was collected over time, and the plasma concentration of the compound of the present invention was measured using LC/MS/MS.
(7) Statistical analysis: As for the transition of the plasma concentration of the compound of the present invention, the total body clearance (CLtot) and the elimination half-life (t1/2, z) were calculated using nonlinear least-squares program WinNonlin®.
(Results)
Compound No. III-2:
CLtot: 16.4 mL/min/kg
t1/2, z: 3.4 hours From the above results, it was found that Compound III-2 is a compound having a low total body clearance and a long half-life.

Therefore, the compound of the present invention has excellent persistence and can be a useful agent for treatment and/or prevention of symptom and/or disease induced by infection with influenza virus.

Formulation Example

The following Formulation Examples are only exemplified and not intended to limit the scope of the invention.

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to obtain powder medicines in the form of powders or fine granules. The powder medicines are filled into capsule containers to give capsules.

Formulation Example 3: Granules

The compounds of the present invention, lactose and calcium stearate are mixed uniformly and the mixture is compressed and molded. Then, it is crushed, granulated and sieved to give suitable sizes of granules.

Formulation Example 4: Orally Disintegrated Tablets

The compounds of the present invention and crystalline cellulose are mixed, granulated and tablets are made to give orally disintegrated tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injection.

Formulation Example 7: Infusions

The compounds of the present invention and phosphate buffer are mixed to give injection.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

The compound of the present invention has cap-dependent endonuclease (CEN) inhibitory activity after absorption into the body. The compound of the present invention can be a useful agent for treatment and/or prevention of symptom and/or disease induced by infection with influenza virus.

The invention claimed is:

1. A method for treating a disease caused by a virus having cap-dependent endonuclease comprising administering a compound represented by the following formula:

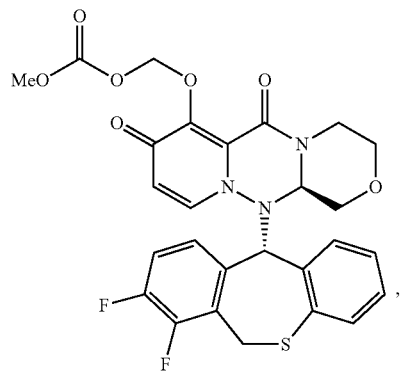 [SMILES: COC(=O)OCOc1c2n(ccc1=O)N([C@@H]1c3ccccc3SCc3c1ccc(F)c3F)[C@@H]1COCCN1C2=O]

or its pharmaceutically acceptable salt,
to a patient in need thereof.

2. A method for treating influenza comprising administering a compound represented by the following formula:

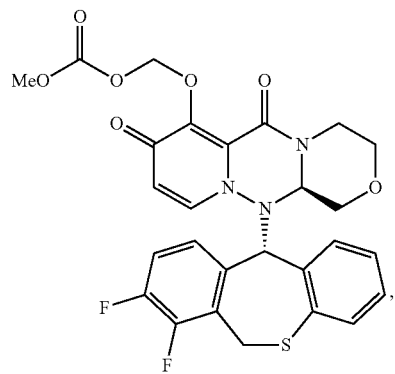 [SMILES: COC(=O)OCOc1c2n(ccc1=O)N([C@@H]1c3ccccc3SCc3c1ccc(F)c3F)[C@@H]1COCCN1C2=O]

or its pharmaceutically acceptable salt,
to a patient in need thereof.

3. A method for preventing influenza comprising administering a compound represented by the following formula:

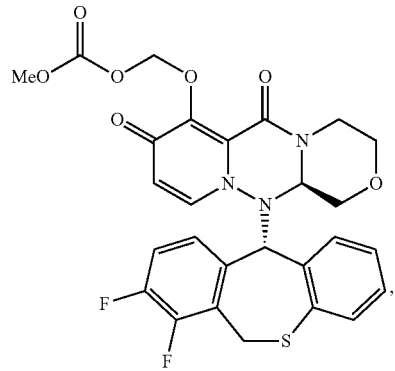 [SMILES: COC(=O)OCOc1c2n(ccc1=O)N([C@@H]1c3ccccc3SCc3c1ccc(F)c3F)[C@@H]1COCCN1C2=O]

or its pharmaceutically acceptable salt,
to a patient in need thereof.

4. The method of claim 1, wherein the patient is a human.

5. The method of claim 1, wherein the administering the compound comprises orally administering a dose of about 0.1 mg to 1000 mg of the compound, or its pharmaceutically acceptable salt.

6. The method of claim 5, wherein the patient is a human.

7. The method of claim 2, wherein the patient is a human.

8. The method of claim 2, wherein the administering the compound comprises orally administering a dose of about 0.1 mg to 1000 mg of the compound, or its pharmaceutically acceptable salt.

9. The method of claim 8, wherein the patient is a human.

10. The method of claim 3, wherein the patient is a human.

11. The method of claim 3, wherein the administering the compound comprises orally administering a dose of about 0.1 mg to 1000 mg of the compound, or its pharmaceutically acceptable salt.

12. The method of claim 11, wherein the patient is a human.

* * * * *